(12) United States Patent
Kim et al.

(10) Patent No.: US 6,376,497 B1
(45) Date of Patent: Apr. 23, 2002

(54) ANTIFUNGAL AZOLE DERIVATIVES HAVING A FLUORINATED VINYL GROUP AND PROCESS FOR PREPARING SAME

(75) Inventors: Bum-Tae Kim; Sun-Young Han; Chwang-Siek Pak, all of Daejeon (KR)

(73) Assignee: Korea Research Institute of Chemical Technology (KR)

( * ) Notice: Subject to any disclaimer, the term of this patent is extended or adjusted under 35 U.S.C. 154(b) by 0 days.

(21) Appl. No.: 09/889,128

(22) PCT Filed: Jan. 18, 2000

(86) PCT No.: PCT/KR00/00030

§ 371 Date: Jul. 6, 2001

§ 102(e) Date: Jul. 6, 2001

(87) PCT Pub. No.: WO00/43390

PCT Pub. Date: Jul. 27, 2000

(30) Foreign Application Priority Data

Jan. 19, 1999 (KR) .............................. 99-1424

(51) Int. Cl.[7] ................. A61K 31/496; A61K 31/4178; C07D 405/06; C07D 405/14
(52) U.S. Cl. .................. 514/254.07; 514/397; 514/383; 544/366; 544/370; 548/266.2; 548/268.8; 548/311.1; 548/315.1
(58) Field of Search ................. 544/366, 370; 548/266.2, 268.8, 311.1, 315.1; 514/254.07, 383, 397

(56) References Cited

U.S. PATENT DOCUMENTS 4,139,540 A * 2/1979 Heeres
4,223,036 A * 9/1980 Heeres et al.
4,229,460 A * 10/1980 Heeres et al.

* cited by examiner

Primary Examiner—Emily Bernhardt
(74) Attorney, Agent, or Firm—Anderson Kill & Olick, PC

(57) ABSTRACT

An antifungal compound of formula (I) or a pharmaceutically acceptable salt thereof:

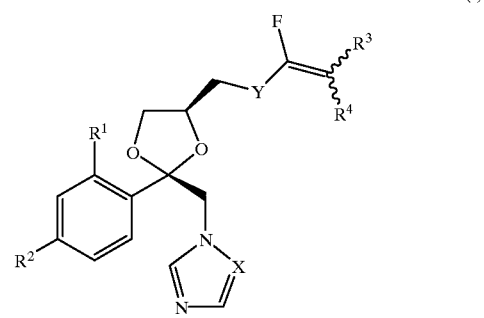

(I)

wherein:
X is CH or N;
Y is O,

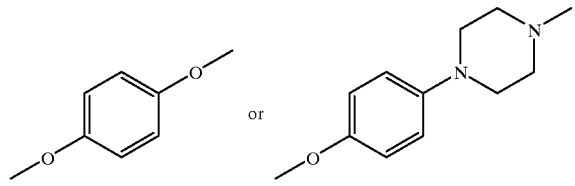

or $R^1$ and $R^2$ are each independently F or Cl;
$R^3$ is a thiophenyl, naphthyl, or phenyl group, the phenyl group being optionally substituted with one or more substituents selected from the group consisting of $C_{1-4}$ alkyl, $C_{1-4}$ haloalkyl, $C_{1-4}$ alkoxy, methylenedioxy and halogen; and
$R^4$ is H or trifluoromethyl.

5 Claims, No Drawings

ANTIFUNGAL AZOLE DERIVATIVES HAVING A FLUORINATED VINYL GROUP AND PROCESS FOR PREPARING SAME

CROSS REFERENCE TO RELATED APPLICATION

This application is a continuation of International Application PCT/KR 00/00030, with an international filing date of Jan. 18, 2000, now abandoned.

1. Field of the Invention

The present invention relates to novel antifungal azole derivatives having a fluorinated vinyl group, a process for preparing same and an antifungal composition containing same as an active ingredient.

2. Description of the Prior Art

A number of antifungal compounds have been developed for treating diseases caused by fungal infection and examples by currently available antifungal drugs include such azole derivatives as Fluconazole of Pfizer (GB Pat. No. 2,099,818, U.S. Pat. No. 4,404,216), Itraconazole of Janssen (U.S. Pat. No. 4,267,179, EP Patent Publication No. 6,711) and Voriconazole of Pfizer (EP Patent Publication No. 440,372, U.S. Pat. No. 5,278.175).

However, a long-term use of the above drugs may cause side effects such as liver damage and there has emerged a renewed interest in developing a more active and less toxic antifungal drug, as an ever increasing number of people are afflicted with such diseases as AIDS (acquired immune deficiency syndrome), cancer and diabetes, and become vulnerable to fungal infection.

Recently, a number of new azole derivatives have been developed by Janssen (see German Patent No. 2,804,096, U.S. Pat. Nos. 4,144,346 and 4,223,036, and PCT Publication No. WO95/08,993), Schering (see PCT Publication No. WO95/17,407 and WO93/09,114), Takeda(see EP Publication No. 421,210) and YuhanCorporation(see PCT Publication No. WO95/025,107) however, these antifungal compounds exhibit lower antifungal activities and narrower antifungal spectra in comparison with the conventional drugs.

The present inventors have endeavored to develop compounds having high antifungal activity against a wide spectrum of pathogenic fungi; and have unexpectedly found that a new class of azole derivatives having a fluorinated vinyl group exhibit excellent antifungal activities and low toxicity.

SUMMARY OF THE INVENTION

Accordingly, it is aprimary object of the present invention to provide a novel compound which is superior to the conventional antifungal drugs in antifungal activity against a wide spectrum of pathogenic fungi including *Candida albicans*, Torulopsis, Cryptoccocus, Aspergillus, Trichophyton and Fluconazole-resistant *Candida alhicans*, and also in toxicity.

It is another object of the present invention to provide a process for the preparation of said compound.

It is a further object of the present invention to provide an antifungal composition containing said compound.

In accordance with one aspect of the present invention, there is provided a novel azole derivative of formula (I) or a pharmaceutically acceptable salt thereof:

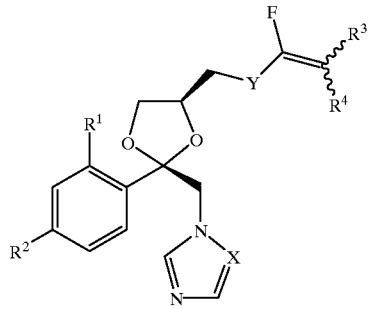

wherein:

X is CH or N;

Y is O, $R^1$ and $R^2$ are each independently F or Cl;

$R^3$ is a thiophenyl, naphthyl, or phenyl group, the phenyl group being optionally substituted with one or more substituents selected from the group consisting of $C_{1-4}$ alkyl, $C_{1-4}$ haloalkyl, $C_{1-4}$ alkoxy, methylenedioxy and halogen; and $R^4$ is H or trifluoromethyl.

DETAILED DESCRIPTION OF THE INVENTION

Among the compounds of the present invention, preferred are those wherein YisO; $R^3$ isaphenyl groupoptionally substituted with one or more substituents selected from the group consisting of Cl, F and Br.

Further, another preferred are those wherein X is CH; Y is O; $R^3$ is methylphenyl; and $R^4$ is H.

The novel azole derivatives substituted carrying a fluorinated vinyl group of formula (I) of the present invention may be prepared by a process which comprises reacting a compound of formula (II) with a fluorinated vinyl compound of formula (III) in the presence of a base as shown in Reaction Scheme 1.

Reaction Scheme 1

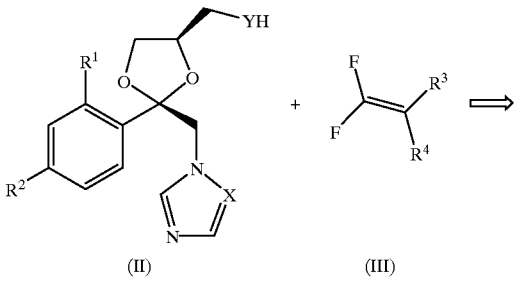

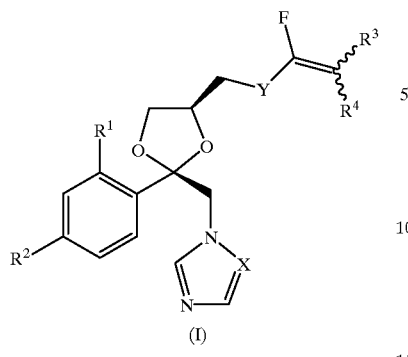

(I)

wherein, X, Y, $R^1$, $R^2$, $R^3$ and $R^4$ have the same meanings as defined in formula (I).

In the above reaction, the compounds of formulae (II) and (III) may be used in equimolar amounts, and the base, in 1 to 2 molar amount.

Further, the solvent which can be used in the present invention includes a typical organic solvent, e.g., benzene, toluene, tetrahydrofuran, acetone, acetonitrile, dichloromethane, dimethylformamide and dimethylsulfoxide and it also includes an organic solvent mixed with water.

The base which can be used in the present invention includes an inorganic base (e.g.: sodium hydride, potassium hydride, potassium t-butoxide, sodium hydroxide, potassium hydroxide, sodium carbonate and potassium carbonate) and an organic base (e.g.: triethylamine and pyridine).

The reaction temperature may range from a room temperature to 100° C. and the progress of the reaction is conveniently followed by measuring the disappearance of the compound of formula (II) with thin layer chromatography (TLC).

The compound of formula (II) is represented by the compounds of formulae (II-a), (II-b) and (II-c) depending on the definition of the substituent Y.

(II-a)

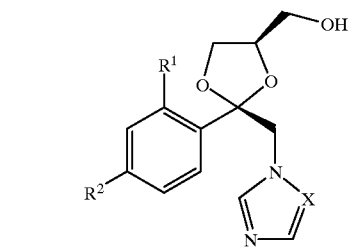

(II-b)

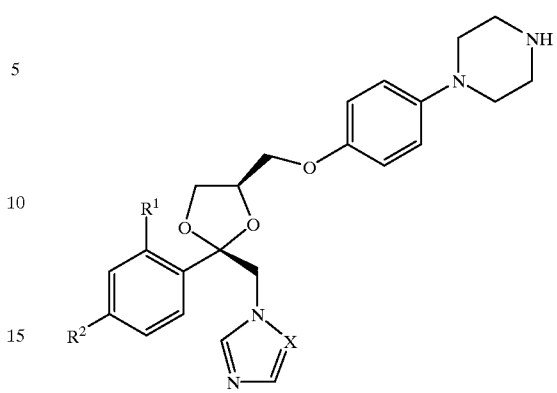

(II-c)

wherein, X, $R^1$ and $R^2$ have the same meanings as defined above.

A compound of formula (II-a) may be prepared by a conventional method(see Heeres, J. et al., *J. Med. Chem.*, 22(8), 1003(1979)) as shown in Reaction Scheme 2:

Reaction Scheme 2

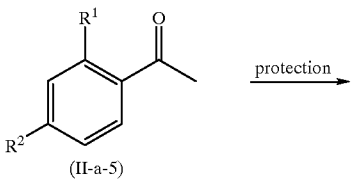

(II-a-5)

protection

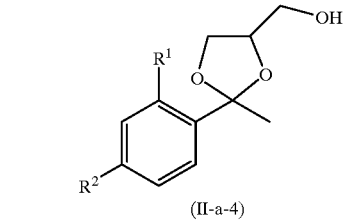

(II-a-4)

bromination

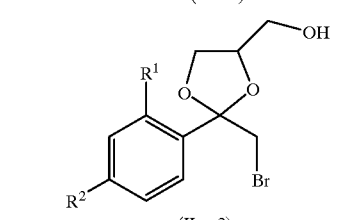

(II-a-3)

benzoylation
recrystallization

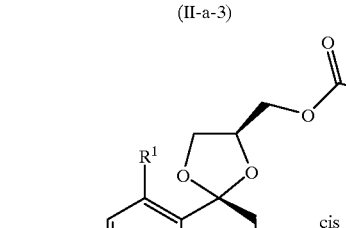

cis

+

(II-a-2)

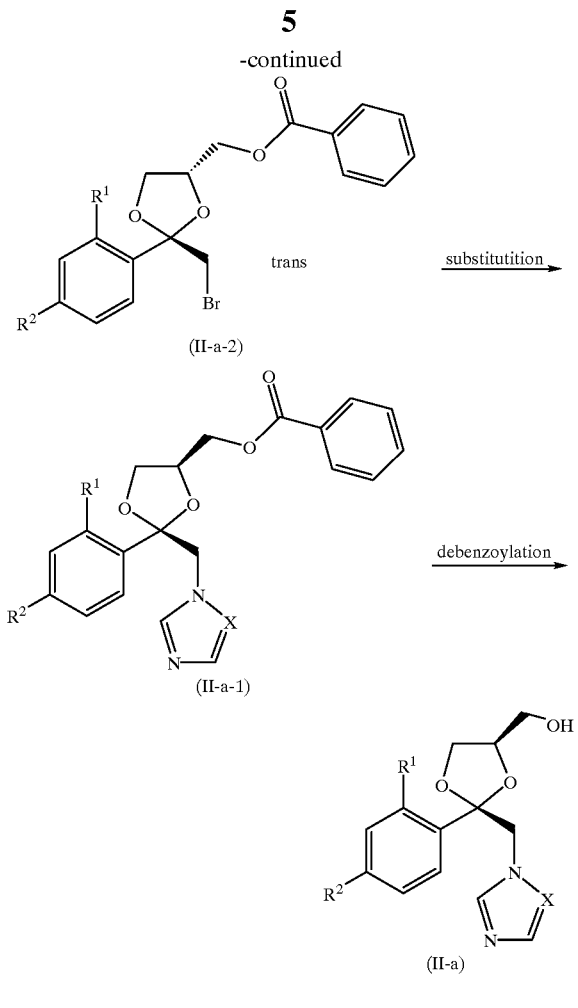

wherein, X, $R^1$ and $R^2$ have the same meanings as defined above.

In Reaction Scheme 2, i) the carbonyl group of a compound of formula (II-a-5) is protected to form a compound of formula (II-a-4); ii) the compound of formula (II-a-4) is brominated to form a compound of formula (II-a-3) (see Levene, P. A., *Org. Syn. Coll.*, 2, 88 (1943)); the compound of formula (II-a-3) is benzoylated and recrystallized to form a compound of formula (II-a-2) (see Wheeler, T. S., *Org. Syn. Coll.*, 4, 478(1943), and Szeja, W., *Synthesis.*, 821 (1979)); and the compound of formula (II-a-2) is subjected to a substitution reaction to form a compound of formula (II-a-1), which is, in turn, debenzoylated to form a compound of (II-a)(see Mashimo, K. et al., *Tetrahedron*, 26, 803 (1970)).

Since the compound of formula (II-a) has two chiral carbons, it is obtained as a mixture of four stereoisomers, a cis- and trans-type diastereomers each of which is composed of two enantiomers. In the present invention, the cis type diastereomer is separated in one of the subsequent reaction steps to form a compound of formula (II-a).

For example, 2-bromomethyl-2-(2,4-dichlorophenyl)-4-phenylcarbonyloxymethyl-1,3-dioxolane obtained from the reaction of 2-bromomethyl-2-(2,4-dichlorophenyl)-1,3-dioxolan-2-yl methanol (i.e., the compound of formula (II-a-3) wherein $R^1$ and $R^2$ are Cl) with benzoyl chloride is subjected to recrystallization to separate the cis diastereomer having a melting point of 115° C. in the form of a colorless crystal which is used in the next reaction, as in Reaction Scheme 2.

Further, in case of 2-bromomethyl-2-(2,4-difluorophenyl)-4-phenylcarbonyloxymethyl-1,3-dioxolane obtained from the reaction of 2-bromomethyl-2-(2,4-difluorophenyl)-1,3-dioxolan-2-yl methanol(i.e., the compound of formula (II-a-3) wherein $R^1$ and $R^2$ are F) with benzoyl chloride, it is converted into 2-(2,4-difluorophenyl)-2-(1H-1-imidazolyl-methyl)-4-phenylcarbonyloxymethyl-1,3-dioxolane, which is subjected to recrystallization to separate the cis form(i.e., a compound of formula (II-a-1)) having a melting point of 136° C., as shown in the following Reaction Scheme 3.

Reaction Scheme 3

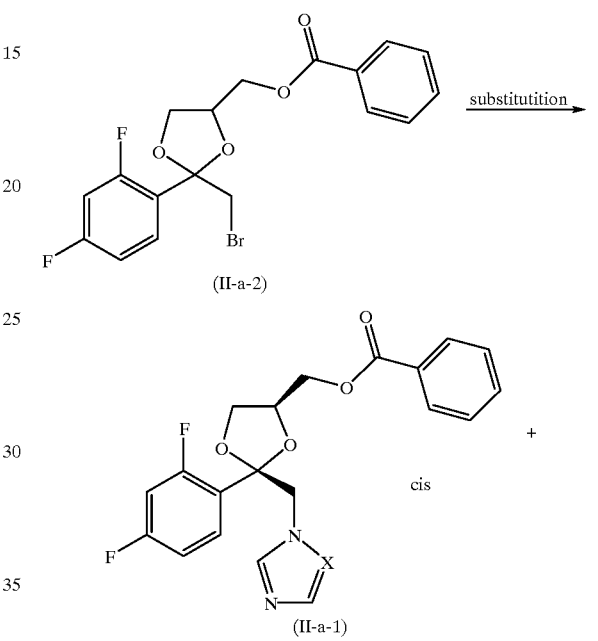

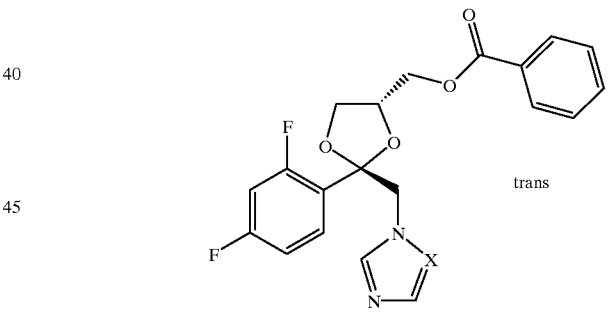

wherein, X has the same meaning as defined above.

In the present invention, cis isomers of formulae (II-a) and (II-b) and (II-c) are used.

A compound of formula (II-b) may be prepared by the method described in Heeres, J. et al., *J. Med. Chem.*, 26 (4). 611 (1983), i.e., by the process shown in Reaction Scheme 4 which comprises the steps of conducting a sulfonation reaction of a compound of formula (II-a) (see Furst A. et al., *Helv. Chem. Acta*. 30. 1454 (1947)), substitution and debenzylation (see Heathcock, C. H. et al., *J. Amer. Chem. Soc.*, 93. 1746 (1971)).

Reaction Scheme 4

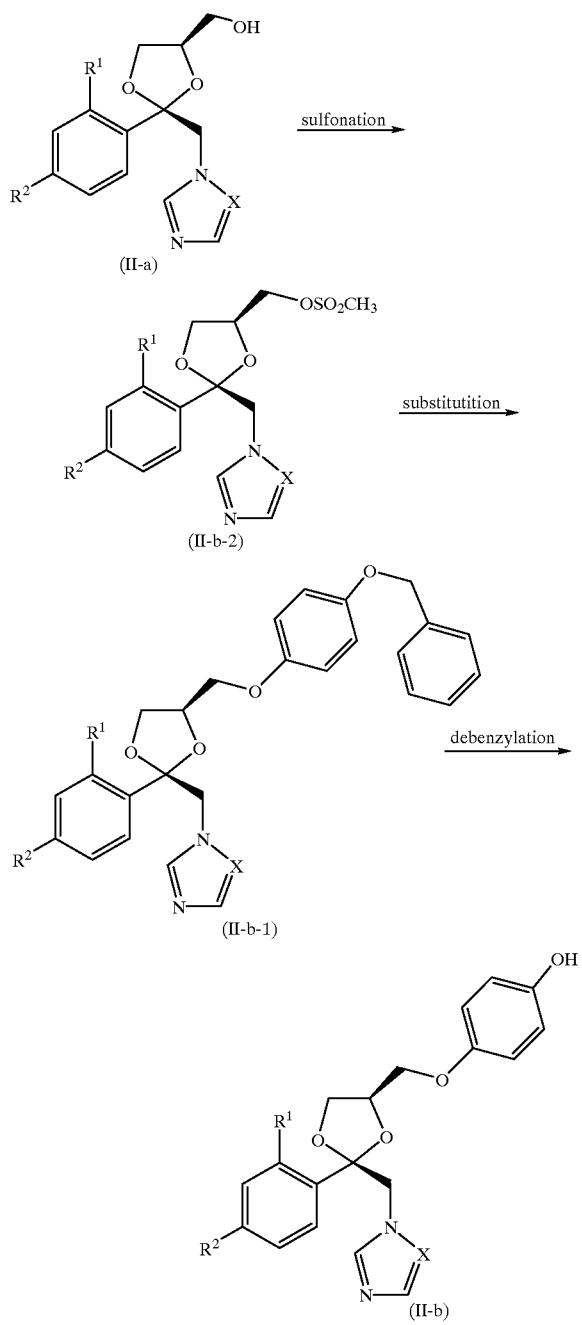

wherein, X, $R^1$ and $R^2$ have the same meanings as defined above.

An amine of formula (II-c) which can be used as a starting material in preparing the compound of formula (I) may be prepared by the method described in Heeres, J. et al., *J. Med. Chem.*, 27 (7). 894 (1984), i.e., by the process shown in Reaction Scheme 5 which comprises the steps of conducting a substitution reaction of a compound of formula (II-b-2) to form a compound of formula (II-c-1) and hydrolysis of the compound of formula (II-c-1).

Reaction Scheme 5

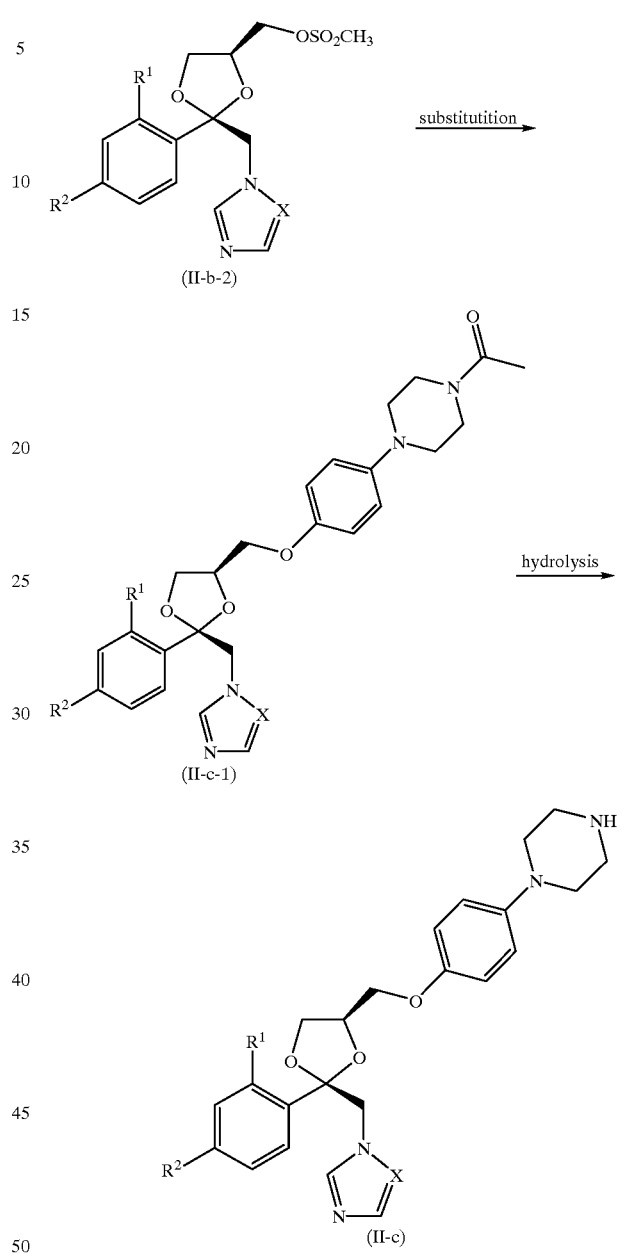

wherein, X, $R^1$ and R2 have the same meanings as defined above.

The fluorinated vinyl compound of formula (III) is represented by the compounds of formulae (III-a) and (III-b) depending on the definition of the substituent $R^4$.

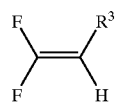

(III-a)

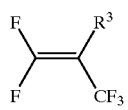

(III-b)

wherein, $R^3$ has the same meaning as defined in formula (I) above.

Among the fluorinated vinyl compound of formula (III), the compound of (III-a) wherein $R^4$ is H may be prepared by a conventional method (see Herkes, F. E. et al., *J. Org. Chem.*, 32, 1311 (1967)), e.g., by the process shown in Reaction Scheme 6 which comprises the steps of conducting a Grignard reaction of the halogenated compound of formula (III-a-4), reduction, chlorination and dehalogenation. Further, the compound of (III-b) wherein $R^4$ is $CF_3$ may be prepared by a Wittig reaction using a ketone of formula (III-a-3) as a starting material as shown in Reaction Scheme 6 (see Herkes, F. E. et al., *J. Org. Chem.*, 48, 917 (1983)).

$R^1$, $R^2$ and $R^3$ have the same meanings as defined above, the compound is a Z isomer when $R^4$ is H, while the compound is an E isomer when $R^4$ is $CF_3$.

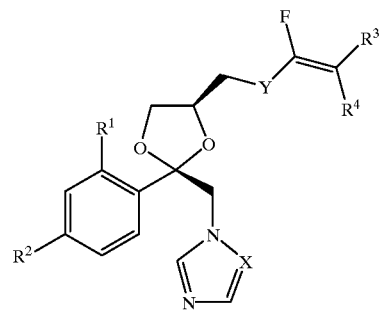

(I-2)

Further, in case of the compound of formula (I-3) wherein the chiral carbons have the configuration of (2S, 4R) and X, Y, $R^1$, $R^2$ and $R^3$ have the same meanings as defined above, Reaction Scheme 6

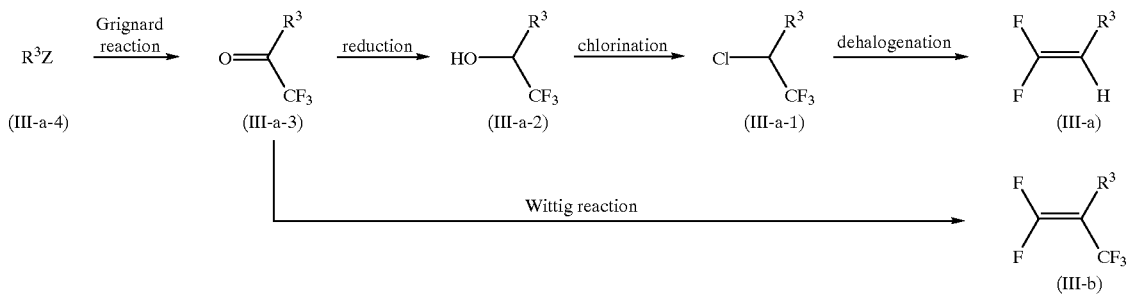

wherein, $R^3$ has the same meaning as defined in formula (I) above and Z is a halogen such as Br and Cl.

The compound of formula (I) of the present invention has a double bond in its vinyl moiety, and thus, Z(zusammen) and E(entgegen) isomers may co-exist. Further, due to the chiral carbons at 2- and 4-position of the dioxolane ring, the compound of formula (I) may exist in the form of either (2R,4S) or (2S,4R) stereoisomers.

In case of the compound of formula (I-1) wherein the chiral carbons have the configuration of (2R,4S) and X, Y, $R^1$, $R^2$ and $R^3$ have the same meanings as defined above, the compound is an E isomer when $R^4$ is H, while the compound is a Z isomer when $R^4$ is $CF_3$.

the compound is an E isomer when $R^4$ is H, while the compound is a Z isomer when $R^4$ is $CF_3$.

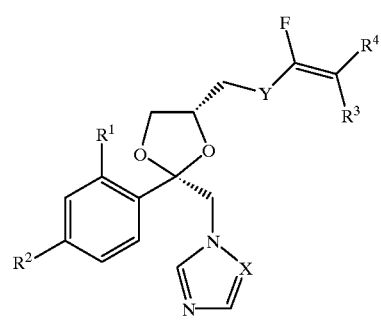

(I-3)

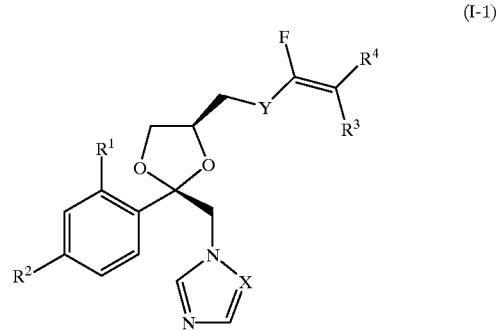

(I-1)

In case of the compound of formula (I-2) wherein the chiral carbons have the configuration of (2R,4S) and X, Y, In case of the compound of formula (I-4) wherein the chiral carbons have the configuration of (2S,4R) and X, Y, $R^1$, $R^2$ and $R^3$ have the same meanings as defined above, the compound is a Z isomer when $R^4$ is H, while the compound is an E isomer when $R^4$ is $CF_3$.

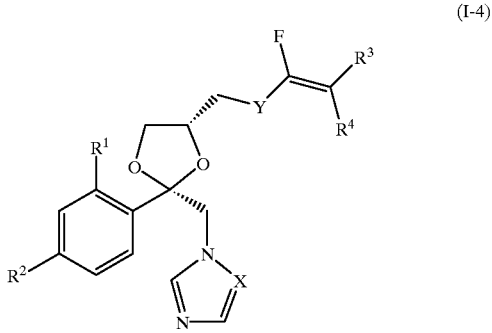

(I-4)

In practicing the present invention, the compound of formula (I) wherein $R^4$ is H is obtained mainly in the form of a mixture of E-isomers((I-1) and (I-3)), Z-isomers((I-2) and (I-4)] being a minor product. When $R^4$ is $CF_3$, the reaction mixture contains mainly Z-isomers((I-1) and (I-3)), with a minor amount of E-isomers((I-2) and (I-4)].

The compound of formula (I) exhibit excellent antifungal activity against a wide spectrum of pathogenic fungi including *Candida albicans*, Torulopsis, Cryptoccocus, Asperqillus, Trichoohyton and Fluconazole-resistant *Candida albicans*, as well as fungicidal activities.

The present invention also includes within its scope an antifungal composition comprising one or more of the novel azole derivatives of formula (I) as an active ingredient, in association with pharmaceutically acceptable carriers, excipients or other additives, if necessary.

The pharmaceutical compositions of the present invention may be formulated for administration orally or by injection. The composition for oral administration may take various forms such as tablets and gelatin capsules, which may contain conventional additives such as a diluent (e.g., lactose, dextrose, sucrose, mannitol, sorbitol, cellulose and/or glycine), a lubricant (e.g., silica, talc, stearic acid or its magnesium and calcium salts and polyethylene glycol). In the tablet form, the composition may further comprise a binder (e.g., magnesium aluminum silicate, starch paste, gelatin, tragacanth, methyl cellulose, sodium carboxymethyl cellulose and polyvinyl picolidine) and optionally a disintegrant (e.g., starch, agar and alginic acid or its sodium salt), absorbent, colorant, flavor and sweetener. The composition for injection may be an isotonic solution or a suspension. The inventive pharmaceutical composition may be administered daily. A typical daily dose of the active ingredient ranges from about 1 to 1000 mg/kg, preferably 1 to 200 mg/kg, and can be administered in a single dose or in divided doses, preferably 1 to 3 doses. However, it should be understood that the amount of the active ingredient actually administered should be determined in light of various relevant factors including the condition to be treated, the chosen route of administration, the age and weight of the individual patient, and the severity of the patient's symptoms; and, therefore, the dosage suggested above should not be construed to limit the scope of the invention in any way.

The compounds of the present invention may be administered simultaneously with one or more other anti-bacterial agent, analgesic, anti-cancer agent and anti-viral agent and the oral formulations and injections can be used simultaneously.

The following Preparation and Examples are given for the purpose of illustration only and are not intended to limit the scope of the invention.

In Examples, the compounds obtained are mixtures of E-and Z-isomers, which may be identified through $^1$H-NMR analysis and both isomers are shown in NMR data.

PREPARATION 1

Preparation of cis-2-(2,4-dichlorophenyl)-2-(1H-1-imidazolylmethyl)-1,3-dioxolan-4-yl methanol(II-1) [(2R,4S) or (2S,4R)]

Step 1: Preparation of 2-bromomethyl-2-(2,4-dichlorophenyl)-1,3-dioxolan-4-yl methanol(II-a-3)

In a reactor equipped with a Dean-Stark trap, 37.8 g of 2,4-dichloroacetophenone(II-a-5) (0.2 mol) and 27.6 g of glycerol (0.3 mol) were added to a mixture of 80 ml of benzene and 40 ml of n-butanol, and then, 1.2 g of p-toluenesulfonic acid(hydrate) was added thereto. The mixture was refluxed for 24 hours. After removing water from the reaction mixture, 12.37 ml of bromine (0.24 mol) was added dropwise over 2 hours while maintaining the temperature at below 40° C. The reaction mixture was stirred at room temperature for 1 hour and the solvent was removed under a reduced pressure.

Then, the residue was dissolved in dichloromethane and the solution was washed with 6N NaOH. The organic layer was separated, dried on the anhydrous magnesium sulfate, filtered, and the solvent was removed under a reduced pressure. The residue thus obtained was subjected to column chromatography using a mixture of n-hexane and ethyl acetate (4:1) as an eluent to obtain 58.8 g (yield 86%) of the title compound as a colorless liquid.

$^1$H-NMR(CDCl$_3$, TMS) δ (ppm): 7.67–7.59 (m, 1H), 7.42–7.41 (d, 1H), 7.29–7.23 (m, 1H), 4.60–4.26 (m, 2H), 4.19–3.50(m, 5H), 2.40 (br.s, 1H); MS(m/e): 342 (M$^+$, 7.7), 268 (8.5), 246 (100), 173 (75).

Step 2: Preparation of 2-bromomethyl-2-(2,4-dichlorophenyl)-4-phenylcarbonyloxymethyl-1,3-dioxolane(II-a-2)

51.27 g (0.15 mol) of the compound obtained in Step 1 was mixed with 100 ml of dry pyridine, 22.14 g of benzoyl chloride (0.1575 mol) was added thereto dropwise at below 5° C. and stirred for 3 hours. After adding 200 ml of chloroform, reaction mixture was washed three times with 100 ml portion of 6N HCl. The organic layer was separated, dried over anhydrous magnesium sulfate, filtered, and the solvent was removed under a reduced pressure to give a white solid.

The white solid thus obtained contained four stereomers, i.e., cis- and trans-diastereomers each of which is composed of two enantiomers. The cis product was separated by recrystallization from methanol and further recrystallized twice or three times to obtain 33 g of pure cis-2-bromomethyl-2-(2,4-dichlorophenyl)-4-phenylcarbonyloxymethyl-1,3-dioxolane(II-a-2) (yield 49.5 %) (m.p.: 115° C.).

$^1$H-NMR (CDCl$_3$, TMS) δ (ppm): 8.09 (d, 1H), 8.07 (d, 1H) 7.66–7.57 (m, 2H), 7.48–7.42 (m, 3H), 7.29–7.26 (m, 1H), 4.57–4.55 (m, 2H), 4.43 (m, 1H), 4.13–4.11 (m, 1H), 4.04–4.01 (m, 1H), 3.96–3.85 (m, 2H). MS (m/e): 446 (M$^+$, 0.02), 385 (0.16), 351 (60), 172 (49), 105 (100), 77 (42).

Step 3: Preparation of cis-2-(2,4-dichlorophenyl)-2-(1H-1-imidazolylmethyl)-4-phenylcarbonyloxymethyl-1,3-dioxolane(II-a-1)[(2R,4S), (2S,4R)

10.2 g of imidazole (0.15 mol) and 22.25 g (0.05 mol) of the compound obtained in Step 2 were added to 100 ml of N,N-dimethylacetamide (DMA) and the mixture was refluxed for four days. Then, the mixture was cooled and 100 ml of water was added thereto and extracted three times with ethyl ether. The combined organic layer was dried and the solvent was removed.

The brown liquid residue thus obtained was subjected to column chromatography using a mixture of n-hexane and ethyl acetate (1:1) as an eluent to obtain 14.73 g (yield 68%) of the title compound as a white crystal (m.p.:172° C.).

¹H-NMR (CDCl₃, TMS) δ (ppm): 8.06–8.01 (m, 2H), 7.62–7.44 (m, 6H), 7.26–7.20 (m, 1H), 6.97 (s, 2H), 4.57–4.31 (m, 3H), 4.21–4.07 (m, 2H), 3.96–3.88 (mt, 1H), 3.73–3.66 (m, 1H); MS (m/e): 432 (M⁺, 3.2), 351 (70), 289 (46), 173 (100), 105 (99), 77 (33), 43 (76).

Step 4: Preparation of cis-2-(2,4-dichlorophenyl)-2-(1H-1-imidazolylmethyl)-1,3-dioxolan-4-ylmethanol(II-a)[(2R,4S), (2S,4R)]

13.0 g of the compound (0.03 mol) obtained in Step 3 was mixed with 50 ml of 1,4-dioxane, 10 ml of aqueous 50% sodium hydroxide was added thereto and the mixture was refluxed for 30 minutes.

Then, the mixture was cooled and 100 ml of water was added thereto. The mixture was extracted three times with chloroform and the combined organic layer was dried. The solvent was removed to obtain a brown liquid residue.

The residue thus obtained was subjected to column chromatography using a mixture of ethyl acetate and methanol (9:1) as an eluent to obtain 8.10 g (yield 82%) of the title compound(m.p.:136° C.).

¹H-NMR (CDCl₃, TMS) δ (ppm): 7.60 (s, 1H), 7.59 (d, 1H, J=8.4 Hz), 7.46 (d, 1H, J=2.1 Hz), 7.26 (dd, 1H, J=8.4 Hz, 2.1 Hz), 7.02 (s, 1H), 7.00 (s, 1H), 4.45 (dd, 2H, J=56.0 Hz, 14.7 Hz), 4.12 (p, 1H, J=5.6 Hz), 3.81 (dd, 1H, J=7.05 Hz, 8.0 Hz), 3.65 (dd, 1H, J=5.75 Hz, 8.0 Hz), 3.40 (dd, 1H, J=4.3 Hz, 11.8 Hz), 3.31 (dd, 1H, J=5.1 Hz, 11.8 Hz), 2.32 (br. s, 1H); MS(m/e): 329 (M⁺, 9.5), 247 (85), 173 (100), 57 (35)

PREPARATION 2

Preparation of cis-2-(2,4-difluorophenyl)-2-(1H-1-imidazolylmethyl)-1,3-dioxolan-4-yl methanol(II-a) [(2R,4S) or (2S,4R)]

Step 1: Preparation of 2-bromomethyl-2-(2,4-difluorophenyl)-1,3-dioxolan-4-yl methanol(II-a-3)

The procedure of Step 1 of Example 1 was repeated except that 31.2 g of 2,4-difluoroacetophenone(II-a-5)(0.2 mol) was used in place of the 2,4-dichloroacetophenone. The residue was subjected to column chromatography using a mixture of n-hexane and ethyl acetate (4:1) as an eluent to obtain 50.6 g (yield 82%) of the title compound as a colorless liquid.

¹H-NMR (CDCl₃, TMS) δ (ppm): 7.62–7.46 (m, 1H), 6.92–6.76 (m, 2H), 4.58–3.50 (m, 7H), 2.47–2.02 (m, 1H); MS (m/e): 309 (M⁺, 2), 235 (10), 215 (100), 141 (47), 57 (41).

Step 2: Preparation of 2-bromomethyl-2-(2,4-difluorophenyl)-4-phenylcarbonyloxymethyl-1,3-dioxolane(II-a-2)

The procedure of Step 2 of Example 1 was repeated except that 46.34 g of 2-bromomethyl-2-(2,4-difluorophenyl)-1,3-dioxolan-4-yl methanol(II-a-3) (0.15 mol) and benzoyl chloride were used to obtain a brown liquid containing 2-bromomethyl-2-(2,4-difluoro-phenyl)-4-phenylcarbonyl-oxymethyl-1,3-dioxolane(II-a-2).

The resulting brown liquid, a mixture of four stereomers, i.e., cis- and trans-diastereomers each of which is composed of two enantiomers was subjected to column chromatography using a mixture of n-hexane and ethyl acetate (4:1) as an eluent to obtain 55.2 g (yield 89%) of the title compound as a mixture of isomers.

¹H-NMR (CDCl₃, TMS) δ (ppm): 8.19–8.05 (m, 1H), 7.79–7.32 (m, 5H), 6.94–6.76 (m, 2H), 4.58–3.78 (m, 7H); MS(m/e): 412 (M⁺, 0.2), 319 (100), 141 (50), 105 (97).

Step 3: Preparation of cis-2-(2,4-difluorophenyl)-2-(1H-1-imidazolylmethyl)-4-phenylcarbonyloxymethyl-1,3-dioxolane(II-a-1)[(2R,4S), (2S,4R)]

The procedure of Step 3 of Example 1 was repeated except that 51.6 g of 2-bromomethyl-2-(2,4-difluorophenyl)-4-phenylcarbonyloxymethyl-1,3-dioxolane (II-a-2)(0.125 mol) obtained in Step 2 and 25.5 g of imidazole (0.375 mol) were added to 200 ml of N,N-dimethylacetamide(DMA) to form 2-(2,4-difluorophenyl)-2-(1H-1-imidazolylmethyl)-4-phenylcarbonyloxymethyl-1,3-dioxolane.

The resulting liquid mixture containing cis- and trans-diastereomers was subjected to column chromatography using a mixture of n-hexane and ethyl acetate (1:4) as an eluent to separate the cis product and 21.5 g (yield 43%) of the title compound was obtained as a colorless solid (MP 104° C.).

¹H-NMR (CDCl₃, TMS) δ (ppm): 8.04–8.01 (m, 2H), 7.61–7.57 (m, 1H), 7.52 (s, 1H), 7.49–7.42 (m, 3H), 6.98 (s, 2H), 6.90–6.84 (m, 2H), 4.42–4.35 (m, 3H), 4.16–4.07 (m, 2H), 3.98–3.94 (m, 1H), 3.67–3.63 (m, 1H); MS(m/e): 400 (M⁺, 1.4), 319 (76), 141 (69), 105 (100).

Step 4: Preparation of cis-2-(2,4-difluorophenyl)-2-(1H-1-imidazolylmethyl)-1,3-dioxolan-4-ylmethanol(II-a)[(2R,4S), (2S,4R)]

The procedure of Step 4 of Example 1 was repeated except that 12.0 g of cis 2-(2,4-difluorophenyl)-2-(1H-1-imidazolylmethyl)-4-phenylcarbonyloxymethyl-1,3-dioxolane(II-a-1) was used.

The resulting product was subjected to column chromatography using a mixture of ethyl acetate and methanol (9:1) as an eluent to obtain 7.28 g (yield 82%) of the title compound as a white crystal (m.p.: 136° C.).

¹H-NMR (CDCl₃, TMS) δ (ppm): 7.53–7.44 (m, 2H), 6.97 (s, 2H), 6.90–6.82 (m, 2H), 4.33 (dd, 2H, J=42.43 Hz, 24.45 Hz), 4.14 (p, 1H, J=9.97 Hz), 3.84 (dd, 1H, J=12.34 Hz, 12.33 Hz), 3.59 (dd, 1H, J=13.42 Hz, 9.76 Hz), 3.29 (d, 2H, J=8.99 Hz), 2.05 (br. s, 1H); MS (m/e): 296 (M⁺, 0.2), 265 (5.5), 215 (92), 141 (100)

PREPARATION 3

Preparation of cis-2-(2,4-dichlorophenyl)-2-(1H-1-triazolylmethyl)-1,3-dioxolan-4-yl methanol(II-a) [(2R,4S) or (2S,4R)]

Step 1: Preparation of cis-2-(2,4-dichlorophenyl)-2-(1H-1-triazolylmethyl)-4-phenylcarbonyloxymethyl-1,3-dioxolane (II-a-1)[(2R,4S) , (2S,4R)]

3.454 g of 1,2,4-triazole (0.05mol) and 2.2 g of sodium hydride (NaH, 60%, dispersed in mineral oil) (0.055 mol) were added to 100 ml of dimethylsulfoxide(DMSO). 22.25 g of cis 2-bromomethyl-2-(2,4-difluoro-phenyl)-4-phenylcarbonyl-oxymethyl-1,3-dioxolane(II-a-2) (0.05 mol) was added thereto and the mixture was reacted at 130° C. for 1 day.

After cooling the reaction mixture, 100 ml of water was added thereto and the mixture was extracted three times with dichloromethane. The combined organic layer was dried and the solvent was removed to obtain a brown liquid. The resulting product was subjected to column chromatography using a mixture of n-hexane and ethyl acetate (1:2) as an eluent to obtain 14.73 g (yield 68%) of the title compound. (Yield: 68%)

¹H-NMR (CDCl₃, TMS) δ (ppm): 8.22 (s, 1H), 8.12–8.00 (m, 2H), 7.86 (s, 1H), 7.63–7.42 (m, 4H), 7.28–7.20 (m, 2H), 4.85–4.48 (m, 2H), 4.42–4.31 (m, 1H), 4.28–4.09 (m, 2H), 3.99–3.90 (m, 1H), 3.82–3.74 (m, 1H); MS(m/e): 434 (M⁺, 0.8), 351 (46), 173 (37), 105 (100), 77 (28).

Step 2: Preparation of cis-2-(2,4-dichlorophenyl)-2-(1H-1-triazolylmethyl)-1,3-dioxolan-4-ylmethanol(II-a)[(2R,4S), (2S,4R)]

The procedure of Step 4 of Example 1 was repeated except that 13.0 g of cis 2-(2,4-dichlorophenyl)-2-(1H-1- triazolylmethyl)-4-phenylcarbonyloxymethyl-1,3-dioxolane (II-a-1) was used.

After cooling the reaction mixture, 100 ml of water was added thereto and the mixture was extracted three times with dichloromethane. The combined organic layer was dried and the solvent was removed to obtain a brown liquid, which was subjected to column chromatography using a mixture of ethyl acetate and methanol (9:1) as an eluent to obtain 8.10 g (yield 82%) of the title compound. (m.p.:125° C.)

$^1$H-NMR(CDCl$_3$, TMS) δ (ppm): 8.13 (s, 1H), 7.96 (s, 1H), 7.60–7.56 (m, 1H), 7.49–7.48 (m, 1H), 7.29–7.23 (m, 1H), 4.77 (s, 2H), 4.18–4.10 (m, 1H), 3.90–3.82 (m, 1H), 3.74–3.63 (m, 2H), 3.31–3.21 (m, 1H), 2.63 (br.s, 1H); MS(m/e): 330 (M$^+$, 1.6), 247 (91), 173 (100), 116 (27), 57 (32)

PREPARATION 4

Preparation of cis-2-(2,4-dichlorophenyl)- 2-(1H-1-imidazolylmethyl)-1,3-dioxolan-4-ylmethoxy]phenol (II-b)[(2R,4S) or (2S,4R)]

Step 1: Preparation of cis-2-(2,4-dichlorophenyl)-2-(1H-1-triazolylmethyl)-1,3-dioxolan-4-ylmethyl methane sulfonate(II-b-2)[(2R,4S), (2S,4R)]

6.58 g of cis-2-(2,4-dichlorophenyl)-2-(1H-1-imidazolylmethyl)-1,3-dioxolan-4-ylmethanol(II-a) (0.02 mol) and 20ml of pyridine were mixed and 2.52 g(0.022 mol) of methanesulfonylchloride was added dropwise thereto, and the mixture was stirred at room temperature for 5 hours. The solvent was removed and the resulting solid was recrystallized to obtain 7.97 g of the title compound (Yield: 98%) (m.p.: 78° C.)

$^1$H-NMR (CDCl$_3$, TMS) δ (ppm): 7.58–7.47 (m, 3H), 7.30–7.25 (m, 1H), 7.03–7.01 (m, 2H), 4.47 (dd, 2H, J=22.8 Hz, 14.7 Hz), 4.32 (p, 1H, J=5.49 Hz), 3.90–3.82 (m, 2H), 3.75–3.61 (m, 2H), 3.04 (s, 3H); MS (m/e): 407 (M$^+$, 0.1), 327 (65), 325 (78), 173 (100), 57 (26).

Step 2: Preparation of cis-4-(benzyloxyphenoxymethyl)-2-(2,4-dichlorophenyl)-1,3-dioxolan-2-yl-(1H-1-imidazolyl)methane(II-b-1)[(2R,4S), (2S,4R)]

3 g of 4-(benzyloxy)phenol(0.015 mol) was mixed with 20 ml of acetonitrile under a N$_2$ atmosphere and 0.6 g of sodium hydride (NaH, 60%, dispersed in mineral oil) (0.015 mol) was added thereto. After adding 6.1 g of cis-2-(2,4-dichlorophenyl)-2-(1H-1-imidazolylmethyl)-1,3-dioxolan-4-ylmethyl methanesulfonate(II-b-2) to the reactants, the mixture was refluxed for 24 hours.

After cooling the reaction mixture, 100 ml of water was added thereto and the mixture was extracted with ethyl acetate. The organic layer was dried over anhydrous magnesium sulfate, filtered, and the solvent was removed.

The resulting product was subjected to column chromatography using ethyl acetate as an eluent to obtain 6.8 g (yield 89%) of the title compound as a white crystal. (m.p.: 118° C.)

$^1$H-NMR (CDCl$_3$, TMS) δ (ppm): 7.60–7.23 (m, 9H), 6.99–6.85 (m, 4H), 6.78–6.72 (m, 2H), 5.01 (s, 2H), 4.55–4.30 (m, 3H), 3.90–3.83 (m, 1H), 3.76–3.66 (m, 2H), 3.34–3.26 (m, 1H); MS(m/e): 510 (M$^+$, 20), 429 (1.5), 172 (36), 91 (100), 82 (8).

Step 3: Preparation of 4-[cis-2-(2,4-dichlorophenyl)-2-(1H-1-imidazolylmethyl)-1,3-dioxolan-4-ylmethoxy]phenol(II-b)[(2R,4S), (2S,4R)]

Charged in a hydrogenation reactor were 20 ml of dry ethyl acetate, 5.1 g of cis-4-(benzyloxyphenoxymethyl)-2-(2,4-dichloro-phenyl)-1,3-dioxolan-2-yl-(1H-1-imidazolyl)methane(II-b-1)(0.010 mol) and 100 mg of 10% palladium on carbon(Pd(C)). H$_2$ was introduced therein, and the mixture was stirred for 4 hours.

The reaction mixture was filtered to remove the catalyst and the solvent was evaporated. The resulting solid product was subjected to column chromatography using ethyl acetate as an eluent to obtain 2.95 g (yield 70%) of the title compound as a white crystal. (m.p.: 143° C.)

$^1$H-NMR (CDCl$_3$, TMS) δ (ppm): 8.99 (br. s, 1H), 7.48–6.67 (m, 10H), 4.37–4.21 (m, 3H), 3.90–3.78 (m, 1H), 3.62–3.50 (m, 2H), 3.46–3.35 (m, 1H); MS(m/e): 420 (M$^+$, 12), 386 (41), 305 (11), 210 (17), 149 (43), 82 (100).

PREPARATION 5

Preparation of 4-[cis-2-(2,4-difluoro-phenyl)-2-(1H-1-imidazolylmethyl)-1,3-dioxolan-4-ylmethoxy]phenol(II-b)[(2R,4S) or (2S,4R)]

Step 1: Preparation of cis-2-(2,4-difluorophenyl)-2-(1H-1-imidazolylmethyl)-1,3-dioxolan-4-ylmethylmethanesulfonate(II-b-2)[(2R,4S), (2S,4R)]

The procedure of Step 1 of Preparation 4 was repeated except that 5.92 g of cis-2-(2,4-difluorophenyl)-2-(1H-1-imidazolylmethyl)-1,3-dioxolan-4-ylmethanol(II-a)(0.02 mol) was used.

After removing the solvent, the resulting liquid product was subjected to column chromatography using a mixture of n-hexane and ethyl acetate (1:4) an eluent to obtain 6.88 9 (yield 92%) of the title compound.

$^1$H-NMR (CDCl$_3$, TMS) δ (ppm): 7.50–7.44 (m, 2H), 7.00–6.98 (m, 2H), 6.92–6.82 (m, 2H), 4.42–4.26 (m, 3H), 3.91–3.76 (m, 2H), 3.69–3.56 (m, 2H), 3.01 (s, 3H); MS(m/e): 375 (M$^+$+1, 2.4), 293 (100), 141 (84).

Step 2: Preparation of cis-4-(benzyloxyphenoxymethyl)-2-(2,4-difluorophenyl)-1,3-dioxolan-2-yl-(1H-1-imidazolyl)methane(II-b-1)[(2R,4S), (2S,4R)]

The procedure of Step 2 of Preparation 4 was repeated except that 5.6 g of cis-2-(2,4-difluorophenyl)-2-(1H-1-imidazolylmethyl)-1,3-dioxolan-4-ylmethylmethanesulfonate(II-b-2) obtained in Step 1 was used.

After removing the solvent, the resulting solid product was subjected to column chromatography using ethyl acetate as an eluent to obtain 5.52 g (yield 77%) of the title compound as a white crystal. (yield 77%) (m.p.: 114° C.)

$^1$H-NMR(CDCl$_3$, TMS) δ (ppm): 7.56–7.25 (m, 7H), 6.99–6.71 (m, 8H), 4.99 (s, 2H), 4.43–4.25 (m, 3H), 3.94–3.86 (m, 1H), 3.73–3.63 (m, 2H), 3.29–3.20 (m, 1H); MS (m/e): 478 (M$^+$, 28), 372 (5), 172 (33), 141 (31), 91 (100).

Step 3 : Preparation of 4-[cis-2-(2,4-fluorophenyl)-2-(1H-1-imidazolylmethyl)-1,3-dioxolan-4-ylmethoxy]phenol(II-b) [(2R,4S), (2S,4R)]

The procedure of Step 3 of Preparation 4 was repeated except that 20 ml of ethyl alcohol and 4.78 g of cis-4-(benzyloxyphenoxymethyl)-2-(2,4-difluorophenyl)-1,3-dioxolan-2-yl-(1H-1-imidazolyl)methane(II-b-1) were used.

The reaction mixture was filtered to remove the catalyst and the solvent was evaporated. The resulting solid product was recrystallized from ethyl alcohol to obtain 2.64 g (yield 68%) of the title compound as a white crystal.(m.p.: 211° C.)

$^1$H-NMR (CDCl$_3$, TMS) δ (ppm): 8.97 (br.s, 1H), 7.51–7.42 (m, 2H), 7.38–7.26 (m, 1H), 7.14–7.01 (m, 2H), 6.81 (s, 1H), 6.69–6.63 (m, 4H), 4.44 (s, 2H), 4.39 (m, 1H), 3.95–3.87 (m, 1H), 3.66–3.50 (m, 2H), 3.48–3.42 (m, 1H); MS(m/e): 388 (M$^+$, 32), 307 (4), 141 (73), 82 (100).

PREPARATION 6

Preparation of 4-[cis-2-(2,4-dichloro-phenyl)-2-(1H-1-triazolylmethyl)-1,3-dioxolan-4-ylmethyoxy]-phenol(II-b)[(2R,4S) or (2S,4R)]

Step 1: Preparation of cis-2-(2,4-dichlorophenyl)-2-(1H-1-triazolylmethyl)-1,3-dioxolan-4-ylmethylmethanesulfonate (II-b-2)[(2R,4S), (2S,4R)]

The procedure of Step 1 of Preparation 4 was repeated except that 6.60 g of cis-2-(2,4-dichlorophenyl)-2-(1H-1-triazolylmethyl)-1,3-dioxolan-4-ylmethanol(II-a) (0.02 mol) was used.

The resulting solid product was recrystallized from benzene to obtain 7.75 g (yield 95%) of the title compound as a white crystal (Yield: 95%) (m.p.: 100° C.).

$^1$H-NMR (CDCl$_3$, TMS) δ: 8.23 (s, 1H), 7.89 (s, 1H), 7.55–7.46 (m, 2H), 7.28–7.23 (m, 1H), 4.87–4.4.73 (m, 2H), 4.38–4.29 (m, 1H), 3.99–3.86 (m, 3H), 3.78–3.70 (m, 1H), 3.10 (s, 3H); MS(m/e): 408 (M$^+$+1, 1.5), 372 (0.9), 325 (100), 173 (94), 79 (26), 57 (42).

Step 2: Preparation of cis-4-(benzyloxyphenoxymethyl)-2-(2,4-dichlorophenyl)-1,3-dioxolan-2-yl-(1H-1-triazolyl)-methane(II-b-1)[(2R,4s), (2S,4R)]

The procedure of Step 2 of Preparation 4 was repeated except that 6.12 g of cis-2-(2,4-dichlorophenyl)-2-(1H-1-triazolylmethyl)-1,3-dioxolan-4-ylmethylmethanesulfonate (II-b-2) obtained in Step 1 was used.

After removing the solvent, the resulting solid product was recrystallized from methanol to obtain 6.37 g (yield 83%) of the title compound as a white crystal.(yield 83%) (m.p.: 126° C.)

$^1$H-NMR CDCl$_3$, TMS) δ (ppm): 8.20 (s, 1H) , 7.89 (s, 1H), 7.59–7.54 (m, 1H), 7.47–7.22 (m, 7H), 6.92–6.74 (m, 4H), 5.01 (s, 2H), 4.88–4.70 (m, 2H), 4.35 (p, 1H, J=5.5 Hz), 3.95–3.86 (m, 1H), 3.83–3.74 (m, 2H), 3.53–3.44 (m, 1H); MS(m/e): 511 (M$^+$, 16), 429 (6), 239 (10), 173 (26), 91 (100), 82 (2).

Step 3: Preparation of 4-[cis-2-(2,4-dichlorophenyl)-2-(1H-1-triazolylmethyl)-1,3-dioxolan-4-ylmethoxy]phenol(II-b)[(2R,4S) , (2S,4R)]

The procedure of Step 3 of Preparation 4 was repeated except that 5.12 g of cis-4-(benzyloxyphenoxymethyl)-2-(2, 4-dichlorophenyl)-1,3-dioxolan-2-yl-(1H-1-triazolyl) methane(II-b-1) was used.

The reaction mixture was filtered to remove the catalyst and the solvent was evaporated. The resulting solid product was subjected to column chromatography using ethyl acetate as an eluent to obtain 2.74 g of the title compound as a white crystal. (yield 65%) (m.p.: 128° C.)

$^1$H-NMR (CDCl$_3$, TMS) δ (ppm): 8.98 (br.s, 1H), 8.40 (s, 1H), 7.86 (s, 1H), 7.66–7.65 (m, 1H), 7.55–7.33 (m, 2H), 6.78–6.65 (m, 4H), 4.88–4.73 (m, 2H), 4.39–4.28 (m, 1H), 3.95–3.86 (m, 1H), 3.78–3.63 (m, 3H); MS(m/e) 421 (M$^+$, 12), 339 (26), 173 (45), 149 (100), 121 (34), 109 (29).

PREPARATION 7

Preparation of cis-2-(2,4-dichlorophenyl)-2-(1H-1-imidazolylmethyl)-1,3-dioxolan-4-ylmethyl-4-piperazino-phenylether(II-c)[(2R,4S) or (2S,4R)]

Step 1: Preparation of 1-(4-{4-[cis-2-(2,4-dichlorophenyl)-2-(1H-1-imidazolylmethyl)-1,3-dioxolan-4-ylmethoxy]-phenyl}piperazino)-1-ethanone(II-c-1)[(2R,4S), (2S,4R)]

1-Acetyl-4-(4-hydroxyphenyl)piperazine was prepared using 1-(4-hydroxyphenyl)-piperazine.2Br by the procedure disclosed by Chapman, D. R. et al., *J. Heterocyclic Chem.*, 27, 2063 (1990) (m.p.: 172° C.; $^1$H-NMR (DMSO-d$_6$, TMS) δ (ppm): 8.89 (br.s, 1H), 6.82–6.62 (m, 4H), 3.59–3.49 (m, 4H), 2.96–2.84 (m, 4H), 2.01 (s, 3H); MS(m/e): 220 (M$^+$, 53), 177 (23), 148 (100), 120 (44), 56 (59), 43 (34)).

3.3 g (0.015 mol) of 1-acetyl-4-(4-hydroxyphenyl) piperazine, thus obtained, was mixed with 20 ml of dry dimethylsulfoxide, and 0.66 g sodium hydride (0.0165 mol) (NaH, 60%, dispersed in mineral oil) was added thereto. After stirring for 1 hour, 6.1 g of cis-2-(2,4-dichlorophenyl)-2-(1H-1-imidazolylmethyl)-1,3-dioxolan-4-ylmethane sulfonate(II-b-2) (0.015 mol) was added thereto and the mixture was stirred at 60–80° C. for 24 hours.

After cooling the reaction mixture, 100 ml of water was added thereto and the mixture was extracted with dichloromethane. The organic layer was dried over anhydrous magnesium sulfate and filtered. After removing the solvent, the resulting solid product was subjected to column chromatography using a mixture of dichloromethane and methanol (19:1) as an eluent to obtain 6.7 g of the title compound as a white crystal.(yield 84%) (m.p.: 112° C.)

$^1$H-NMR (CDCl$_3$, TMS) δ (ppm): 7.61–7.46 (m, 3H), 7.29–7.23 (m, 1H), 6.99–6.74 (m, 6H), 4.55–4.29 (m, 3H), 3.92–3.81 (m, 1H), 3.80–3.67 (m, 4H), 3.65–3.57 (m, 2H), 3.33–3.25 (m, 1H), 3.11–2.99 (m, 4H), 2.14 (s, 3H); MS (m/e): 530 (M$^+$, 0.2) , 172 (15) , 91 (100) , 81 (6).

Step 2: Preparation of cis-2-(2,4-dichlorophenyl)-2-(1H-1-imidazolyl)-1,3-dioxolan-4-ylmethyl-4-piperazinophenyl ether(II-c)[(2R,4S), (2S,4R)]

2.8 g of potassium hydroxide (0.05 mol) and 5.3g(0.01 mol) of 1-(4-{4-[cis-2-(2,4-dichlorophenyl)-2-(1H-1-imidazolylmethyl)-1,3-dioxolan-4-ylmethoxy]-phenyl}piperazino)-1-ethanone(II-c-1) were added to 30 ml of n-butanol and the mixture was refluxed for 24 hours, and cooled to room temperature.

100 ml of water was added to the reaction mixture and the mixture was extracted with chloroform. The organic layer was dried over anhydrous magnesium sulfate and filtered.

After removing the solvent, the resulting solid was subjected to column chromatography using a mixture of dichloromethane and methanol (4:1) as an eluent to obtain 4.0 g (yield 82%) of the title compound. (m.p.: 156° C.)

$^1$H-NMR(CDCl$_3$, TMS) δ (ppm): 7.59–7.45 (m, 3H), 7.27–7.21 (m, 1H), 6.98–6.73 (m, 6H), 4.55–4.29 (m, 3H), 3.91–3.82 (m, 1H), 3.79–3.66 (m, 2H), 3.35–3.27 (m, 1H), 3.03 (s, 8H), 2.21 (br.s, 1H); MS(m/e): 488 (M$^+$, 4.3), 459 (34), 173 (49), 120 (43), 82 (70), 56 (100).

preparation 8

Preparation of cis-2-(2,4-difluorophenyl)-2-(1H-1-imidazolylmethyl)-1,3-dioxolan-4-ylmethyl-4-piperazino-phenylether(II-c)[(2R,4S) or (2S,4R)]

Step 1: Preparation of 1-(4-{4-[cis-2-(2,4-difluorophenyl)-2-(1H-1-imidazolylmethyl)-1,3-dioxolan-4-ylmethoxy] phenyl)-piperazino)-1-ethanone(II-c-1)[(2R,4S), (2S,4R)]

The procedure of Step 1 of Preparation 7 was repeated except that 5.61 g of cis-2-(2,4-difluorophenyl)-2-(1H-1-imidazolylmethyl)-1,3-dioxolan-4-ylmethane sulfonate(II-b-2) (0.015 mol) was used.

After cooling the reaction mixture, 100 ml of water was added thereto and the mixture was extracted with dichloromethane. The organic layer was dried over anhydrous magnesium sulfate and filtered. After removing the solvent, the resulting liquid product was subjected to column chromatography using a mixture of dichloromethane and methanol (19:1) as an eluent to obtain 6.28 g of the title compound. (yield 84%)

$^1$H-NMR (CDCl$_3$, TMS) δ (ppm): 7.59–7.45 (m, 2H), 7.00–6.72 (m, 8H), 4.47–4.29 (m, 3H), 3.99–3.88 (m, 1H), 3.80–3.58 (m, 6H), 3.33–3.21 (m, 1H), 3.10–2.98 (m, 4H), 2.14 (s, 3H); MS (m/e): 498 (M$^+$, 23), 455 (4), 439 (100), 426 (63), 173 (25), 141 (47), 82 (52), 44 (67).

Step 2: Preparation of cis-2-(2,4-difluorophenyl)-2-(1H-1-imidazolyl)-1,3-dioxolan-4-ylmethyl-4-piperazinophenyl ether(II-c)[(2R,4S), (2S,4R)]

The procedure of Step 2 of Preparation 7 was repeated except that 30 ml of 1,4-dioxane, 2ml of 50% sodium hydroxide aq. solution (0.05 mol) and 4.98 g of 1-(4-{4-

[cis-2-(2,4-difluorophenyl)-2-(1H-1-imidazolylmethyl)-1,3-dioxolan-4-ylmethoxy]phenyl}piperazino)-1-ethanone(II-c-1) obtained in Step 1 were used.

After removing the solvent, the resulting solid product was subjected to column chromatography using a mixture of dichloromethane and methanol (9:1) as an eluent to obtain 3.0 g of the title compound. (yield 66%) (m.p.: 140° C.)

$^1$H-NMR (CDCl$_3$, TMS) δ (ppm): 7.49–7.41 (m, 2H), 6.95–6.92 (m, 2H), 6.87–6.79 (m, 4H), 6.72–6.67 (m, 2H), 4.38–4.22 (m, 3H), 3.86 (dd, 1H, J=13.74 Hz, 10.91 Hz), 3.68–3.61 (m, 2H), 3.21 (dd, 1H, J=15.88 Hz, 11.33 Hz), 2.99 (s, 8H), 2.68 (br.s, 1H); MS (m/e): 456 (M$^+$, 23), 439 (35), 427 (100), 414 (51), 375 (7), 167 (63), 141 (64), 82 (46), 56 (53).

The chemical structures and characterization data of the compounds obtained in Preparations 1 to 8 are shown in Table I.

hour, mixed with ice, acidified with conc. HCl and extracted three times with ether.

The combined organic layer was dried and, after removing the solvent under a reduced pressure, the residue was distilled at 64 to 65° C. under 33 mmHg to obtain 24.74 g of the title compound as a colorless oil (Yield: 71%).

$^1$H-NMR (CDCl$_3$, TMS) δ (ppm): 7.52–7.12 (m, 5H); MS(m/e): 174 (M$^+$, 21), 105 (100), 77 (82), 69 (54).

Step 2: Preparation of 1-hydroxy-2,2,2-trifluoroethyl-benzene(III-a-2)

12.2 g (0.07 mol) of 2,2,2-trifluoromethylphenylketone (III-a-3) obtained in the Step 1 was mixed with 150 ml of methanol and 1.32 g (0.035 mol) of sodium borohydride was added dropwise thereto with stirring. The mixture was stirred at room temperature for 1–2 hour and the solvent was removed. Then, ethyl acetate was added to the mixture and the mixture was washed three times with ether.

TABLE I

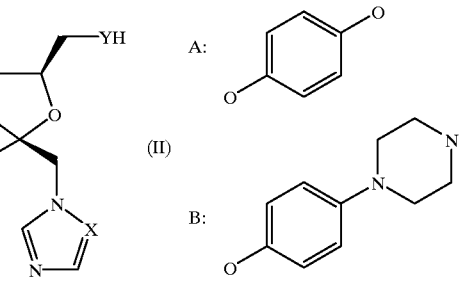

| Preparation | Stereo | X | R$^1$ | R$^2$ | Y | $^1$H-NMR(CDCl$_3$, TMS) δ (ppm) | MS(m/e) (M, int) |
|---|---|---|---|---|---|---|---|
| 1 | cis | CH | Cl | Cl | O | 7.60(s. 1H), 7.59(d, 1H, J=8.4Hz), 7.46(d, 1H, J=2.1Hz), 7.26(dd, 1H, J= 8.4Hz, 2.1Hz), 7.02(s, 1H), 7.00(s, 1H), 4.45(dd, 2H, J=56.0Hz, 14.7Hz), 4.12 (p, 1H, J=5.6Hz), 3.81(dd, 1H, J=7.05Hz, 8.0Hz), 3.65(dd, 1H, J= 3.40(dd, 1H, J=4.3Hz, 11.8Hz), 3.31(dd, 1H, J=5.1Hz, 11.8Hz), 2.32(br. s. 1H) | 329(M$^+$, 9.5), 247(85), 173(100), 57(35) 5.75Hz, 8.0Hz), |
| 2 | cis | CH | F | F | O | 7.53–7.44(m, 2H), 6.97(s, 2H), 6.90–6.82(m, 2H), 4.33(dd, 2H, J=42.43Hz, 24.45Hz), 4.14(p, 1H, J=9.97Hz), 3.84(dd, 1H, J=12.34Hz, 12.33Hz), 3.59(dd, 1H, J=13.42Hz, 9.76Hz), 3.29(d, 2H, J=8.99Hz), 2.05(br. s, 1H) | 296(M$^+$, 0.2), 265(5.5), 215(92), 141(100) |
| 3 | cis | N | Cl | Cl | O | 8.13(s, 1H), 7.96(s, 1H), 7.60–7.56(m, 1H), 7.49–7.48(m, 1H), 7.29–7.23(m, 1H), 4.77(s, 2H), 4.18–4.10(m, 1H), 3.90–3.82(m, 1H), 3.74–3.63(m, 2H), 3.31–3.21(m, 1H), 2.63(br.s, 1H) | 330(M$^+$+1, 1.6), 247(91), 173 (100), 116(27), 57(32) |
| 4 | cis | CH | Cl | Cl | A | 8.99(br. s, 1H), 7.48–6.67(m, 10H), 4.37–4.21(m, 3H), 3.90–3.78(m, 1H), 3.62–3.50(m, 2H), 3.46–3.35(m, 1H) | 420(M$^+$, 12), 386(41), 305(11), 210(17), 149(43), 82(100) |
| 5 | cis | CH | F | F | A | 8.97(br.s, 1H), 7.51–7.42(m, 2H), 7.38–7.26(m, 1H), 7.14–7.01(m, 2H), 6.81(s, 1H), 6.69–6.63(m, 4H), 4.44(s, 2H), 4.39(m, 1H), 3.95–3.87(m, 1H), 3.66–3.50(m, 2H), 3.48–3.42(m, 1H) | 388(M$^+$, 32), 307(4), 141(73), 82(100) |
| 6 | cis | N | Cl | Cl | A | 8.98(br.s, 1H), 8.40(s, 1H), 7.86(s, 1H), 7.66–7.65(m, 1H), 7.55–7.33(m, 2H), 6.78–6.65(m, 4H), 4.88–4.73(m, 2H), 4.39–4.28(m, 1H), 3.95–3.86(m, 1H), 3.78–3.63(m, 3H) | 421(M$^+$, 12), 339(26), 173(45), 149(100), :121(34), 109(29) |
| 7 | cis | CH | Cl | Cl | B | 7.59–7.45(m, 3H), 7.27–7.21 (m, 1 H), 6.98–6.73(m, 6H), 4.55–4.29(m 3H) 3.91–3.82(m, 1H), 3.79–3.66(m, 2H), 3.35–3.27(m, 1H), 3.03(s, 8H), 2.21(br.s, 1H) | 488(M$^+$, 4.3), 459(34), 173(49), 120(43), 82(7D), 56(100) |
| 8 | cis | CH | F | F | B | 7.49–7.41 (m, 2H), 6.95–6.92(m, 2H), 6.87–6.79(m, 4H), 6.72–6.67(m, 2H), 4.38–4.22(m, 3H), 3.86(dd, 1H, J=13.74Hz, 10.9lHz), 3.68–3.61(m, 2H), 3.21(dd, 1H, J=15.88Hz, 11.33Hz), 2.99(s, 8H), 2.68(br.s, 1H) | 456(M$^+$, 23), 439(35), 427(100), 414(51), 375(7), 167(63), 141(64), 82(46), 56(53) |

PREPARATION 9

Preparation of 2,2-difluorostyrene(III-a)

Step 1: Preparation of 2,2,2-trifluoromethylphenylketone (III-a-3)

5.1 g (0.21 mol) of magnesium and 300 ml of dry ether ere placed in a dry reactor under a N$_2$ atmosphere and 31.4 g (0.2 mol) of bromobenzene was added dropwise thereto to obtain a Grignard Reagent.

28.4 g (0.2 mol) of ethyltrifluoroacetate was added dropwise to the above at −78° C. The mixture was stirred for 1

The combined organic layer was dried and the solvent was removed under a reduced pressure. The residue was subjected to silica gel column chromatography using a mixture of n-hexane and ethyl acetate (4:1) as an eluent to obtain 12.07 g of the title compound(III-a-2). (yield 98%)

$^1$H-NMR (CDCl$_3$, TMS) δ (ppm): 7.54–7.13 (m, 5H), 4.87 (q 1H), 4.29 (br. s, 1H); MS (m/e): 176 (M$^+$, 39) , 107 (26) , 79 (91).

Step 3: Preparation of 1-chloro-2,2,2-trifluoroethylbenzene (III-a-1)

11.97 g (0.068 mol) of 1-hydroxy-2,2,2-trifluoroethyl-benzene obtained the Step 2 and 83 g of thionylchloride (0.7 mol) were added to 100 ml of dry toluene and the mixture was heated with stirring for 12 hours. The mixture was cooled to room temperature and washed with water. The organic layer was dried and the solvent was removed under a reduced pressure. The residue was subjected to silica gel column chromatography using n-hexane as an eluent to obtain 9.9 g of the title compound(III-a-1). (yield 75%)

$^1$H-NMR (CDCl$_3$, TMS) δ (ppm): 7.62–7.15 (m, 5H), 5.10 (q, 1H); MS (m/e): 194 (M$^+$, 94), 125 (100), 83 (30), 44 (81).

Step 4: Preparation of 2,2-difluorostyrene(III-a)

9.7 g (0.05 mol) of 1-chloro-2,2,2-trifluoroethyl-benzene (III-a-1) obtained in the Step 3 was mixed with 50 ml of dry tetrahydrofuran. Added thereto was 3.27 g of activated zinc and the mixture was refluxed with stirring for 12 hours. The mixture was cooled, filtered to remove the salts produced, and the solvent was removed under a reduced pressure.

The oily residue was subject to distillation at 58–59° C. under 49 mmHg to obtain 6.09 g of 2,2-difluorostyrene (III-a) ((yield 87%)

$^1$H-NMR (CDCl$_3$, TMS) δ (ppm): 7.45–7.10 (m, 5H), 5.20 (dd, 1H, J=26 Hz, 4 Hz); MS(m/e): 140 (M$^+$, 100), 120 (26), 84 (16), 44 (32).

PREPARATION 10 to 26

The procedure of Step 1 of Preparation 9 was repeated except that each of the corresponding halogenated compounds(III-a-4) was used in place of 4-bromobenzene to obtain various substituted 2,2,2-trifluoromethylphenylketone (III-a-3, Compounds A to Y) and the their characterization data are shown in Table II.

Then, the procedures of Steps 2 to 4 of Preparation 9 were repeated to obtain compounds of formula(III-a-2), (III-a-1) and (III-a), respectively. Their characterization data are shown in Tables III to V, respectively.

TABLE II

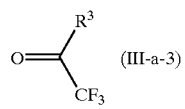

| Compound | R$^3$ | $^1$H-NMR(CDCl$_3$, TMS) δ (ppm) | MS(m/e) (M, int) | Yield (%) | B.P.(mmHg) Separation |
|---|---|---|---|---|---|
| A | C$_6$H$_5$— | 7.52–7.12(m, 5H) | 174(21), 105(100), 77(82), 69(54) | 71 | 64–65(33) |
| B | 3-CH$_3$—C$_6$H$_4$— | 7.52–6.92(m, 4H), 2.25(s, 3H) | 188(16), 135(45), 119(96), 91(100), 65(45) | 61 | 70–71(20) |
| C | 4-CH$_3$—C$_6$H$_4$— | 7.42–6.92(m, 4H), 2.25(s, 3H) | 188(12), 119(100), 91(96), 65(45) | 68 | 65–66(8) |
| D | 4-C$_2$H$_5$—C$_6$H$_4$— | 7.46–7.19(m, 4H), 2.68(q, 2H), 1.23(t, 3H) | 202(40), 133(91), 105(100), 76(64) | 62 | column |
| E | 4-n-C$_4$H$_9$—C$_6$H$_4$— | 8.14–7.29(m, 4H), 2.24(t, 2H), 1.96–1.03(m, 4H), 0.94(t, 3H) | 230(15), 161(100), 118(18), 91(55) | 52 | column |
| F | 4-t-C$_4$H$_9$—C$_6$H$_4$— | 7.46–7.02(m, 4H), 1.34(s, 9H) | 230(35), 161(100), 104(18) | 82 | column |
| G | 3,4-(CH$_3$)$_2$—C$_6$H$_3$— | 7.52–6.69(m, 3H), 2.23(s, 3H), 2.20(s, 3H) | 202(43), 133(98), 69(100) | 71 | column |
| H | 3,5-(CH$_3$)$_2$—C$_6$H$_3$— | 7.31–7.01(m, 3H), 2.25(s, 6H) | 202(24), 133(100), 69(24) | 69 | column |
| I | 2,4,5-(CH$_3$)$_3$—C$_6$H$_2$— | 7.46–6.98(m, 2H), 2.32(s, 3H), 2.28(s, 6H) | 216(24), 119(100), 97(23), 69(54) | 72 | 80–81(6) |
| J | 3-CF$_3$—C$_6$H$_4$— | 8.60–7.61(m, 4H) | 242(10), 173(68), 145(100), 76(62) | 67 | column |
| K | 4-CF$_3$—C$_6$H$_4$— | 8.55–7.56(m, 4H) | 242(37), 173(72), 145(100), 76(23) | 79 | column |
| L | 3-CH$_3$O—C$_6$H$_4$— | 7.41–6.79(m, 4H), 3.79(s, 3H) | 204(36), 135(100), 107(56), 77(94) | 78 | 64–65(33) |
| M | 4-CH$_3$O—C$_6$H$_4$— | 7.62–6.81(m, 4H), 3.86(s, 3H) | 204(56), 135(100), 107(86). 92(66), 77(92) | 85 | 72–73(20) |
| N | 4-C$_2$H$_5$O—C$_6$H$_4$— | 7.54–6.76(m, 4H), 4.09(q, 2H), 1.32(t, 3H) | 218(16), 149(88), 121(62), 76(100) | 69 | column |
| O | 3-(CH$_3$)$_2$CHO—C$_6$H$_4$— | 7.61–6.83(m, 4H), 4.54(m, 1H), 1.34(d, 6H) | 232(25), 163(76), 121(72), 76(100) | 88 | column |
| P | 3,4-OCH$_2$O—C$_6$H$_3$— | 7.92–7.43(m, 3H), 6.25–6.01(s, 2H) | 218(42), 149(100), 65(49) | 73 | column |
| Q | 4-C$_6$H$_5$O—C$_6$H$_4$— | 7.59–6.69(m, 9H) | 266(42), 197(100), 104(63), 97(53), 69(52) | 71 | column |
| R | 3-Cl—C$_6$H$_4$— | 8.38–7.45(m, 4H) | 208(10), 139(93), 111(100). 75(64) | 70 | 58–59(10) |
| S | 4-Cl—C$_6$H$_4$— | 7.51–7.41(m, 4H) | 208(100), 173(92), 97(54), 69(24) | 61 | 83–84(24) |
| T | 3-F—C$_6$H$_4$— | 7.56–6.89(m, 4H) | 192(25), 123(100), 95(78), 75(31) | 54 | 59–60(30) |
| U | 4-F—C$_6$H$_4$— | 7.76–6.92(m, 4H) | 192(16), 169(54), 123(100), 95(91), 75(76) | 59 | 66–67(34) |
| V | 3,5-Cl$_2$—C$_6$H$_3$ | 8.12–7.86(m, 3H) | 242(55), 173(100), 145(64), 109(32) | 45 | 75–76(4) |
| W | 3-CH$_3$-4-Cl—C$_6$H$_3$— | 7.46–7.02(m, 3H), 2.41(s. 3H) | 222(42), 187(72), 153(100), 69(24) | 82 | column |
| X | (naphthalen-2-yl) C$_{10}$H$_7$—2-yl- | 7.98–7.32(m, 7H) | 224(25), 155(100), 69(54) | 65 | column |
| Y | (thiopen-2-yl) C$_4$H$_3$S-2-yl- | 8.28–7.28(m, 3H) | 180(23), 111(45), 84(100) | 76 | column |

TABLE III

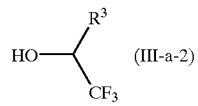

| Preparation | R³ | ¹H-NMR(CDCl₃, TMS) δ (ppm) | MS(m/e) (M, int) | Yield (%) | BP(mmHg) separation |
|---|---|---|---|---|---|
| 9 | C₆H₅— | 7.54–7.13(m, 5H), 4.87(q, 1H), 4.29(br. s, 1H) | 176(39), 107(100), 79(91) | 98 | 50–51(1) |
| 10 | 3-CH₃—C₆H₄— | 7.53–7.01(m, 4H), 4.87(q, 1H), 4.29(br. s, 1H), 2.24(s, 3H) | 190(24), 121(46), 84(100) | 89 | column |
| 11 | 4-CH₃—C₆H₄— | 7.45–6.92(m, 4H), 4.87(q, 1H), 4.30(br. s, 1H), 2.23(s, 3H) | 190(24), 121(100), 91(96), 69(45) | 89 | column |
| 12 | 4-C₂H₅—C₆H₄— | 7.43–7.18(m, 4H), 4.88(q, 1H), 2.81(br. s, 1H), 2.64(q, 2H), 1.24(t, 3H) | 204(13), 187(49), 135(100), 69(43) | 92 | column |
| 13 | 3,4-(CH₃)₂—C₆H₃— | 7.37–7.09(m, 3H), 4.95(q, 1H), 2.50(br. s, 1H), 2.26(s, 6H) | 204(21), 187(59), 118(100), 99(32), 69(54) | 88 | column |
| 14 | 3,5-(CH₃)₂—C₆H₃— | 7.32–7.01(m, 3H), 4.98(q, 1H), 2.48(br. s, 1H), 2.25(s, 6H) | 204(42), 187(42), 118(100), 99(24), 69(23) | 84 | column |
| 15 | 2,4,5-(CH₃)₃—C₆H₂— | 748–6.98(m, 2H), 5.31(q, 1H), 2.48(br. s, 1H), 2.32(s, 3H), 2.28(s, 6H) | 218(52), 201(24), 119(82), 69(100) | 89 | column |
| 16 | 3-CH₃O—C₆H₄— | 7.45–6.79(m, 4H), 4.94(q, 1H), 3.79(s, 3H), 3.21(br. s, 1H) | 206(39), 137(53), 109(99), 94(75), 84(100) | 88 | column |
| 17 | 4-CH₃O—C₆H₄— | 7.62–6.78(m, 4H), 4.92(q, 1H), 3.94(br. s, 1H), 3.86(s, 3H) | 206(42), 191(62), 137(100), 69(56) | 97 | column |
| 18 | 4-C₂H₅O—C₆H₄— | 7.43–6.82(m, 4H), 4.93(q, 1H), 4.12(q, 2H), 3.24(br. s, 1H), 1.34(t, 3H) | 220(28), 175(100), 151(84), 69(46) | 93 | column |
| 19 | 3-(CH₃)₂CHO—C₆H₄— | 7.33–6.84(m, 4H), 4.97(q, 1H), 4.52(m, 1H), 3.34(br. s, 1H), 1.32(d, 6H) | 234(46), 192(78), 123(100), 95(43) | 89 | column |
| 20 | 3,4-OCH₂O—C₆H₃— | 7.89–7.37(m, 3H), 6.02(s, 2H), 4.95(q, 1H), 342(br. s, 1H) | 220(51), 174(92), 134(100), 92(49) | 91 | column |
| 21 | 3-Cl—C₆H₄— | 7.48–7.25(m, 4H), 4.96(q, 1H), 3.57(br. s, 1H) | 210(55), 141(94), 86(100), 77(46) | 75 | column |
| 22 | 4-Cl—C₆H₄— | 7.51–7.41(m, 4H), 4.97(q, 1H), 3.61(br. s, 1H) | 210(52), 141(100), 111(23), 99(49), 69(82) | 76 | column |
| 23 | 3-F—C₆H₄— | 7.56–6.87(m, 4H), 4.95(q, 1H), 3.24(br. s, 1H) | 194(100), 177(82), 124(54), 97(82) | 82 | column |
| 24 | 4-F—C₆H₄— | 7.76–6.92(m, 4H), 4.98(q, 1H), 3.18(br. s, 1H) | 194(100), 177(14), 124(47), 97(96) | 81 | 63–64(33) |
| 25 | 3-CH₃-4-Cl—C₆H₃— | 7.54–7.21(m, 3H), 492(q, 1H), 3.48(br. s, 1H), 2.37(s, 3H) | 224(46), 189(100), 127(73), 98(46) | 87 | column |
| 26 | (naphthalen-2-yl) C₁₀H₇-2-yl- | 8.12–7.28(m, 7H), 5.92(q, 1H), 2.54(br. s, 1H) | 226(54), 127(100), 99(25), 69(45) | 65 | column |

TABLE IV

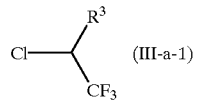

(III-a-1)

| Preparation | R³ | ¹H-NMR(CDCl₃, TMS) δ (ppm) | MS(m/e)(m/e) (M, int) | Yield (%) | BP(mmHg) separation |
|---|---|---|---|---|---|
| 9 | C₆H₅— | 7.62–7.15(m, 5H), 5.10(q, 1H) | 194(94), 125(100), 83(30), 44(81) | 75 | column |
| 10 | 3-CH₃—C₆H₄— | 7.49–7.01(m, 4H), 5.01(q, 1H), 2.24(s, 3H) | 208(52), 173(100), 104(26), 69(23) | 82 | column |
| 11 | 4-CH₃—C₆H₄— | 7.42–6.92(m, 4H), 5.01(q, 1H), 2.26(s, 3H) | 208(64), 173(92), 104(100), 69(28) | 65 | column |
| 12 | 4-C₂H₅—C₆H₄— | 7.45–7.16(m, 4H), 5.06(q, 1H), 2.64(q, 2H), 1.23(t, 3H) | 222(59), 187(100), 153(83), 105(79) | 73 | column |
| 13 | 3,4-(CH₃)₂—C₆H₃ | 7.38–7.02(m, 3H), 5.01(q, 1H), 2.25(s, 6H) | 222(36), 187(56), 117(100) | 86 | column |
| 14 | 3,5-(CH₃)₂—C₆H₃— | 7.29–7.01 (m, 3H), 5.02(q, 1H), 2.32(s, 6H) | 222(32), 187(24), 117(100) | 82 | column |
| 15 | 2,4,5-(CH₃)₃—C₆H₂— | 7.48–6.98(m, 2H), 5.43(q, 1H), 2.32(s, 3H), 2.28(s, 6H) | 236(20), 201(100), 167(39) | 88 | column |
| 16 | 3-CH₃O—C₆H₄— | 7.51–6.80(m, 4H), 5.10(q, 1H), 3.80(s, 3H) | 224(10), 86(100) | 79 | column |
| 17 | 4-CH₃O—C₆H₄— | 7.62–6.81(m, 4H), 5.01(q, 1H), 3.86(s, 3H) | 224(23), 189(100), 158(79), 69(43) | 79 | column |
| 18 | 4-C₂H₅O—C₆H₄— | 7.51–6.84(m, 4H), 5.12(q, 1H), 4.13(q, 2H), 1.31(t, 3H) | 238(73), 203(100), 158(62), 80(42) | 83 | column |
| 19 | 3-(CH₃)₂CHO—C₆H₄— | 7.32–6.83(m, 4H), 5.02(q, 1H), 4.52(m, 1H), 1.32(d, 6H) | 252(31), 210(100), 175(27), 141(34) | 62 | column |
| 20 | 3,4-OCH₂O—C₆H₃— | 7.72–7.21(m, 3H), 6.10(s, 2H), 5.04(q, 1 H) | 238(42), 203(100), 134(73), 69(54) | 79 | column |
| 21 | 3-Cl—C₆H₄— | 7.53–7.24(m, 4H), 5.08(q, 1 H) | 228(20), 159(42), 84(100), 69(37) | 63 | column |
| 22 | 4-Cl—C₆H₄— | 7.51–7.41(m, 4H), 5.02(q, 1H) | 228(100), 111(54), 69(52) | 76 | column |
| 23 | 3-F—C₆H₄— | 7.56–6.87(m, 4H), 5.03(q, 1H) | 212(42), 177(100), 69(52) | 76 | column |
| 24 | 4-F—C₆H₄— | 7.76–6.91(m, 4H), 5.10(q, 1H) | 212(23), 177(100), 69(39) | 76 | column |
| 25 | 3-CH₃-4-Cl—C₆H₃— | 7.43–7.21(m, 3H), 5.08(q, 1H), 2.39(s, 3H) | 270(15), 235(49), 165(190), 154(48) | 78 | column |
| 26 | (naphthalen-2-yl) C₁₀H₇-2-yl- | 8.12–7.36(m, 7H), 6.01(q, 1H) | 244(100), 127(69), 117(54) | 86 | column |

TABLE V

PREPARATION 27

Preparation of 2,2-difluoro-1-trifluoromethylstyrene (III-b)

100 ml of dry tetrahydrofuran and 26.2 g (0.1mol) of triphenylphosphine were placed in a flask and 25.2 g (0.12 mol) of dibromodifluoromethane ($CF_2Br_2$) was added dropwise thereto while maintaining the temperature of the reaction mixture at below 10° C.

The mixture was stirred for 30 minutes and added thereto was 8,71 g (0.05 mol) of 2,2,2-trifluoromethylphenylketone (III-a-3). The resulting mixture was refluxed for 48 hours and cooled to room temperature.

The mixture was distilled to obtain an oily product, which was redistilled at 51–52° C. under 44 mmHg to obtain 6.97 g of 2,2-difluoro-1-trifluoromethylstyrene as a colorless oily product. (Yield: 67%).

$^1$H-NMR ($CDCl_3$, TMS) δ: 7.59–7.31 (m, 5H); MS (m/e): 208 (M$^+$, 48), 84 (83), 43 (100).

PRAPARATION 28 to 47

The procedure of Preparation 27 was repeated except that 2,2,2-trifluoromethylphenylketone(III-a-4) (Compound A to Y) was used in each case to obtain fluorinated vinyl compounds of formula (III-b) and the their characterization data are shown in Table VI.

dispersed in mineral oil) was added thereto, followed by stirring for 30 minutes.

Then, 140 mg (1 mmol) of 2,2-difluorostyrene(III-a) prepared from 2,2,2-trifluoroacetophenone was added slowly to the mixture and stirred for 1–2 hours.

After adding water, the reaction mixture was extracted with ethyl acetate. The organic layer was dried and the solvent was removed under a reduced pressure and the residue was subjected to the silica gel column chromatography using a mixture of n-hexane and ethyl acetate (2:1) as an eluent to obtain 377 mg (yield 84%) of the title compound as colorless oil.

$^1$M-NMR ($CDCl_3$, TMS) δ (ppm) 7.59–6.86 (m, 11H), 5.25 (d, 1H, E), 4.67 (d, 1H, Z), 4.52–4.25 (m, 3H), 3.91–3.52 (m, 4H), MS(m/e): 448 (M$^+$, 51), 311 (60), 275 (45), 175 (100), 109 (87), 58 (52); $^{19}$F-NMR ($CDCl_3$, $CFCl_3$) δ (ppm): −83.67 (Z, J=30.95 Hz), −86.49 (E, J=6.97 Hz) (d, 1F).

EXAMPLE 19

Preparation of (E&Z) 1-{4-[cis-2-(2,4-dichlorophenyl)-2-(1H-1-imidazolylmethyl)-1,3-dioxolan-4-ylmethoxy]-phenoxy}-1,3,3,3-tetrafluoro-2-phenyl-1-propene 329 mg of 2-(2,4-dichlorophenyl)-2-(1H-1-imidazolylmethyl)-1,3-dioxolan-4-ylmethanol(II-a) (1

TABLE VI

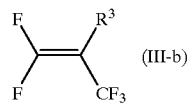

(III-b)

| Preparation | R$^3$ | $^1$H-NMR(CDCl$_3$, TMS) δ (ppm) | MS(m/e)(m/e) (M, int) | Yield (%) | BP(mmHg) Separation |
|---|---|---|---|---|---|
| 27 | C$_6$H$_5$— | 7.59–7.31(m, 5H) | 208(48), 84(83), 43(100) | 68 | 51–52(44) |
| 28 | 3-CH$_3$—C$_6$H$_4$— | 7.46–6.98(m, 4H), 2.43(s, 3H) | 222(20), 203(70), 134(100) | 45 | column |
| 29 | 4-CH$_3$—C$_6$H$_4$— | 7.32–7.18(m, 4H), 2.45(s, 3H) | 222(64), 203(23), 134(100) | 62 | column |
| 30 | C$_2$H$_5$—C$_6$H$_4$— | 7.38–7.25(m, 4H), 2.68(q, 2H), 1.19(t, 3H) | 236(20), 145(100), 90(54) | 62 | column |
| 31 | 4-n-C$_4$H$_9$—C$_6$H$_4$— | 7.32–7.25(m, 4H), 2.69(t, 2H), 2.01–1.23(m, 4H), 1.09(t, 3H) | 264(30), 221(37), 151(36), 84(100), 57(50) | 58 | column |
| 32 | 4-t-C$_4$H$_9$—C$_6$H$_4$— | 7.42–6.92(m, 4H), 1.37(s, 9H) | 264(25), 249(100), 221 (41), 119(41) | 68 | column |
| 33 | 3,4-(CH$_3$)$_2$—C$_6$H$_3$— | 7.28–7.02(m, 3H), 2.38(s, 3H), 2.32(s, 3H) | 236(18), 84(33), 45(100) | 78 | column |
| 34 | 3,5-(CH$_3$)$_2$—C$_6$H$_3$— | 7.32–7.12(m, 3H), 2.41(s, 6H) | 236(29), 217(68), 148(100), 45(92) | 98 | column |
| 35 | 3-CF$_3$—C$_6$H$_4$— | 7.82–7.18(m, 4H) | 276(52), 257(92), 188(100) | 52 | column |
| 36 | 4-CF$_3$—C$_6$H$_4$— | 7.81–7.42(m, 4H) | 276(42), 257(78), 188(95), 107(100) | 64 | column |
| 37 | 3-CH$_3$O—C$_6$H$_4$— | 7.48–6.87(m, 4H), 3.81(s, 3H) | 238(42), 207(45), 139(100), 69(94) | 54 | 75(10) |
| 38 | 4-CH$_3$O—C$_6$H$_4$— | 7.48–6.79(m, 4H), 3.79(s, 3H) | 238(69), 195(14), 145(35), 74(33), 59(100) | 79 | 72–74(10) |
| 39 | 4-C$_2$H$_5$O—C$_6$H$_4$— | 7.51–6.85(m, 4H), 4.12(q, 2H), 1.29(t, 3H) | 252(47), 233(100), 84(64) | 73 | column |
| 40 | 3,4-OCH$_2$O—C$_6$H$_3$— | 7.01–6.79(m, 3H), 6.01(s, 2H) | 252(46), 233(63), 164(82), 69(100) | 72 | column |
| 41 | 4-C$_6$H$_5$O—C$_6$H$_4$— | 7.49–6.96(m, 9H) | 300(75), 281(56), 207(100), 93(83) | 69 | column |
| 42 | 3-Cl—C$_6$H$_4$— | 7.54–7.23(m, 4H) | 242(26), 223(72), 188(49), 69(100) | 63 | column |
| 43 | 4-Cl—C$_6$H$_4$— | 7.56–7.21(m, 4H) | 242(35), 174(70), 139(100), 69(79) | 45 | 58(10) |
| 44 | 3-F—C$_6$H$_4$— | 7.53–6.96(m, 4H) | 226(52), 207(25), 84(100) | 54 | column |
| 45 | 4-F—C$_6$H$_4$— | 7.52–6.83(m, 4H) | 226(20), 64(100) | 63 | column |
| 46 | 3,5-Cl$_2$—C$_6$H$_3$— | 7.57–7.19(m, 3H) | 276(100), 241(45) | 84 | 85(10) |
| 47 | (thiophen-2-yl) C$_4$H$_3$S-2-yl- | 7.67–6.92(m, 3H) | 214(42), 195(92), 126(100), 47(86) | 63 | column |

EXAMPLE 1

Preparation of (E&Z) 1-[cis-2-(2,4-dichlorophenyl)-2-(1H-1-imidazolylmethyl)-1,3-dioxolan-4-ylmethoxy]-1-fluoro-2-phenyl-1-ethene 329 mg of cis 2-(2,4-dichlorophenyl)-2-(1H-1-imidazolylmethyl)-1,3-dioxolan-4-ylmethanol(II-a) (1 mmol) was mixed with 10 ml of acetonitrile in a dry reactor and 44 mg (1.1 mmol) of sodium hydride(NaH, 60%, mmol) was mixed with 10 ml of acetonitrile in a dry reactor and 44 mg of sodium hydride(NaH, 60%, dispersed in mineral oil) was added thereto, followed by stirring for 30 minutes.

Then, 208 mg (1 mmol) of 2,2-difluoro-1-trifluorostyrene prepared from 2,2,2-trifluoroacetophenone was added slowly to the mixture and stirred for 1–2 hours.

The solvent was removed under a reduced and the residue was subjected to silica gel column chromatography using a mixture of n-hexane and ethyl acetate(2:1) as an eluent to obtain 460 mg (yield 89%) of the title compound as a mixture of E- and Z-isomers (2:1) in the form of a colorless oil.

$^1$H-NMR(CDCl$_3$, TMS) δ (ppm): 7.57–6.79 (m, 11H), 4.54–4.27 (m, 2H), 4.19–3.35 (m, 5H); MS (m/e): 516 (M$^+$, 35), 435 (40) 172 (100), 127 (51), 84 (64); $^{19}$F-NMR (CDCl$_3$, CFCl$_3$) δ (ppm): −57.60 (Z, J=23.90 Hz), −57.92 (E, J=12.76 Hz) (d, 3F), −78.37 (E, J=12.67 Hz), −79.49 (Z, J=23.86 Hz)(q, 1F).

Examples 2 to 18 and 20 to 150

The procedure of Example 1 or 19 was repeated using a suitable starting materials, i.e., corresponding compounds of formula (II) and fluorinated vinyl compound of formula (III) to obtain the compounds shown in Table VII.

TABLE VII

A: 1,4-disubstituted benzene (para-dihydroxy type)
B: 4-(piperazin-1-yl)phenoxy group Structure (I): dichlorophenyl-dioxolane-imidazole-fluorovinyl compound

| Ex. | stereo | X | R¹ | R² | Y | R³ | R⁴ | ¹H-NMR (CDCl₃, TMS) δ (ppm) | MS(m/e) (M, int) |
|---|---|---|---|---|---|---|---|---|---|
| 1 | cis | CH | Cl | Cl | O | —C₆H₅ | H | 7.59–6.86(m, 11H), 5.25(d, 1H, E), 4.81(d, 1H, Z), 4.52–4.25(m, 3H), 3.91–3.52(m, 4H) | 448(51), 311(60), 275(45), 175(100), 109(87), 58(52) |
| 2 | cis | CH | Cl | Cl | O | 3-CH₃—C₆H₄ | H | 7.60–6.90(m, 10H), 5.23(d, 1H, E), 4.80(d, 1H, Z), 4.53–4.27(m, 3H), 3.92–3.43(m, 4H), 2.31(s, 3H) | 462(32), 255(60), 173(100), 123(78) |
| 3 | cis | CH | Cl | Cl | O | 4-CH₃—C₆H₄ | H | 7.59–6.87(m, 10H), 5.24(d, 1H, E), 4.80(d, 1H, Z), 4.54–4.25(m, 3H), 3.91–3.54(m, 4H), 2.32(s, 3H) | 462(56), 311(59), 255(86), 173(100), 123(93), 82(50) |
| 4 | cis | CH | Cl | Cl | O | 4-C₂H₅—C₆H₄ | H | 7.59–6.90(m, 10H), 5.24(d, 1H, E), 4.80(d, 1H, Z), 4.51–4.26(m, 3H), 3.90–3.53(m, 4H), 2.62(q, 2H), 1.21(t, 3H) | 476(34), 311(36), 255(46), 175(91), 82(100), 58(69) |
| 5 | cis | CH | Cl | Cl | O | 3,4-(CH₃)₂—C₆H₃ | H | 7.60–6.86(m, 9H), 5.22(d, 1H, E), 4.78(d, 1H, Z), 4.52–4.23(m, 3H), 3.91–3.52(m, 4H), 2.22(s, 6H) | 476(25), 311(78), 255(94), 246(55), 173(100), 137(68) |
| 6 | cis | CH | Cl | Cl | O | 3,5-(CH₃)₂—C₆H₃ | H | 7.59–6.82(m, 9H), 5.22(d, 1H, E), 4.77(d, 1H, Z), 4.54–4.27(m, 3H), 3.91–3.58(m, 4H), 2.30(s, 6H) | 476(35), 311(65), 255(73), 246(56), 175(99), 137(100) |
| 7 | cis | CH | Cl | Cl | O | 2,4,5-(CH₃)₃—C₆H₂ | H | 7.58–6.87(m, 8H), 5.30(d, 1H, E), 4.80(d, 1H, Z), 4.51–4.22(m, 3H), 3.85–3.53(m, 4H), 2.26(s, 9H) | 491(51), 247(70), 175(66), 173(100), 81(22) |
| 8 | cis | CH | Cl | Cl | O | 3-CH₃O—C₆H₄ | H | 7.53–6.70(m, 10H), 5.23(d, 1H, E), 4.80(d, 1H, Z), 4.54–4.29(m, 3H), 3.90–3.54(m, 4H), 3.79(s, 3H) | 479(12), 311(53), 255(48), 173(100), 135(81), 81(47) |
| 9 | cis | CH | Cl | Cl | O | 4-CH₃O—C₆H₄ | H | 7.60–6.81(m, 10H), 5.23(d, 1H, E), 4.79(d, 1H, Z), 4.53–4.27(m, 3H), 3.91–3.52(m, 4H), 3.79(s, 3H) | 478(12), 311(77), 255(74), 175(50), 139(100) |
| 10 | cis | CH | Cl | Cl | O | 4-C₂H₅O—C₆H₄ | H | 7.89–6.80(m, 10H), 5.20(d, 2H, 4H), 4.73(d, 1H, Z), 4.56–4.05(m, 3H), 4.03–3.20(m, 4H), 3.99(q, 2H), 1.44(t, 3H) | 493(34), 247(100), 175(52), 173(91), 81(18) |
| 11 | cis | CH | Cl | Cl | O | 3-(CH₃)₂CHO—C₆H₄ | H | 7.56–6.67(m, 10H), 5.23(d, 1H, E), 4.76(d, 1H, Z), 4.69–4.07(m, 4H), 3.88–3.50(m, 4H), 1.30(d, 6H) | 507(18), 247(44), 173(54), 149(15), 84(34), 44(100) |
| 12 | cis | CH | Cl | Cl | O | 3,4-OCH₂O—C₆H₃ | H | 6.74–6.74(m, 9H), 5.94(s, 2H), 5.21(d, 1H, E), 4.77(d, 1H, Z), 4.51–4.26(m, 3H), 3.94–3.50(m, 4H) | 492(14), 311(83), 255(100), 173(91), 153(90) |
| 13 | cis | CH | Cl | Cl | O | 3-Cl—C₆H₄ | H | 7.58–6.92(m, 10H), 5.19(d, 1H, E), 4.74(d, 1H, Z), 4.48–4.30(m, 3H), 3.90–3.22(m, 4H) | 484(20), 311(56), 172(100), 143(39) |
| 14 | cis | CH | Cl | Cl | O | 4-Cl—C₆H₄ | H | 7.60–6.86(m, 10H), 5.21(d, 1H, E), 4.77(d, 1H, Z), 4.57–4.25(m, 3H), 3.91–3.49(m, 4H) | 482(15), 311(54), 175(100), 143(68) |
| 15 | cis | CH | Cl | Cl | O | 3-F—C₆H₄ | H | 7.58–6.82(m, 10H), 5.23(d, 1H, E), 4.78(d, 1H, Z), 4.55–4.27(m, 3H), 3.92–3.23(m, 4H) | 467(12), 173(100), 127(67), 81(35) |
| 16 | cis | CH | Cl | Cl | O | 4-F—C₆H₄ | H | 7.60–6.84(m, 10H), 5.23(d, 1H, E), 4.79(d, 1H, Z), 4.53–4.24(m, 3H), 3.91–3.51(m, 4H) | 466(31), 311(44), 255(40), 173(100), 127(94), 81(50) |

TABLE VII-continued

A: 4-hydroxyphenyl (phenol with OH para)
B: 4-(4-morpholinyl)phenoxy type (morpholine N-linked to phenyl-O)

Structure (I): cis-configured 1,3-dioxolane bearing imidazolylmethyl and an ether-linked fluoroalkene substituted with R³/R⁴; phenyl ring substituted with R¹, R².

| Ex. | stereo | X | R¹ | R² | Y | R³ | R⁴ | ¹H-NMR (CDCl₃, TMS) δ (ppm) | MS(m/e) (M, int) |
|---|---|---|---|---|---|---|---|---|---|
| 17 | cis | CH | Cl | Cl | O | 3-CH₃, 4-Cl—C₆H₃ | H | 7.58–6.90(m, 9H), 5.16(d, 1H, E), 4.70(d, 1H, Z), 4.52–4.27(m, 3H), 3.89–3.53(m, 4H), 2.34(s, 3H) | 498(8), 310(71), 173(100), 81(52) |
| 18 | cis | CH | Cl | Cl | O | C₁₀H₇ | H | 8.11–6.82(m, 13H), 5.89(d, 1H, E), 5.41(d, 1H, Z), 4.61–4.16(m, 3H), 3.98–3.41(m, 4H) | 498(16), 311(70), 255(46), 175(67), 159(100), 58(52) |
| 19 | cis | CH | Cl | Cl | O | C₆H₅ | CF₃ | 7.57–6.79(m, 11H), 4.54–4.27(m, 2H), 4.19–3.35(m, 5H) | 516(35), 435(40), 172(100), 127(51), 84(64) |
| 20 | cis | CH | Cl | Cl | O | 3-CH₃—C₆H₄ | CF₃ | 7.61–6.81(m, 10H), 4.59–4.24(m, 2H), 4.15(m, 1H), 4.00–3.40(m, 4H), 2.39(s, 3H) | 530(6), 449(30), 167(50), 148(100), 57(48) |
| 21 | cis | CH | Cl | Cl | O | 4-CH₃—C₆H₄ | CF₃ | 7.54–6.82(m, 10H), 4.59–4.31(m, 2H), 4.12(m, 1H), 3.98–3.41(m, 4H), 2.38(s, 3H) | 530(27), 449(72), 173(100), 105(42) |
| 22 | cis | CH | Cl | Cl | O | 4-C₂H₅—C₆H₄ | CF₃ | 7.58–6.80(m, 10H), 4.60–4.29(m, 2H), 4.13(m, 1H), 4.00–3.40(m, 4H), 2.65(q, 2H), 1.26(t, 3H) | 544(52), 465(51), 225(62), 173(100), 82(66) |
| 23 | cis | CH | Cl | Cl | O | 3,4-(CH₃)₂—C₆H₃ | CF₃ | 7.58–6.79(m, 9H), 4.58–4.24(m, 2H), 4.15(m, 1H), 3.97–3.40(m, 4H), 2.25(s, 6H) | 544(53), 462(29), 243(28), 205(30), 172(100), 81(67) |
| 24 | cis | CH | Cl | Cl | O | 3,5-(CH₃)₂—C₆H₃ | CF₃ | 7.55–6.78(m, 9H), 4.56–4.26(m, 2H), 4.09(m, 1H), 3.96–3.38(m, 4H), 2.24(s, 6H) | 544(25), 167(46), 148(100) |
| 25 | cis | CH | Cl | Cl | O | 4-CF₃—C₆H₄ | CF₃ | 7.81–6.80(m, 10H), 4.58–4.32(m, 2H), 4.22(m, 1H), 3.94–3.37(m, 4H) | 584(17), 502(100), 172(89) |
| 26 | cis | CH | Cl | Cl | O | 3-CH₃O—C₆H₄ | CF₃ | 7.54–7.19(m, 5H), 7.01–6.83(m, 5H), 4.54–4.28(m, 2H), 4.15(m, 1H), 3.93–3.41(m, 4H), 3.79(s, 3H) | 546(22), 517(16), 465(53), 311(16), 173(100), 81(16) |
| 27 | cis | CH | Cl | Cl | O | 4-CH₃O—C₆H₄ | CF₃ | 7.56–6.76(m, 10H), 4.60–4.28(m, 2H), 4.13(m, 1H), 3.99–3.38(m, 4H), 3.78(s, 3H) | 546(21), 465(51), 255(39), 207(33), 173(100) |
| 28 | cis | CH | Cl | Cl | O | 3,4-OCH₂O—C₆H₃ | CF₃ | 7.65–6.78(m, 9H), 5.98(s, 2H), 4.54–4.22(m, 2H), 4.19(m, 1H), 3.97–3.39(m, 4H) | 560(32), 525(39), 254(37), 218(31), 172(100), 82(60) |
| 29 | cis | CH | Cl | Cl | O | 4-C₆H₅O—C₆H₄ | CF₃ | 7.55–6.85(m, 15H), 4.48–4.06(m, 3H), 3.89–3.38(m, 4H) | 609(20), 515(23), 173(45), 84(87), 43(100) |
| 30 | cis | CH | Cl | Cl | O | 3-Cl—C₆H₄ | CF₃ | 7.56–6.85(m, 10H), 4.49–4.04(m, 3H), 3.93–3.39(m, 4H) | 552(16), 469(48), 175(56), 173(100), 81(13) |
| 31 | cis | CH | Cl | Cl | O | 4-Cl—C₆H₄ | CF₃ | 7.54–6.72(m, 10H), 4.54–4.25(m, 2H), 4.11(m, 1H), 3.98–3.28(m, 4H) | 550(16), 469(69), 173(100) |
| 32 | cis | CH | Cl | Cl | O | 3-F—C₆H₄ | CF₃ | 7.60–6.80(m, 10H), 4.55–4.28(m, 2H), 4.17(m, 1H), 3.95–3.38(m, 4H) | 534(11), 453(92), 172(100) |
| 33 | cis | CH | Cl | Cl | O | 4-F—C₆H₄ | CF₃ | 7.64–6.81(m, 10H), 4.56–4.25(m, 2H), 4.14(m, 1H), 3.98–3.55(m, 4H) | 534(13), 453(87), 172(100) |
| 34 | cis | CH | Cl | Cl | O | 3,5-Cl₂—C₆H₃ | CF₃ | 7.66–6.83(m, 9H), 4.58–4.24(m, 2H), 4.18(m, 1H), 3.91–3.38(m, 4H) | 584(32), 524(100), 504(50), 174(50) |

TABLE VII-continued

A:

[structure: para-disubstituted benzene with O and O substituents]

B:

[structure: para-substituted phenyl-piperazine with N-containing ring and O]

(I)

[structure: core formula with R¹, R², R³, R⁴, X, Y substituents on a dioxolane-imidazole system]

| Ex. | stereo | X | R¹ | R² | Y | R³ | R⁴ | ¹H-NMR (CDCl₃, TMS) δ (ppm) | MS(m/e) (M, int) |
|---|---|---|---|---|---|---|---|---|---|
| 35 | cis | CH | Cl | Cl | O | C₄H₃S | CF₃ | 7.75–6.82(m, 9H), 4.56–4.31(m, 2H), 4.21(m, 1H), 3.98–3.51(m, 4H) | 522(45), 311(84), 254(64), 172(100) |
| 36 | cis | CH | F | F | O | C₆H₅ | H | 7.16–6.78(m, 11H), 5.20(d, 1H, E), 4.74(d, 1H, Z), 4.43–4.20(m, 3H), 3.90–3.40(m, 4H) | 416(16), 149(74), 141(100), 91(62), 71(33) |
| 37 | cis | CH | F | F | O | 3-CH₃—C₆H₄ | H | 762–6.75(m, 10H), 5.22(d, 1H, E), 4.77(d, 1H, Z), 4.43–4.20(m, 3H), 3.93–3.53(m, 4H), 2.33(s, 3H) | 430(20), 279(42), 167(50), 149(100), 71(55) |
| 38 | cis | CH | F | F | O | 4-CH₃—C₆H₄ | H | 761–6.77(m, 10H), 5.21(d, 1H, E), 4.75(d, 1H, Z), 4.42–4.20(m, 3H), 3.93–3.51(m, 4H), 2.31(s, 3H) | 430(24), 279(61), 167(55), 149(100), 71(55), 57(94) |
| 39 | cis | CH | F | F | O | 4-C₂H₅—C₆H₄ | H | 7:43–6.73(m, 10H), 5.20(d, 1H, E), 4.77(d, 1H, Z), 4.35–4.11(m, 3H), 3.92–3.50(m, 4H), 2.57(q, 2H), 1.23(t, 3H) | 444(49), 223(62), 141(100), 82(36), 57(27) |
| 40 | cis | CH | F | F | O | 3,4-(CH₃)₂—C₆H₃ | H | 7:43–6.77(m, 9H), 5.30(d, 1H, E), 4.85(d, 1H, Z), 4.39–4.20(m, 3H), 3.89–3.52(m, 4H), 2.21(s, 6H) | 444(53), 279(29), 140(100), 81(54), 54(41) |
| 41 | cis | CH | F | F | O | 3,5-(CH₃)₂—C₆H₃ | H | 7.60–6.70(m, 9H), 5.20(d, 1H, E), 4.75(d, 1H, Z), 4.45–4.10(m, 3H), 3.98–3.50(m, 4H), 2.25(s, 6H) | 444(58), 279(35), 141(100), 137(63), 81(54) |
| 42 | cis | CH | F | F | O | 2,4,5-(CH₃)₃—C₆H₂ | H | 7:43–6.75(m, 8H), 5.29(d, 1H, m, 4.84(d, 1H, Z), 4.39–4.20(m, 3H), 3.89–3.51(m, 4H), 2.20(s, 9H) | 458(28), 223(73), 141(64), 81(100) |
| 43 | cis | CH | F | F | O | 3-CH₃O—C₆H₄ | H | 7.58–6.77(m, 10H), 5.20(d, 1H, m, 4.76(d, 1H, Z), 4.43–4.19(m, 3H), 3.92–3.20(m, 4H), 3.76(s, 3H) | 446(12), 279(100), 223(83), 140(83) |
| 44 | cis | CH | F | F | O | 4-C₂H₅O—C₆H₄ | H | 7.55–6.78(m, 10H), 5.21(d, 2H, Z), 4.78(d, 1H Z), 4.38–4.01(m, 4H), 3.98–3.25(m, 4H), 3.96(q, 2H), 1.41(t, 3H) | 460(12), 293(48), 149(100), 141(53) |
| 45 | cis | CH | F | F | O | 3-(CH₃)₂CHO—C₆H₄ | H | 7.51–6.66(m, 10H), 5.19(d, 1H, E), 4.76(d, 1H, Z), 4.54–4.22(m, 4H), 3.92–3.49(m, 4H), 1.27(d, 6H) | 474(8), 279(84), 223(83), 140(100), 127(30), 81(31) |
| 46 | cis | CH | F | F | O | 3,4-OCH₂O—C₆H₃ | H | 7.58–6.66(m, 9H), 5.94(s, 2H), 5.20(d, 1H, E), 4.77(d, 1H, Z), 4.39–4.26(m, 3H), 3.96–3.52(m, 4H) | 460(9), 215(44), 141(100), 57(74) |
| 47 | cis | CH | F | F | O | 4-Cl—C₆H₄ | H | 7.52–6.78(m, 10H), 5.18(d, 1H, E), 4.73(d, 1H, Z), 4.39–4.30(m, 3H), 3.92–3.48(m, 4H) | 450(13), 223(66), 141(100), 81(26) |
| 48 | cis | CH | F | F | O | 3-F—C₆H₄ | H | 7.60–6.80(m, 10H), 5.21(d, 1H, E), 4.75(d, 1H, Z), 4.41–4.18(m, 3H), 3.94–3.52(m, 4H) | 434(16), 279(75), 223(71), 141(100), 127(60) |
| 49 | cis | CH | F | F | O | 4-F—C₆H₄ | H | 7.59–6.81(m, 10H), 5.20(d, 1H, E), 4.73(d, 1H, Z), 4.43–4.17(m, 3H), 3.92–3.50(m, 4H) | 434(25), 279(60), 223(30), 141(100), 127(74) |
| 50 | cis | CH | F | F | O | 3-CH₃-4-Cl—C₆H₃ | H | 7.47–6.78(m, 9H), 5.15(d, 1H, E), 4.68(d, 1H Z), 4.40–4.13(m, 4H), 3.94–3.51(m, 4H), 2.33(s, 3H) | 464(54), 279(15), 157(32), 141(100), 81(55) |

TABLE VII-continued (I)

[Structure of compound (I) with R³, R⁴, F, Y, dioxolane ring, imidazole, and phenyl with R¹, R² substituents]

A: [1,4-disubstituted phenyl structure with O]

B: [phenyl-piperazine-N structure]

| Ex. | stereo | X | R¹ | R² | Y | R³ | R⁴ | ¹H-NMR (CDCl₃, TMS) δ (ppm) | MS(m/e) (M, int) |
|---|---|---|---|---|---|---|---|---|---|
| 51 | cis | CH | F | F | O | C₁₀H₇ | H | 7.99–6.63(m, 13H), 5.86(d, 1H, E), 5.37(d, 1H, Z), 4.40–4.12(m, 3H), 3.84–3.40(m, 4H) | 466(10), 279(26), 223(34), 158(85), 141(100), 80(54) |
| 52 | cis | CH | F | F | O | C₆H₅ | CF₃ | 7.47–6.77(m, 11H), 4.42–4.07(m, 3H), 4.00–3.38(m, 4H) | 484(16), 403(74), 140(100) |
| 53 | cis | CH | F | F | O | 3-CH₃—C₆H₄ | CF₃ | 7.47–6.77(m, 10H), 4.37–4.12(m, 3H), 3.93–3.37(m, 4H), 2.32(s, 3H) | 498(11), 417(12), 219(81), 141(100), 81(35) |
| 54 | cis | CH | F | F | O | 4-CH₃—C₆H₄ | CF₃ | 7.77–6.79(m, 10H), 4.41–4.03(m, 3H), 3.97–3.37(m, 4H), 2.34(s, 3H) | 498(11), 167(34), 149(100), 71(52), 57(77), 43(60) |
| 55 | cis | CH | F | F | O | 4-C₂H₅—C₆H₄ | CF₃ | 7.42–6.75(m, 10H), 4.31–4.06(m, 3H), 3.91–3.30(m, 4H), 2.57(q, 2H), 1.78(t, 3H) | 512(49), 431(40), 167(35), 149(100), 141(60) |
| 56 | cis | CH | F | F | O | 3,4-(CH₃)₂—C₆H₃ | CF₃ | 7.48–6.78(m, 9H), 4.37–4.12(m, 3H), 3.96–3.39(m, 4H), 2.25(s, 6H) | 512(26), 431(11), 223(36), 141(100), 82(47) |
| 57 | cis | CH | F | F | O | 3,5-(CH₃)₂—C₆H₃ | CF₃ | 7.71–6.78(m, 9H), 4.43–4.12(m, 3H), 4.00–3.38(m, 4H), 2.35(s, 6H) | 512(58), 431(35), 140(100) |
| 58 | cis | CH | F | F | O | 3-CF₃—C₆H₄ | CF₃ | 7.66–6.78(m, 10H), 4.35–4.11(m, 3H), 3.87–3.33(m, 4H) | 552(10), 471(12), 279(16), 167(29), 149(100) |
| 59 | cis | CH | F | F | O | 4-CF₃—C₆H₄ | CF₃ | 7.72–6.83(m, 10H), 4.39–4.15(m, 3H), 3.91–3.30(m, 4H) | 552(40), 471(41), 279(10), 149(100), 141(82) |
| 60 | cis | CH | F | F | O | 3-CH₃O—C₆H₄ | CF₃ | 7.47–6.78(m, 10H), 4.35–4.02(m, 3H), 3.84–3.39(m, 4H), 3.75(s, 3H) | 514(24), 433(36), 223(20), 141(100) |
| 61 | cis | CH | F | F | O | 4-CH₃O—C₆H₄ | CF₃ | 7.59–6.78(m, 10H), 4.42–4.08(m, 3H), 4.00–3.38(m, 4H), 3.77(s, 3H) | 514(60), 433(53), 279(81), 140(100) |
| 62 | cis | CH | F | F | O | 3,4-OCH₂O—C₆H₃ | CF₃ | 7.78–6.68(m, 9H), 5.97(s, 2H), 4.40–4.07(m, 3H), 3.98–3.37(m, 4H) | 528(44), 223(37), 148(100), 140(72), 57(49) |
| 63 | cis | CH | F | F | O | 4-C₆H₅O—C₆H₄ | CF₃ | 7.50–6.80(m, 15H), 4.45–4.12(m, 3H), 3.98–3.36(m, 4H) | 576(26), 495(41), 279(76), 223(66), 141(100) |
| 64 | cis | CH | F | F | O | 3-Cl—C₆H₄ | CF₃ | 7.78–6.78(m, 10H), 4.41–4.07(m, 3H), 3.99–3.37(m, 4H) | 518(8), 437(45), 140(100) |
| 65 | cis | CH | F | F | O | 3-F—C₆H₄ | CF₃ | 7.49–6.78(m, 10H), 4.37–4.12(m, 3H), 3.94–3.38(m, 4H) | 502(27), 421(43), 279(15), 141(100) |
| 66 | cis | CH | F | F | O | 4-F—C₆H₄ | CF₃ | 7.76–6.80(m, 10H), 4.42–4.05(m, 3H), 4.00–3.38(m, 4H) | 502(21), 421(68), 148(58), 140(100) |
| 67 | cis | CH | F | F | O | 3,5-Cl₂—C₆H₃ | CF₃ | 7.78–6.78(m, 9H), 4.48–4.10(m, 3H), 3.98–3.36(m, 4H) | 552(11), 471(41), 140(100) |
| 68 | cis | CH | F | F | O | C₆H₅S | CF₃ | 7.42–6.72(m, 9H), 4.30–4.08(m, 3H), 4.00–3.43(m, 4H) | 490(41), 279(93), 223(89), |

TABLE VII-continued

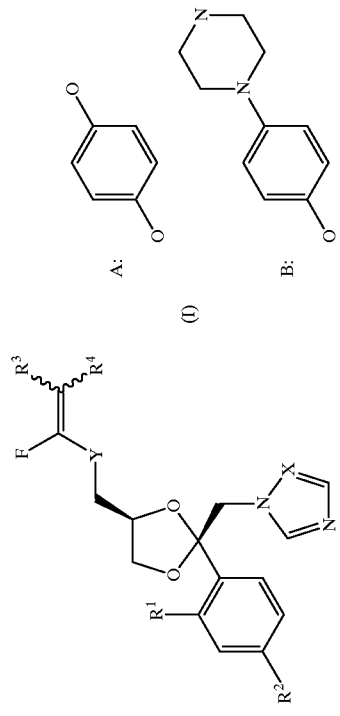

(I)

A: [4-hydroxyphenyl structure]

B: [4-(4-morpholinyl)phenyl structure]

| Ex. | stereo | X | R¹ | R² | Y | R³ | R⁴ | ¹H-NMR (CDCl₃, TMS) δ (ppm) | MS(m/e) (M, int) |
|---|---|---|---|---|---|---|---|---|---|
| 69 | cis | N | Cl | Cl | O | C₆H₅ | H | 8.11(s, 1H), 7.87(s, 1H), 7.58–7.09(m, 8H), 5.28(d, 1H, E), 4.84(d, 1H, Z), 4.83–4.65(m, 2H), 4.32(m, 1H), 4.02–3.65(m, 4H) | 141(100), 449(25), 312(45), 173(83), 109(100), 57(61) |
| 70 | cis | N | Cl | Cl | O | 3-CH₃—C₆H₄ | H | 8.12(s, 1H), 7.88(s, 1H), 7.54–6.98(m, 7H), 5.25(d, 1H, E), 4.81(d, 1H, Z), 4.84–4.67(m, 2H), 4.35(m, 1H), 4.00–3.69(m, 4H), 2.36(s, 3H) | 463(43), 381(100), 173(16) |
| 71 | cis | N | Cl | Cl | O | 4-CH₃—C₆H₄ | H | 8.11(s, 1H), 7.87(s, 1H), 7.51–7.03(m, 7H), 5.25(d, 1H, E), 4.81(d, 1H, Z), 4.85–4.68(m, 1H), 4.34(m, 1H), 3.98–3.70(m, 4H), 2.34(s, 3H) | 463(21), 312(96), 173(84), 123(100), 108(53), 57(55) |
| 72 | cis | N | Cl | Cl | O | 4-C₂H₅—C₆H₄ | H | 8.11(s, 1H), 7.84(s, 1H), 7.50–7.01(m, 7H), 5.26(d, 1H, E), 4.82(d, 1H, Z), 4.86–4.65(m, 2H), 4.34(m, 1H), 4.00–3.66(m, 4H), 2.60(q, 2H), 1.21(t, 3H) | 477(48), 395(42), 312(67), 173(100), 137(55), 108(50) |
| 73 | cis | N | Cl | Cl | O | 3,5-(CH₃)₂—C₆H₃ | H | 8.10(s, 1H), 7.85(s, 1H), 7.50–6.82(m, 6H), 5.21(d, 1H, E), 4.77(d, 1H, Z), 4.89–4.66(m, 2H), 4.32(m, 1H), 3.98–3.70(m, 4H), 2.39(s, 6H) | 477(26), 312(100), 173(83), 137(75), 108(58), 57(88) |
| 74 | cis | N | Cl | Cl | O | 4-CH₃O—C₆H₄ | H | 8.09(s, 1H), 7.83(s, 1H), 7.49–6.81(m, 7H), 5.21(d, 1H, E), 4.77(d, 1H, Z), 4.84–4.65(m, 2H), 4.31(m, 1H), 3.95–3.65(m, 4H), 3.76(s, 3H) | 479(42), 312(39), 173(50), 139(100), 57(40) |
| 75 | cis | N | Cl | Cl | O | 3,4-OCH₂O—C₆H₃ | H | 8.16(s, 1H), 7.83(s, 1H), 7.51–6.73(m, 6H), 5.93(s, 2H), 5.20(d, 1H, E), 4.76(d, 1H, Z), 4.90–4.68(m, 2H), 4.33(m, 1H), 3.98–3.63(m, 4H) | 493(62), 312(70), 173(68), 153(100), 108(41), 57(81) |
| 76 | cis | N | Cl | Cl | O | 4-Cl—C₆H₄ | H | 8.14(s, 1H), 7.87(s, 1H), 7.64–7.07(m, 7H), 5.22(d, 1H, E), 4.78(d, 1H, Z), 4.92–4.68(m, 2H), 4.36(m, 1H), 4.01–3.68(m, 4H) | 483(27), 312(65), 173(100), 143(56), 57(58) |
| 77 | cis | N | Cl | Cl | O | 4-F—C₆H₄ | H | 8.11(s, 1H), 7.85(s, 1H), 7.58–6.87(m, 7H), 5.21(d, 1H, E), 4.79(d, 1H, Z), 4.89–4.66(m, 2H), 4.34(m, 1H), 3.97–3.62(m, 4H) | 467(15), 312(37), 173(84), 127(100), 108(42), 57(55) |
| 78 | cis | N | Cl | Cl | O | C₁₀H₇ | H | 8.04(s, 1H), 7.86(s, 1H), 7.84–6.95(m, 10H), 5.86(d, 1H, E), 5.41(d, 1H, Z), 4.73–4.50(m, 2H), 4.14(m, 1H), 3.94–3.54(m, 4H) | 499(20), 312(74), 173(55), 159(100), 108(39), 57(59) |
| 79 | cis | N | Cl | Cl | O | C₆H₅ | CF₃ | 8.20–7.83(m, 2H), 7.61–7.11(m, 8H), 4.87–4.52(m, 2H), 4.41–3.42(m, 5H) | 517(21), 435(40), 173(100), 127(42), 57(64) |
| 80 | cis | N | Cl | Cl | O | 3-CH₃—C₆H₄ | CF₃ | 821–7.84(m, 2H), 7.54–7.04(m, 7H), 4.90–4.50(m, 2H), 4.42–3.50(m, 5H), 2.36(s, 3H) | 531(53), 312(48), 173(100), 57(68) |
| 81 | cis | N | Cl | Cl | O | 4-CH₃—C₆H₄ | CF₃ | 820–7.85(m, 2H), 7.58–7.09(m, 7H), 4.90–4.52(m, 2H), 4.44–3.51(m, 5H), 2.35(s, 3H) | 531(40), 312(66), 173(100), 141(44), 108(41), 57(89) |
| 82 | cis | N | Cl | Cl | O | 3,4-(CH₃)₂—C₆H₃ | CF₃ | 8.19–7.82(m, 2H), 7.56–6.97(m, 6H), 4.90–4.50(m, 2H), 4.41–3.51(m, 5H), 2.28(s, 3H), 2.19(s, 3H) | 545(37), 314(45), 312(78), 173(100), 57(92), 43(68) |
| 83 | cis | N | C | Cl | O | 3,5-(CH₃)₂—C₆H₃ | CF₃ | 8.19–7.83(m, 2H), 7.57–6.87(m, 6H), 4.91–4.52(m, 2H), 4.42–3.49(m, 5H), 2.31(s, 3H), 2.29(s, 3H) | 545(41), 312(69), 173(100), 57(44) |
| 84 | cis | N | Cl | Cl | O | 4-CH₃O—C₆H₄ | CF₃ | 8.19–7.84(m, 2H), 7.54–6.75(m, 7H), 4.89–4.54(m, 2H), 4.43–3.41(m, 5H), 3.74(s, 3H) | 547(27), 465(73), 312(58), 173(100), 57(72) |

TABLE VII-continued

A: (4-hydroxyphenyl structure)
B: (4-(4-morpholinyl)phenyl structure)

Structure (I): imidazole-containing dioxolane with fluoroalkene substituent bearing R¹, R², R³, R⁴ groups and Y linker.

| Ex. | stereo | X | R¹ | R² | Y | R³ | R⁴ | ¹H-NMR (CDCl₃, TMS) δ (ppm) | MS(m/e) (M, int) |
|---|---|---|---|---|---|---|---|---|---|
| 85 | cis | N | Cl | Cl | O | 4-C₂H₅O—C₆H₄ | CF₃ | 8.18–7.83(m, 2H), 7.52–6.78(m, 7H), 4.88–4.52(m, 2H), 4.41–3.40(m, 7H), 1.39(t, 3H) | 561(31), 479(70), 312(100), 173(38), 108(55) |
| 86 | cis | N | Cl | Cl | O | 4-Cl—C₆H₄ | CF₃ | 8.19–7.83(m, 2H), 7.54–6.75(m, 7H), 4.89–4.51(m, 2H), 4.41–3.50(m, 5H) | 551(52), 465(51), 225(62), 173(100), 82(66) |
| 87 | cis | N | Cl | Cl | O | 4-F—C₆H₄ | CF₃ | 8.20–7.87(m, 2H), 7.60–6.96(m, 7H), 4.90–4.59(m, 2H), 4.45–3.47(m, 5H) | 535(52), 453(38), 173(100), 145(54), 57(55), 41(51) |
| 88 | cis | CH | Cl | Cl | A | C₆H₅ | H | 7.68–6.77(m, 15H), 5.63(d, 1H, E), 5.18(d, 1H, Z), 4.59–4.10 (m, 3H), 3.92–3.62(m, 3H), 3.29–3.21(m, 1H) | 541(17), 506(59), 269(29), 131(84), 109(100) |
| 89 | cis | CH | Cl | Cl | A | 4-CH₃—C₆H₄ | H | 7.69–6.70(m, 14H), 5.61(d, 1H, E), 5.18(d, 1H, Z), 4.59–4.11 (m, 3H), 3.92–3.62(m, 3H), 3.29–3.21(m, 1H), 2.31(s, 3H) | 555(20), 520(48), 486(61), 151(41), 131(51), 123(100) |
| 90 | cis | CH | Cl | Cl | A | 3-CH₃O—C₆H₄ | H | 7.70–6.71(m, 14H), 5.60(d, 1H, E), 5.15(d, 1H, Z), 4.60–4.18 (m, 3H), 3.88–3.64(m, 3H), 3.28–3.20(m, 1H), 3.74(s, 3H) | 571(19), 536(29), 502(45), 139(100), 105(66) |
| 91 | cis | CH | Cl | Cl | A | 3-Cl—C₆H₄ | H | 7.69–6.76(m, 14H), 5.53(d, 1H, E), 5.05(d, 1H, Z), 4.59–4.18(m, 3H), 3.92–3.61(m, 3H), 3.28–3.19(m, 1H), 3.54–3.41(m, 1H), 2.35(3H, s) | 576(17), 540(23), 506(34), 425(12), 131(100) |
| 92 | cis | CH | Cl | Cl | A | 4-F—C₆H₄ | H | 7.68–6.74(m, 14H), 5.59(d, 1H, E), 5.13(d, 1H, Z), 4.58–4.18(m, 3H), 3.87–3.61(m, 3H), 3.26–3.15(m, 1H) | 559(27), 524(35), 490(29), 155(16), 105(100) |
| 93 | cis | CH | Cl | Cl | A | C₆H₅ | CF₃ | 7.56–6.72(m, 15H), 4.34–4.18(m, 3H), 3.86–3.60(m, 3H), 3.27–3.16(m, 1H) | 609(15), 540(25), 131(90), 105(100), 77(45) |
| 94 | cis | CH | Cl | Cl | A | 4-CH₃—C₆H₄ | CF₃ | 7.57–6.72(m, 14H), 4.34–4.19(m, 3H), 3.75–3.65(m, 3H), 3.30–3.10(m, 1H), 2.36(s, 3H) | 623(13), 473(10), 295(85), 167(32), 148(100), 71(33) |
| 95 | cis | CH | Cl | Cl | A | 4-C₂H₅—C₆H₄ | CF₃ | 7.45–6.64(m, 14H), 4.48–4.10(m, 3H), 3.77–3.54(m, 3H), 3.20–3.05(m, 1H), 2.58(q, 2H), 1.16(t, 3H) | 637(10), 568(64), 217(15), 131(69), 105(100) |
| 96 | cis | CH | Cl | C | A | 3-CF₃—C₆H₄ | CF₃ | 7.63–6.65(m, 14H), 4.45–4.03(m, 3H), 3.80–3.54(m, 3H), 3.16–3.13(m, 1H) | 677(16), 595(42), 561(100), 405(68), 173(21), 132(97) |
| 97 | cis | CH | Cl | Cl | A | 4-CF₃—C₆H₄ | CF₃ | 7.75–6.70(m, 14H), 4.58–4.10(m, 3H), 3.95–3.66(m, 3H), 3.25–3.12(m, 1H) | 677(38), 561(11), 405(21), 172(15), 131(80), 105(100) |
| 98 | cis | CH | Cl | Cl | A | 4-CH₃O—C₆H₄ | CF₃ | 7.52–6.72(m, 14H), 4.52–4.19(m, 3H), 3.82–3.62(m, 3H), 3.32–3.18(m, 1H), 3.81(s, 3H) | 639(64), 489(43), 235(100), 131(44), 105(98) |
| 99 | cis | CH | Cl | Cl | A | 3,4-OCH₂O—C₆H₃ | CF₃ | 7.72–6.71(m, 13H), 6.00(s, 2H), 4.48–4.20(m, 3H), 3.87–3.66(m, 3H), 3.30–3.10(m, 1H) | 653(20), 584(100), 131(64), 105(64) |
| 100 | cis | CH | Cl | Cl | A | 4-C₆H₅O—C₆H₄ | CF₃ | 7.52–6.63(m, 15H), 4.50–4.08(m, 3H), 3.75–3.54(m, 3H), 3.20–3.00(m, 1H) | 702(26), 539(100), 297(70), 131(52), 105(62) |

TABLE VII-continued

Structure (I):

Group A:

Group B:

| Ex. | stereo | X | R¹ | R² | Y | R³ | R⁴ | ¹H-NMR (CDCl₃, TMS) δ (ppm) | MS(m/e) (M, int) |
|---|---|---|---|---|---|---|---|---|---|
| 101 | cis | CH | Cl | Cl | A | 3-Cl—C₆H₄ | CF₃ | 7.70–6.72(m, 14H), 4.59–4.19(m, 3H), 3.90–3.55(m, 3H), 3.26–3.08(m, 1H) | 644(50), 563(11), 493(81), 132(100), 104(38) |
| 102 | cis | CH | Cl | Cl | A | 4-Cl—C₆H₄ | CF₃ | 7.46–6.65(m, 14H), 4.26–4.02(m, 3H), 3.81–3.50(m, 3H), 3.17–3.09(m, 1H) | 644(12), 608(14), 493(100), 371(27), 104(59) |
| 103 | cis | CH | Cl | Cl | A | 3-F—C₆H₄ | CF₃ | 7.68–6.73(m, 14H), 4.51–4.10(m, 3H), 3.88–3.59(m, 3H), 3.23–3.12(m, 1H) | 627(40), 546(45), 477(55), 149(35), 132(100), 105(88) |
| 104 | cis | CH | Cl | Cl | A | 3,5-Cl₂—C₆H₃ | CF₃ | 7.69–6.75(m, 13H), 4.52–4.18(m, 3H), 3.91–3.60(m, 3H), 3.21–3.13(m, 1H) | 678(13), 597(28), 527(40), 131(100), 105(79) |
| 105 | cis | CH | Cl | Cl | A | 4-CH₃O—C₆H₄ | H | 7.53–6.71(m, 14H), 5.59(d, 1H, E), 5.14(d, 1H, Z), 4.42–4.32(m, 3H), 3.91–3.61(m, 3H), 3.25–3.17(m, 1H), 3.72(s, 3H) | 538(100), 457(35), 167(29), 140(61) |
| 106 | cis | CH | F | F | A | C₆H₅ | CF₃ | 7.64–6.70(m, 15H), 4.48–4.30(m, 3H), 3.97–3.85(m, 1H), 3.78–3.69(m, 2H), 3.25–3.10(m, 1H) | 576(9), 495(19), 141(91), 131(100), 81(18) |
| 107 | cis | CH | F | F | A | 3-CH₃—C₆H₄ | CF₃ | 7.54–6.71(m, 14H), 4.44–4.34(m, 3H), 3.96–3.62(m, 3H), 3.24–3.16(m, 1H), 2.36(s, 3H) | 590(50), 509(24), 351(28), 149(20), 141(100) |
| 108 | cis | CH | F | F | A | 4-C₂H₅—C₆H₄ | CF₃ | 7.57–6.71(m, 14H), 4.44–4.26(m, 3H), 3.96–3.59(m, 3H), 3.27–3.12(m, 1H), 2.66(q, 2H), 1.24t, 3H) | 604(38), 523(53), 365(12), 141(100), 131(59) |
| 109 | cis | CH | F | F | A | 4-t-C₄H₉—C₆H₄ | CF₃ | 7.57–6.72(m, 14H), 4.44–4.28(m, 3H), 3.91–3.60(m, 3H), 3.27–3.15(m, 1H), 1.30(s, 9H) | 632(68), 551(39), 393(25), 268(31), 57(100) |
| 110 | cis | CH | F | F | A | 3,4-(CH₃)₂—C₆H₃ | CF₃ | 7.49–6.67(m, 13H), 4.38–4.21(m, 3H), 3.90–3.54(m, 3H), 3.19–3.11(m, 1H), 2.21(s, 6H) | 604(27), 523(19), 141(100), 131(49), 91(29) |
| 111 | cis | CH | F | F | A | 3-CF₃—C₆H₄ | CF₃ | 7.61–6.71(m, 14H), 4.44–4.26(m, 3H), 3.94–3.58(m, 3H), 3.22–3.10(m, 1H) | 644(16), 563(82), 405(35), 141(100), 131(96) |
| 112 | cis | CH | F | F | A | 3,4-OCH₂O—C₆H₃ | CF₃ | 7.54–6.71(m, 14H), 5.96(s, 2H), 4.43–4.26(m, 3H), 3.95–3.58(m, 3H), 3.26–3.11(m, 1H) | 620(61), 539(19), 381(17), 141(100), 131(45) |
| 113 | cis | CH | F | F | A | 4-C₆H₅O—C₆H₄ | CF₃ | 7.55–6.72(m, 19H), 4.44–4.27(m, 3H), 3.96–3.59(m, 3H), 3.20–3.12(m, 1H) | 668(21), 587(12), 575(69), 141(100), 131(37) |
| 114 | cis | CH | F | F | A | 3-Cl—C₆H₄ | CF₃ | 7.57–6.72(m, 14H), 4.44–4.26(m, 3H), 3.96–3.58(m, 3H), 3.23–3.11(m, 1H) | 611(10), 529(51), 371(40), 141(100) |
| 115 | cis | CH | F | F | A | 3-F—C₆H₄ | CF₃ | 7.57–6.72(m, 14H), 4.44–4.26(m, 3H), 3.96–3.58(m, 3H), 3.23–3.11(m, 1H) | 594(41), 513(56), 355(35), 141(99), 132(100) |
| 116 | cis | CH | F | F | A | 3,5-Cl₂—C₆H₃ | CF₃ | 7.55–6.74(m, 13H), 4.40–4.34(m, 3H), 3.95–3.59(m, 3H), 3.16–3.15(m, 1H) | 645(39), 563(26), 141(100), 131(88), 81(16) |

TABLE VII-continued

Structure (I):

Group A:
4-hydroxyphenyl (phenol with para-OH)

Group B:
4-(4-morpholinyl)phenyl group

| Ex. | stereo | X | R¹ | R² | Y | R³ | R⁴ | ¹H-NMR (CDCl₃, TMS) δ (ppm) | MS(m/e) (M, int) |
|---|---|---|---|---|---|---|---|---|---|
| 117 | cis | CH | F | F | A | C₄H₃S | CF₃ | 7.71–6.72(m, 13H), 4.50–4.27(m, 3H), 3.95–3.60(m, 4H), 3.23–3.13(m, 1H) | 582(44), 501(19), 211(36), 141(100), 131(76) |
| 118 | cis | N | Cl | Cl | A | 4-CH₃O—C₆H₄ | H | 8.21(s, 1H), 7.81(s, 1H), 7.62–6.63(m, 11H), 5.52(d, 1H, E), 5.06(d, 1H, Z), 4.84–4.64(m, 2H), 4.32–4.22(m, 1H) 3.87–3.60(m, 3H), 3.43–3.35(m, 1H), 3.66(s, 3H) | 572(8), 537(26), 279(13), 172(48), 139(100) |
| 119 | cis | N | Cl | Cl | A | C₆H₅ | CF₃ | 8.19(s, 1H), 7.88(s, 1H), 7.70–6.73(m, 12H), 4.87–4.69(m, 2H), 4.42–4.31(m, 1H), 3.68–3.53(m, 3H), 3.51–3.36(m, 1H) | 610(15), 527(25), 337(36), 173(36), 132(100) |
| 120 | cis | N | Cl | C | A | 4-CH₃—C₆H₄ | CF₃ | 8.21(s, 1H), 7.90(s, 1H), 7.72–6.75(m, 11H), 4.89–4.70(m, 2H), 4.43–4.30(m 1H), 4.00–3.70(m, 3H), 3.54–3.41(m, 1H), 2.35(s, 3H) | 624(8), 541(35), 351(58), 173(57), 131(100) |
| 121 | cis | N | Cl | Cl | A | 4-CH₃O—C₆H₄ | CF₃ | 8.21(s, 1H), 7.90(s, 1H), 7.71–6.74(m, 11H), 3.52–3.39(m, 1H), 3.79(s, 3H), 4.45–4.31(m, 1H), 3.98–3.68(m, 3H), 4.81–4.71(m, 2H) | 640(6), 605(12), 557(25), 235(100), 173(37) |
| 122 | cis | N | Cl | Cl | A | 4-Cl—C₆H₄ | CF₃ | 8.20(s, 1H), 7.87(s, 1H), 7.69–6.69(m, 11H), 4.86–4.68(m, 2H), 4.40–4.28(m, 1H), 3.93–3.68(m, 3H), 3.50–3.39(m, 1H) | 645(25), 610(39), 563(33), 173(38), 132(100) |
| 123 | cis | N | Cl | Cl | A | 4-F—C₆H₄ | CF₃ | 8.19(s, 1H), 7.88(s, 1H), 7.66–6.68(m, 11H), 4.87–4.70(m, 2H), 4.45–4.30(m, 1H), 3.99–3.66(m, 3H), 3.59–3.30(m, 1H) | 628(16), 545(32), 355(37), 173(49), 132(100) |
| 124 | cis | CH | Cl | Cl | B | C₆H₅ | CF₃ | 7.59–6.72(m, 15H), 4.65–4.27(m, 3H), 4.06–3.37(m, 7H), 3.28–2.79(m, 4H), 2.40–2.27(m, 1H) | 677(53), 428(47), 279(13), 149(47), 84(25), 43(100) |
| 125 | cis | CH | Cl | Cl | B | 3-CH₃—C₆H₄ | CF₃ | 7.60–6.69(m, 14H), 4.54–4.27(m, 3H), 4.04–3.35(m, 7H), 3.29–2.78(m, 4H), 2.52–2.10(m, 1H), 2.36(s, 3H) | 691(28), 217(73), 203(13), 91(100) |
| 126 | cis | CH | Cl | Cl | B | 4-CH₃—C₆H₄ | CF₃ | 7.59–6.68(m, 14H), 4.56–4.27(m, 3H), 4.06–3.34(m, 7H), 3.27–2.79(m, 4H), 2.46–2.24(m, 1H), 2.35(s, 3H) | 691(48), 471(29), 173(76), 77(100) |
| 127 | cis | CH | Cl | Cl | B | 4-C₂H₅—C₆H₄ | CF₃ | 7.59–6.67(m, 14H), 4.53–4.26(m, 3H), 4.04–3.30(m, 7H), 3.27–2.80(m, 4H), 2.66(q, 2H), 2.46–2.39(m, 1H), 1.25(t, 3H) | 705(35), 489(31), 217(22), 81(27), 44(100) |
| 128 | cis | CH | Cl | Cl | B | 4-t-C₄H₉—C₆H₄ | CF₃ | 7.73–6.72(m, 14H), 4.54–4.23(m, 3H), 3.96–3.30(m, 7H), 3.27–2.82(m, 4H), 2.49–2.36(m, 1H), 1.31(s, 9H) | 733(21), 663(30), 293(51), 149(56), 81(17), 57(100) |
| 129 | cis | CH | Cl | Cl | B | 3,4-(CH₃)₂—C₆H₃ | CF₃ | 7.60–6.72(m, 13H), 4.54–4.27(m, 3H), 4.02–3.34(m, 7H), 3.28–2.84(m, 4H), 2.54–2.39(m, 1H), 2.32(s, 6H) | 705(18), 504(26), 148(21), 84(100) |
| 130 | cis | CH | Cl | Cl | B | 4-CF₃—C₆H₄ | CF₃ | 7.73–6.68(m, 13H), 4.74–4.26(m, 3H), 4.00–3.35(m, 7H), 3.30–2.78(m, 4H), 2.59–2.36(m, 1H) | 745(10), 503(28), 257(21), 149(100), 71(36) |
| 131 | cis | CH | Cl | Cl | B | 4-CH₃O—C₆H₄ | CF₃ | 7.59–6.69(m, 14H), 4.53–4.26(m, 3H), 4.05–3.34(m, 7H), 3.81(s, 3H), 3.29–2.80(m, 4H), 2.49–2.38(m, 1H) | 707(16), 504(34), 429(26), 281(46), 149(22), 84(100) |
| 132 | cis | CH | C | Cl | B | 3,4-OCH₂O—C₆H₃ | CF₃ | 7.60–6.70(m, 13H), 5.99(s, 2H), 4.54–4.27(m, 3H), 4.03–3.38(m, 7H), 3.30–2.82(m, 4H), 2.59–2.44(m, 1H) | 721(30), 503(52), 355(25), 221(33), 149(54), 57(100) |

TABLE VII-continued

A:

B:

(I)

| Ex. | stereo | X | R¹ | R² | Y | R³ | R⁴ | ¹H-NMR (CDCl₃, TMS) δ (ppm) | MS(m/e) (M, int) |
|---|---|---|---|---|---|---|---|---|---|
| 133 | cis | CH | Cl | Cl | B | 3-Cl—C₆H₄ | CF₃ | 7.74–6.60(m, 14H), 4.54–4.23(m, 3H), 4.00–3.43(m, 7H), 4H), 2.58–2.42(m, 1H) | 711(17), 538(79), 140(100), 131(47) |
| 134 | cis | CH | Cl | Cl | B | 4-Cl—C₆H₄ | CF₃ | 7.68–6.69(m, 14H), 4.56–4.27(m, 3H), 4.04–3.33(m, 7H), 4H), 2.58–2.40(m, 1H) | 712(13), 279(75), 223(16), 167(25), 149(86), 57(100) |
| 135 | cis | CH | Cl | Cl | B | 4-F—C₆H₄ | CF₃ | 7.70–6.65(m, 14H), 4.65–4.26(m, 3H), 4.04–3.36(m, 7H), 4H), 2.59–2.42(m, 1H) | 695(10), 429(19), 207(56), 149(11), 83(99), 43(100) |
| 136 | cis | CH | Cl | Cl | B | 3,5-Cl₂—C₆H₃ | CF₃ | 7.60–6.60(m, 14H), 4.60–4.24(m, 3H), 3.86–3.34(m, 7H), 4H), 2.60–2.40(m, 1H) | 746(13), 503(13), 149(100), 70(51) |
| 137 | cis | CH | Cl | Cl | B | C₄H₃S | CF₃ | 7.60–6.70(m, 13H), 4.94–4.25(m, 3H), 4.03–3.45(m, 4H), 1H), 2.69–2.52(m, 1H) | 683(44), 503(14), 429(46), 149(38), 73(100) |
| 138 | cis | CH | Cl | Cl | B | C₆H₅ | CF₃ | 7.60–6.68(m, 15H), 4.53–4.33(m, 3H), 3.30–2.80(m, 7H), 4H), 2.45–2.28(m, 1H) | 644(15), 371(17), 315(42), 43(100) |
| 139 | cis | CH | C | Cl | B | 3-CH₃—C₆H₄ | CF₃ | 7.50–6.60(m, 14H), 4.48–4.10(m, 3H), 3.95–3.20(m, 7H), 4H), 2.40–2.23(m, 1H), 2.30(s, 3H) | 658(28), 439(53), 426(42), 44(100) |
| 140 | cis | CH | F | F | B | 4-n-C₄H₉—C₆H₄ | CF₃ | 7.55–6.72(m, 14H), 4.57–4.26(m, 3H), 4.05–3.29(m, 7H), 3.24–2.80 (m, 4H), 2.61(t, 2H), 2.46–2.30(m, 1H), 1.45–1.20(m, 4H), 0.91(t, 3H) | 700(10), 455(15), 141(39), 82(28), 44(100) |
| 141 | cis | CH | F | F | B | 3,5-(CH₃)₂—C₆H₃ | CF₃ | 7.58–6.69(m, 13H), 4.44–4.26(m, 3H), 4.00–3.30(m, 7H), 3.28–2.84(m, 4H), 2.53–2.28(m, 1H), 2.32(s, 6H) | 672(18), 440(61), 428(42), 354(18), 223(39), 141(100) |
| 142 | cis | CH | F | F | B | 4-CF₃—C₆H₄ | CF₃ | 7.74–6.70(m, 14H), 4.74–4.26(m, 3H), 4.00–3.34(m, 7H), 3.28–2.73(m, 4H), 2.59–2.43(m, 1H) | 712(29), 439(61), 426(16), 57(30), 44(100) |
| 143 | cis | CH | F | F | B | 3-CH₃O—C₆H₄ | CF₃ | 7.54–6.60(m, 14H), 4.49–4.18(m, 3H), 3.94–3.30(m, 7H), 3.72(s, 3H), 3.20–2.64(m, 4H), 2.43–2.25(m, 1H) | 674(10), 503(18), 293(27), 148(99), 57(100) |
| 144 | cis | CH | F | F | B | 4-CH₃O—C₆H₄ | CF₃ | 7.60–6.68(m, 14H), 4.53–4.28(m, 3H), 4.08–3.35(m, 7H), 3.81(s, 3H), 3.30–2.70(m, 4H), 2.50–2.36(m, 1H) | 674(30), 455(69), 439(61), 44(100) |
| 145 | cis | CH | F | F | B | 3,4-OCH₂O—C₆H₃ | CF₃ | 7.56–6.98(m, 13H), 5.98(s, 2H), 4.46–4.25(m, 3H), 4.00–3.30(m, 7H), 3.24–2.80(m, 4H), 2.57–2.40(m, 1H) | 688(7), 605(18), 439(49), 228(28), 141(60), 44(100) |
| 146 | cis | CH | F | F | B | 4-C₆H₅O—C₆H₄ | CF₃ | 7.57–6.70(m, 19H), 4.56–4.27(m, 3H), 4.02–3.35(m, 7H), 3.26–2.83(m, 4H), 2.54–2.43(m, 1H) | 736(37), 483(26), 251(41), 77(33), 44(100) |
| 147 | cis | CH | F | F | B | 3-F—C₆H₄ | CF₃ | 7.56–6.64(m, 14H), 4.59–4.26(m, 3H), 4.00–3.32(m, 7H), 3.25–2.83(m, 4H), 2.58–2.39(m, 1H) | 662(42), 426(32), 141(18), 81(20), 44(100) |
| 148 | cis | CH | F | F | B | 4-F—C₆H₄ | CF₃ | 7.57–6.70(m, 14H), 4.58–4.28(m, 3H), 4.04–3.28(m, 7H), 3.24–2.80(m, 4H), 2.53–2.35(m, 1H) | 662(37), 578(20), 455(17), 425(45), 170(100) |
| 149 | cis | CH | F | F | B | 4-Cl—C₆H₄ | CF₃ | 7.58–6.70(m, 14H), 4.57–4.28(m, 3H), 3.99–3.30(m, 7H), | 679(17), 610(18), 483(12), |

TABLE VII-continued
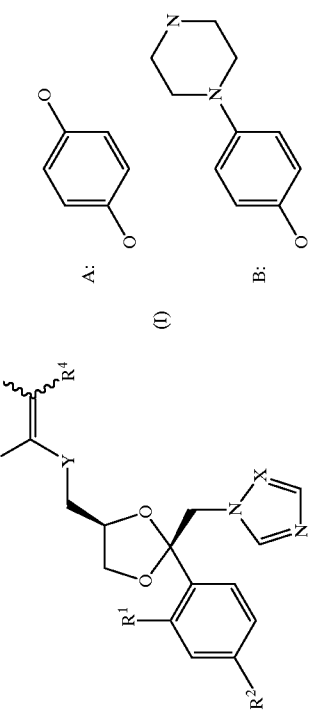
A: 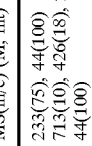
B: 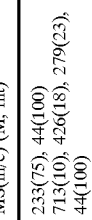
| Ex. | stereo | X | R$^1$ | R$^2$ | Y | R$^3$ | R$^4$ | $^1$H-NMR (CDCl$_3$, TMS) δ (ppm) | MS(m/e) (M, int) |
|---|---|---|---|---|---|---|---|---|---|
| 150 | cis | CH | F | F | B | 3,5-Cl$_2$—C$_6$H$_3$ | CF$_3$ | 3.26–2.80(m, 4H), 2.58–2.43(m, 1H) 7.60–6.70(m, 13H), 4.60–4.27(m, 3H), 3.94–3.33(m, 7H), 3.28–2.87(m, 4H), 2.74–2.59(m, 1H) | 233(75), 44(100) 713(10), 426(18), 279(23), 44(100) |

TEST EXAMPLE 1

Antifungal Activity

In vitro antifungal activities of the inventive antifungal compounds were evaluated using the test strains shown in Table VIII by the following microbroth dilution method which is a modified version of the procedure recommended by National Committee for the Clinical Laboratory Standards (see National Committee for Clinical Laboratory Standards, 1992, Reference methods for broth dilution antifungal susceptibility testing of yeasts, Proposed standard M27-P, National Committee for clinical laboratory standards, Villanova, Pa; and National Committee for Clinical Laboratory Standards, 1995, Reference methods for broth dilution antifungal susceptibility testing of yeasts. Tentative standard M27-T, National Committee for clinical laboratory standards, Villanova, Pa).

Sabourad Dextrose Agar(Difco) was used as a culture medium, and RPMI-1640 broth(Sigma. Co. w/L-glutamine, wo/NaHCO$_3$)(0.165 M MOPS, pH 7.0), as a dilution medium.

Each of the test strains were subcultured in Sabourad Dextrose Agar medium twice and a stain sample was taken from prominent colonies and suspended in sterile physiological saline solution in a cap tube. The turbidity of the suspension was adjusted to that of the Mcfarland 0.5 standard sample(approximately 10$^6$ CFU/ml). Then the suspension was diluted 500-fold with sterile RPMI-1640 liquid medium to 2×10$^3$ CFU/ml.

Each of the test compounds(the compounds obtained in Examples 1 to 150 and comparative compounds, i.e., fluconazole(FCZ) and itraconazole (ICZ)), was dissolved in DMSO to give a stock solution having a concentration of 4000 μg/ml and the stock solution was successively diluted to obtain test solutions having test compound concentrations of 200, 100, 50, 25, 12.5, 6.25, 3.13, 1.56, 0.78, 0.39, 0.20 and 0.10 μg/ml, respectively.

0.1 ml portion of the test solutions were added to the wells of a sterile 96 well plate. Then, 0.1 ml portion of each of the test strain solutions were added successively to the wells and the plate was incubated at 35° C. for 4 to 48 hours.

Minimal inhibitory concentration(MIC) of each compound was defined as the concentration of the test compound where no growth of the strain could be observed. The results are shown in Table IX.

TABLE VIII

| [001b]Strain (FUNGAL SPECIES) | Abbreviation |
|---|---|
| Candida albicans B. 02630 | C. albicans B. 02630 |
| Candida albicans A. 10231 | C. albicans A. 10231 |
| Candida albicans C1-2 | C. albicans C1-2 |
| Candida albicans IFO. 1385 | C. albicans IFO. 1385 |
| Candida tropicalis A. 13803 | C. tropicalis A. 13803 |
| Candida pseudotropicalis K. 11658 | C. pseudotropicalis K. 11658 |
| Candida krusei K. 11655 | C. krusei K. 11655 |
| Candida parapsitosis A. 7330 | C. parapsitosis A. 7330 |
| Torulopsis glabrata B. 16205 | T. glabrata B. 16205 |
| Cryptococcus neoformans B. 42419 | Cry. neoformans B. 42419 |
| Cryptococcus neoformans IFM. 40092 | Cry. neoformans IFM. 40092 |
| Cryptococcus neoformans A. 34144 | Cry. neoformans A. 34144 |
| Aspergillus furnigatus B. 19119 | A. furnigatus B. 19119 |
| Aspergillus niger A. 16404 | A. niger A. 6404 |
| Trichophyton mentagrophytes A. 9129 | T. mentagrophytes A. 9129 |
| Trichophyton mentagrophytes B. 32663 | T. mentagrophytes B. 32663 |

TABLE IX

| Strain | FCZ | ICZ | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|---|---|
| C. albicans B. 02630 | >100 | >100 | 25.0 | 12.5 | 25.0 | 12.5 | 12.5 | 12.5 | 12.5 | 25.0 | 25.0 | 25.0 |
| C. albicans A. 10231 | >100 | >100 | 25.0 | 6.25 | 12.5 | 12.5 | 12.5 | 6.25 | 12.5 | 12.5 | 12.5 | 25.0 |
| C. albicans C1-2 | >100 | >100 | 25.0 | 6.25 | 25.0 | 6.25 | 12.5 | 12.5 | 12.5 | 25.0 | 25.0 | 12.5 |
| C. albicans IFO. 1385 | 12.5 | 1.56 | 3.13 | 0.78 | 0.78 | 1.56 | 0.78 | 0.78 | 1.56 | 1.56 | 1.56 | 1.56 |
| C. tropicalis A. 13803 | >100 | >100 | 50.0 | 25.0 | 25.0 | 12.5 | 12.5 | 12.5 | 25.0 | 25.0 | 25.0 | 50.0 |
| C. pseudotropicalis K. 11658 | 12.5 | 0.39 | 6.25 | 12.5 | 6.25 | 6.25 | 12.5 | 12.5 | 12.5 | 12.5 | 6.25 | 6.25 |
| C. krusei K. 11655 | 25.0 | 0.39 | 6.25 | 12.5 | 6.25 | 6.25 | 12.5 | 12.5 | 12.5 | 6.25 | 6.25 | 25.0 |
| C. parapsitosis A. 7330 | 12.5 | 0.78 | 6.25 | 12.5 | 6.25 | 12.5 | 12.5 | 12.5 | 12.5 | 12.5 | 12.5 | 12.5 |
| T. glabrata B. 16205 | 100 | 50.0 | 25.0 | 6.25 | 3.13 | 6.25 | 6.25 | 6.25 | 6.25 | 6.25 | 6.25 | 12.5 |
| Cry. neoformans B. 42419 | 25.0 | 0.39 | 0.39 | 3.13 | 3.13 | 3.13 | 3.13 | 3.13 | 1.56 | 1.56 | 1.56 | 1.56 |
| Cry. neoformans IFM. 40092 | 3.13 | ≦0.10 | 0.20 | 1.56 | 1.56 | 1.56 | 1.56 | 1.56 | 0.78 | 0.78 | 0.78 | ≦0.10 |
| Cry. neoformans A. 34144 | 12.5 | 0.39 | 0.39 | 3.13 | 0.39 | 3.13 | 3.13 | 3.13 | 1.56 | 3.13 | 3.13 | 1.56 |
| A furnigatus B. 19119 | >100 | ≦0.10 | 1.56 | 3.13 | 3.13 | 6.25 | 6.25 | 6.25 | 6.25 | 6.25 | 6.25 | 12.5 |
| A. niger A. 16404 | >100 | 1.56 | 1.56 | 3.13 | 3.13 | 6.25 | 6.25 | 6.25 | 12.5 | 6.25 | 6.25 | 50.0 |
| T. mentagrophytes A. 9129 | 50.0 | ≦0.10 | ≦0.10 | 1.56 | 1.56 | 3.13 | 3.13 | 3.13 | 6.25 | 3.13 | 3.13 | 6.25 |
| T. mentagrophytes B. 32663 | 12.5 | ≦0.10 | 0.20 | 1.56 | 1.56 | 1.56 | 3.13 | 3.13 | 1.56 | 1.56 | 1.56 | 1.56 |

| Strain | FCZ | ICZ | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|---|---|
| C. albicans B. 02630 | >100 | >100 | 25.0 | 25.0 | 6.25 | 12.5 | 6.25 | 12.5 | 12.5 | 12.5 | 6.25 | 6.25 |
| C. albicans A. 10231 | >100 | >100 | 25.0 | 12.5 | 6.25 | 6.25 | 6.25 | 12.5 | 12.5 | 6.25 | 6.25 | 6.25 |
| C. albicans C1-2 | >100 | >100 | 25.0 | 25.0 | 3.13 | 12.5 | 3.13 | 6.25 | 12.5 | 6.25 | 6.25 | 6.25 |
| C. albicans IFO. 1385 | 12.5 | 1.56 | 1.56 | 1.56 | 0.39 | 0.39 | ≦0.10 | 0.78 | 0.78 | 1.56 | 0.78 | 0.78 |
| C. tropicalis A. 13803 | >100 | >100 | 50.0 | 50.0 | 50.0 | 12.5 | 25.0 | 25.0 | 12.5 | 25.0 | 25.0 | 25.0 |
| C. pseudotropicalis K. 11658 | 12.5 | 0.39 | 3.13 | 3.13 | 1.56 | 3.13 | 3.13 | 3.13 | 6.25 | 12.5 | 25.0 | 100 |
| C. krusei K. 11655 | 25.0 | 0.39 | 12.5 | 6.25 | 25.0 | 6.25 | 6.25 | 6.25 | 12.5 | 25.0 | 50.0 | 100 |
| C. parapsitosis A. 7330 | 12.5 | 0.78 | 6.25 | 6.25 | 50.0 | 12.5 | 6.26 | 6.25 | 50.0 | >100 | >100 | >100 |
| T. glabrata B. 16205 | 100 | 50.0 | 12.5 | 6.25 | 6.25 | 6.25 | 3.13 | 6.25 | 6.25 | 6.25 | 3.13 | 12.5 |
| Cry. neoformans B. 42419 | 25.0 | 0.39 | 1.56 | 0.78 | 0.39 | 0.78 | 0.20 | 1.56 | 1.56 | 1.56 | 0.78 | 1.56 |
| Cry. neoformans IFM. 40092 | 3.13 | ≦0.10 | 0.39 | 0.39 | ≦0.10 | 0.39 | ≦0.10 | 0.39 | 0.20 | 0.78 | 0.20 | 0.39 |
| Cry. neoformans A. 34144 | 12.5 | 0.39 | 1.56 | 1.56 | 0.39 | 0.78 | 0.20 | 1.56 | 1.56 | 1.56 | 1.56 | 1.56 |
| A furnigatus B. 19119 | >100 | ≦0.10 | 12.5 | 1.56 | 1.56 | 6.25 | 0.78 | 3.13 | 6.25 | 6.25 | 1.56 | 50.0 |
| A. niger A. 16404 | >100 | 1.56 | 50.0 | 3.13 | 3.13 | 6.25 | 1.56 | 3.13 | 12.5 | 6.25 | 3.13 | 100 |
| T. mentagrophytes A. 9129 | 50.0 | ≦0.10 | 12.5 | 0.78 | 0.78 | 1.56 | 0.39 | 1.56 | 12.5 | 3.13 | 1.56 | 12.5 |
| T. mentagrophytes B. 32663 | 12.5 | ≦0.10 | 1.56 | 0.78 | ≦0.10 | 0.78 | ≦0.10 | 1.56 | 3.13 | 1.56 | 0.78 | 6.25 |

TABLE IX-continued

| Strain | FCZ | ICZ | Ex. 21 | Ex. 22 | Ex. 23 | Ex. 24 | Ex. 25 | Ex. 26 | Ex. 27 | Ex. 28 | Ex. 29 | Ex. 30 |
|---|---|---|---|---|---|---|---|---|---|---|---|---|
| C. albicans B. 02630 | >100 | >100 | 6.25 | 6.25 | 6.25 | 6.25 | 12.5 | 6.25 | 25.0 | 25.0 | >100 | 25.0 |
| C. albicans A. 10231 | >100 | >100 | 6.25 | 6.25 | 6.25 | 6.25 | 6.25 | 6.25 | 25.0 | 25.0 | >100 | 25.0 |
| C. albicans C1-2 | >100 | >100 | 6.25 | 12.5 | 6.25 | 6.25 | 12.5 | 6.25 | 25.0 | 25.0 | >100 | 25.0 |
| C. albicans IFO. 1385 | 12.5 | 1.56 | 0.78 | 0.78 | 0.78 | 0.78 | 1.56 | 0.39 | 1.56 | 1.56 | 1.56 | 1.56 |
| C. tropicalis A. 13803 | >100 | >100 | 25.0 | 25.0 | 25.0 | 25.0 | 50.0 | 12.5 | >100 | 100 | >100 | >100 |
| C. pseudotropicalis K. 11658 | 12.5 | 0.39 | 100 | 100 | 100 | 100 | 100 | 12.5 | >100 | 100 | >100 | >100 |
| C. krusei K. 11655 | 25.0 | 0.39 | >100 | 100 | 100 | >100 | 100 | 25.0 | >100 | >100 | >100 | >100 |
| C. parapsitosis A. 7330 | 12.5 | 0.78 | >100 | >100 | >100 | >100 | >100 | 12.5 | >100 | 100 | >100 | >100 |
| T. glabrata B. 16205 | 100 | 50.0 | 12.5 | 12.5 | 12.5 | 12.5 | 12.5 | 6.25 | 25.0 | 25.0 | 12.5 | 12.5 |
| Cry. neoformans B. 42419 | 25.0 | 0.39 | 1.56 | 1.56 | 1.56 | 1.56 | 1.56 | 1.56 | 1.56 | 1.56 | 1.56 | 0.78 |
| Cry. neoformans IFM. 40092 | 3.13 | ≦0.10 | 0.39 | 0.78 | 0.39 | 0.39 | 0.78 | 0.39 | 0.78 | 0.78 | 0.20 | 0.20 |
| Cry. neoformans A. 34144 | 12.5 | 0.39 | 0.78 | 1.56 | 1.56 | 0.78 | 1.56 | 1.56 | 1.56 | 1.56 | 1.56 | 0.78 |
| A furnigatus B. 19119 | >100 | ≦0.10 | 50.0 | 50.0 | 50.0 | 50.0 | 100 | 3.13 | 100 | 100 | 6.25 | 12.5 |
| A. niger A. 16404 | >100 | 1.56 | 100 | 100 | 100 | 100 | 100 | 6.25 | 100 | 100 | 100 | 25.0 |
| T. mentagrophytes A. 9129 | 50.0 | ≦0.10 | 12.5 | 25.0 | 12.5 | 12.5 | 25.0 | 1.56 | 25.0 | 25.0 | 6.25 | 6.25 |
| T. mentagrophytes B. 32663 | 12.5 | ≦0.10 | 6.25 | 12.5 | 6.25 | 6.25 | 12.5 | 0.78 | 6.25 | 6.25 | 3.13 | 1.56 |

| Strain | FCZ | ICZ | Ex. 31 | Ex. 32 | Ex. 33 | Ex. 34 | Ex. 35 | Ex. 36 | Ex. 37 | Ex. 38 | Ex. 39 | Ex. 40 |
|---|---|---|---|---|---|---|---|---|---|---|---|---|
| C. albicans B. 02630 | >100 | >100 | 12.5 | 6.25 | 12.5 | 6.25 | 25.0 | 50.0 | 25.0 | 12.5 | 25.0 | 12.5 |
| C. albicans A. 10231 | >100 | >100 | 12.5 | 6.25 | 6.25 | 6.25 | 25.0 | 50.0 | 25.0 | 12.5 | 12.5 | 12.5 |
| C. albicans C1-2 | >100 | >100 | 12.5 | 6.25 | 12.5 | 6.25 | 25.0 | 50.0 | 25.0 | 12.5 | 12.5 | 12.5 |
| C. albicans IFO. 1385 | 12.5 | 1.56 | 0.78 | 0.78 | 1.56 | 0.39 | 1.56 | 0.78 | 3.13 | 0.39 | 0.39 | 0.78 |
| C. tropicalis A. 13803 | >100 | >100 | 12.5 | 25.0 | 50.0 | 12.5 | 100 | 100 | >100 | 25.0 | 25.0 | 25.0 |
| C. pseudotropicalis K. 11658 | 12.5 | 0.39 | 12.5 | 100 | 100 | 12.5 | >100 | 25.0 | >100 | 12.5 | 12.5 | 25.0 |
| C. krusei K. 11655 | 25.0 | 0.39 | 25.0 | 100 | 100 | 25.0 | >100 | 50.0 | >100 | 25.0 | 25.0 | 25.0 |
| C. parapsitosis A. 7330 | 12.5 | 0.78 | 25.0 | >100 | >100 | 12.5 | >100 | 25.0 | >100 | 12.5 | 12.5 | 25.0 |
| T. glabrata B. 16205 | 100 | 50.0 | 6.25 | 12.5 | 25.0 | 6.25 | 25.0 | 25.0 | 6.25 | 6.25 | 6.25 | 6.25 |
| Cry. neoformans B. 42419 | 25.0 | 0.39 | 1.56 | 1.56 | 1.56 | 1.56 | 1.56 | 3.13 | 6.25 | 1.56 | 1.56 | 1.56 |
| Cry. neoformans IFM. 40092 | 3.13 | ≦0.10 | 0.78 | 0.39 | 0.78 | 0.39 | 0.78 | 0.78 | 0.78 | 0.20 | 0.20 | 0.20 |
| Cry. neoformans A. 34144 | 12.5 | 0.39 | 1.56 | 0.78 | 1.56 | 1.56 | 1.56 | 6.25 | 3.13 | 1.56 | 1.56 | 1.56 |
| A furnigatus B. 19119 | >100 | ≦0.10 | 6.25 | 50.0 | 100 | 3.13 | 100 | 1.56 | >100 | 12.5 | 12.5 | 12.5 |
| A. niger A. 16404 | >100 | 1.56 | 6.25 | 100 | 100 | 6.25 | 100 | 12.5 | >100 | 50.0 | 50.0 | 25.0 |
| T. mentagrophytes A. 9129 | 50.0 | ≦0.10 | 3.13 | 12.5 | 25.0 | 1.56 | 25.0 | 1.56 | 50.0 | 6.25 | 6.25 | 6.25 |
| T. mentagrophytes B. 32663 | 12.5 | ≦0.10 | 1.56 | 6.25 | 12.5 | 0.78 | 6.25 | 0.39 | 25.0 | 1.56 | 1.56 | 1.56 |

| Strain | FCZ | ICZ | Ex. 41 | Ex. 42 | Ex. 43 | Ex. 44 | Ex. 45 | Ex. 46 | Ex. 47 | Ex. 48 | Ex. 49 | Ex. 50 |
|---|---|---|---|---|---|---|---|---|---|---|---|---|
| C. albicans B. 02630 | >100 | >100 | 12.5 | 12.5 | 25.0 | 25.0 | 25.0 | 50.0 | 12.5 | 25.0 | 25.0 | 12.5 |
| C. albicans A. 10231 | >100 | >100 | 12.5 | 12.5 | 25.0 | 25.0 | 25.0 | 25.0 | 12.5 | 25.0 | 25.0 | 12.5 |
| C. albicans C1-2 | >100 | >100 | 12.5 | 12.5 | 25.0 | 25.0 | 25.0 | 25.0 | 12.5 | 25.0 | 25.0 | 12.5 |
| C. albicans IFO. 1385 | 12.5 | 1.56 | 0.78 | 0.78 | 0.78 | 0.39 | 0.39 | ≦0.10 | 0.20 | 0.20 | 0.20 | 0.39 |
| C. tropicalis A. 13803 | >100 | >100 | 25.0 | 25.0 | 50.0 | 50.0 | 50.0 | 50.0 | 25.0 | 50.0 | 50.0 | 25.0 |
| C. pseudotropicalis K. 11658 | 12.5 | 0.39 | 25.0 | 25.0 | 6.25 | 6.25 | 6.25 | 12.5 | 6.25 | 12.5 | 12.5 | 12.5 |
| C. krusei K. 11655 | 25.0 | 0.39 | 50.0 | 25.0 | 12.5 | 12.5 | 12.5 | 25.0 | 12.5 | 25.0 | 25.0 | 25.0 |
| C. parapsitosis A. 7330 | 12.5 | 0.78 | 100 | 25.0 | 12.5 | 12.5 | 12.5 | 25.0 | 6.25 | 25.0 | 25.0 | 12.5 |
| T. glabrata B. 16205 | 100 | 50.0 | 6.25 | 6.25 | 6.25 | 6.25 | 6.25 | 12.5 | 6.25 | 12.5 | 12.5 | 6.25 |
| Cry. neoformans B. 42419 | 25.0 | 0.39 | 3.13 | 0.78 | 1.56 | 1.56 | 1.56 | 0.78 | 0.78 | 0.78 | 0.78 | 1.56 |
| Cry. neoformans IFM. 40092 | 3.13 | ≦0.10 | 0.78 | ≦0.10 | 0.39 | 0.39 | 0.39 | ≦0.10 | ≦0.10 | ≦0.10 | ≦0.10 | 0.20 |
| Cry. neoformans A. 34144 | 12.5 | 0.39 | 3.13 | 0.78 | 1.56 | 1.56 | 1.56 | 0.78 | 0.78 | 0.78 | 0.78 | 1.56 |
| A furnigatus B. 19119 | >100 | ≦0.10 | 6.25 | 12.5 | 12.5 | 12.5 | 12.5 | 1.56 | 1.56 | 1.56 | 1.56 | 6.25 |
| A. niger A. 16404 | >100 | 1.56 | 25.0 | 100 | >100 | >100 | 100 | 12.5 | 6.25 | 6.25 | 6.25 | 25.0 |
| T. mentagrophytes A. 9129 | 50.0 | ≦0.10 | 6.25 | 6.25 | 6.25 | 6.25 | 6.25 | 0.39 | 0.39 | 0.39 | 0.39 | 3.13 |
| T. mentagrophytes B. 32663 | 12.5 | ≦0.10 | 3.13 | 1.56 | 1.56 | 1.56 | 1.56 | 0.20 | ≦0.10 | ≦0.10 | ≦0.10 | 0.78 |

| Strain | FCZ | ICZ | Ex. 51 | Ex. 52 | Ex. 53 | Ex. 54 | Ex. 55 | Ex. 56 | Ex. 57 | Ex. 58 | Ex. 59 | Ex. 60 |
|---|---|---|---|---|---|---|---|---|---|---|---|---|
| C. albicans B. 02630 | >100 | >100 | 12.5 | 12.5 | 25.0 | 25.0 | 12.5 | 12.5 | 12.5 | 25.0 | 25.0 | 12.5 |
| C. albicans A. 10231 | >100 | >100 | 12.5 | 12.5 | 12.5 | 12.5 | 12.5 | 12.5 | 12.5 | 25.0 | 12.5 | 12.5 |
| C. albicans C1-2 | >100 | >100 | 12.5 | 12.5 | 25.0 | 25.0 | 12.5 | 12.5 | 12.5 | 25.0 | 25.0 | 12.5 |
| C. albicans IFO. 1385 | 12.5 | 1.56 | 0.39 | 0.39 | 0.78 | 0.78 | 0.78 | 0.78 | 0.78 | 0.78 | 0.78 | 0.78 |
| C. tropicalis A. 13803 | >100 | >100 | 25.0 | 50.0 | 100 | 100 | 25.0 | 100 | 100 | >100 | >100 | 100 |
| C. pseudotropicalis K. 11658 | 12.5 | 0.39 | 25.0 | 50.0 | >100 | 100 | 50.0 | >100 | >100 | 50.0 | 25.0 | 100 |
| C. krusei K. 11655 | 25.0 | 0.39 | 50.0 | 100 | >100 | >100 | >100 | >100 | >100 | 100 | 50.0 | >100 |
| C. parapsitosis A. 7330 | 12.5 | 0.78 | >100 | >100 | >100 | >100 | >100 | >100 | >100 | >100 | >100 | >100 |
| T. glabrata B. 16205 | 100 | 50.0 | 6.25 | 3.13 | 6.25 | 6.25 | 6.25 | 6.25 | 6.25 | 6.25 | 3.13 | 6.25 |
| Cry. neoformans B. 42419 | 25.0 | 0.39 | 1.56 | 0.78 | 0.78 | 0.78 | 0.78 | 0.78 | 0.78 | 1.56 | 3.13 | 1.56 |
| Cry. neoformans IFM. 40092 | 3.13 | ≦0.10 | 0.20 | ≦0.10 | ≦10.10 | ≦0.10 | ≦0.10 | 0.20 | 0.20 | 0.39 | 0.78 | 0.20 |
| Cry. neoformans A. 34144 | 12.5 | 0.39 | 1.56 | 0.78 | 1.56 | 1.56 | 0.78 | 1.56 | 1.56 | 1.56 | 3.13 | 1.56 |
| A furnigatus B. 19119 | >100 | ≦0.10 | 3.13 | 1.56 | 3.13 | 3.13 | 100 | 50.0 | 50.0 | 25.0 | 50.0 | 12.5 |
| A. niger A. 16404 | >100 | 1.56 | 12.5 | 6.25 | 25.0 | 25.0 | >100 | >100 | >100 | >100 | >100 | 100 |
| T. mentagrophytes A. 9129 | 50.0 | ≦0.10 | 1.56 | 1.56 | 3.13 | 3.13 | 6.25 | 6.25 | 6.25 | 12.5 | 25.0 | 6.25 |
| T. mentagrophytes B. 32663 | 12.5 | ≦0.10 | 0.78 | 0.78 | 1.56 | 1.56 | 3.13 | 3.13 | 3.13 | 6.25 | 12.5 | 3.13 |

| Strain | FCZ | ICZ | Ex. 61 | Ex. 62 | Ex. 63 | Ex. 64 | Ex. 65 | Ex. 66 | Ex. 67 | Ex. 68 | Ex. 69 | Ex. 70 |
|---|---|---|---|---|---|---|---|---|---|---|---|---|
| C. albicans B. 02630 | >100 | >100 | 12.5 | 12.5 | 50.0 | 12.5 | 12.5 | 12.5 | 12.5 | 12.5 | 25.0 | 25.0 |

TABLE IX-continued

| Strain | FCZ | ICZ | | | | | | | | | | |
|---|---|---|---|---|---|---|---|---|---|---|---|---|
| C. albicans A. 10231 | >100 | >100 | 12.5 | 12.5 | 25.0 | 12.5 | 12.5 | 12.5 | 12.5 | 6.25 | 25.0 | 25.0 |
| C. albicans C1-2 | >100 | >100 | 12.5 | 12.5 | 50.0 | 12.5 | 12.5 | 12.5 | 12.5 | 12.5 | 25.0 | 25.0 |
| C. albicans IFO. 1385 | 12.5 | 1.56 | 0.78 | 0.78 | 3.13 | 0.78 | 0.78 | 0.39 | 0.78 | 0.78 | 3.13 | 6.25 |
| C. tropicalis A. 13803 | >100 | >100 | 100 | 100 | >100 | 100 | 50.0 | 100 | 100 | 50.0 | >100 | 100 |
| C. pseudotropicalis K. 11658 | 12.5 | 0.39 | 100 | 50.0 | >100 | 25.0 | 25.0 | 50.0 | 25.0 | 25.0 | 6.25 | 50.0 |
| C. krusei K. 11655 | 25.0 | 0.39 | >100 | 100 | >100 | 50.0 | 100 | 100 | 50.0 | 50.0 | 12.5 | 100 |
| C. parapsitosis A. 7330 | 12.5 | 0.78 | >100 | >100 | 100 | 100 | >100 | >100 | 100 | >100 | >100 | >100 |
| T. glabrata B. 16205 | 100 | 50.0 | 6.25 | 3.13 | 25.0 | 6.25 | 6.25 | 6.25 | 6.25 | 3.13 | 25 | 25.0 |
| Cry. neoformans B. 42419 | 25.0 | 0.39 | 1.56 | 0.78 | 1.56 | 1.56 | 1.56 | 0.39 | 1.56 | 0.78 | 1.56 | 3.13 |
| Cry. neoformans IFM. 40092 | 3.13 | ≦0.10 | 0.20 | 0.20 | 0.39 | 0.20 | ≦0.10 | ≦0.10 | 0.20 | ≦0.10 | 0.39 | 0.78 |
| Cry. neoformans A. 34144 | 12.5 | 0.39 | 1.56 | 0.78 | 1.56 | 1.56 | 1.56 | 0.78 | 1.56 | 1.56 | 3.13 | 3.13 |
| A furnigatus B. 19119 | >100 | ≦0.10 | 12.5 | 25.0 | >100 | 3.13 | 3.13 | 6.25 | 3.13 | 1.56 | 6.25 | 50.0 |
| A. niger A. 16404 | >100 | 1.56 | 100 | >100 | >100 | 100 | 12.5 | >100 | 100 | 12.5 | 6.25 | 100 |
| T. mentagrophytes A. 9129 | 50.0 | ≦0.10 | 6.25 | 12.5 | 25.0 | 6.25 | 3.13 | 6.25 | 6.25 | 1.56 | 0.78 | 3.13 |
| T. mentagrophytes B. 32663 | 12.5 | ≦0.10 | 3.13 | 3.13 | 6.25 | 1.56 | 1.53 | 3.13 | 1.56 | 1.56 | 0.39 | 3.13 |

| Strain | FCZ | ICZ | Ex. 71 | Ex. 72 | Ex. 73 | Ex. 74 | Ex. 75 | Ex. 76 | Ex. 77 | Ex. 78 | Ex. 79 | Ex. 80 |
|---|---|---|---|---|---|---|---|---|---|---|---|---|
| C. albicans B. 02630 | >100 | >100 | 50.0 | 25.0 | 50.0 | 100 | 100 | 6.25 | 100 | 100 | >100 | >100 |
| C. albicans A. 10231 | >100 | >100 | 50.0 | 250 | 50.0 | 100 | 100 | 6.25 | 100 | 100 | >100 | >100 |
| C. albicans C1-2 | >100 | >100 | 50.0 | 25.0 | 50.0 | 100 | 100 | 6.25 | 100 | 100 | >100 | >100 |
| C. albicans IFO. 1385 | 12.5 | 1.56 | 6.25 | 1.56 | 12.5 | 12.5 | 25.0 | 6.25 | 25.0 | 12.5 | >100 | 12.5 |
| C. tropicalis A. 13803 | >100 | >100 | 100 | 25.0 | >100 | >100 | 100 | 25.0 | 100 | >100 | >100 | >100 |
| C. pseudotropicalis K. 11658 | 12.5 | 0.39 | 25.0 | 12.5 | 50.0 | 25.0 | 25.0 | 100 | 6.25 | >100 | >100 | >100 |
| C. krusei K. 11655 | 25.0 | 0.39 | 100 | 25.0 | 100 | 100 | 100 | >100 | 12.5 | >100 | >100 | >100 |
| C. parapsitosis A. 7330 | 12.5 | 0.78 | 100 | 100 | >100 | >100 | >100 | >100 | 12.5 | >100 | >100 | >100 |
| T. glabrata B. 16205 | 100 | 50.0 | 25.0 | 25.0 | 50.0 | 50.0 | 50.0 | 25.0 | 50.0 | 100 | >100 | >100 |
| Cry. neoformans B. 42419 | 25.0 | 0.39 | 1.56 | 3.13 | 6.25 | 3.13 | 1.56 | 3.13 | 1.56 | 6.25 | >100 | 1.56 |
| Cry. neoformans IFM. 40092 | 3.13 | ≦0.10 | 0.20 | 1.56 | 1.56 | 0.78 | 0.39 | 0.78 | 0.78 | 0.78 | 1.56 | 0.78 |
| Cry. neoformans A. 34144 | 12.5 | 0.39 | 1.56 | 3.13 | 12.5 | 6.25 | 1.56 | 3.13 | 3.13 | 12.5 | >100 | 1.56 |
| A furnigatus B. 19119 | >100 | ≦0.10 | 100 | >100 | >100 | >100 | 100 | 25.0 | 100 | >100 | >100 | >100 |
| A. niger A. 16404 | >100 | 1.56 | 100 | >100 | >100 | >100 | >100 | 12.5 | >100 | >100 | >100 | >100 |
| T. mentagrophytes A. 9129 | 50.0 | ≦0.10 | 6.25 | 12.5 | 25.0 | 12.5 | 3.13 | 3.13 | 6.25 | 50.0 | >100 | 100 |
| T. mentagrophytes B. 32663 | 12.5 | ≦0.10 | 6.25 | 12.5 | 25.0 | 12.5 | 3.13 | 3.13 | 6.25 | 50.0 | >100 | 100 |

| Strain | FCZ | ICZ | Ex. 81 | Ex. 82 | Ex. 83 | Ex. 84 | Ex. 85 | Ex. 86 | Ex. 87 | Ex. 88 | Ex. 89 | Ex. 90 |
|---|---|---|---|---|---|---|---|---|---|---|---|---|
| C. albicans B. 02630 | >100 | >100 | >100 | >100 | >100 | >100 | 100 | 100 | >100 | 100 | 100 | 100 |
| C. albicans A. 10231 | >100 | >100 | >100 | >100 | >100 | 100 | 100 | 100 | 100 | 100 | 100 | 100 |
| C. albicans C1-2 | >100 | >100 | >100 | >100 | >100 | 100 | 100 | 100 | 100 | 100 | 100 | 100 |
| C. albicans IFO. 1385 | 12.5 | 1.56 | 12.5 | 12.5 | >100 | 6.25 | 25.0 | 12.5 | 6.25 | 6.25 | 25.0 | 12.5 |
| C. tropicalis A. 13803 | >100 | >100 | >100 | >100 | >100 | >100 | >100 | >100 | >100 | >100 | 100 | >100 |
| C. pseudotropicalis K. 11658 | 12.5 | 0.39 | 50.0 | >100 | >100 | >100 | >100 | >100 | >100 | >100 | 6.25 | >100 |
| C. krusei K. 11655 | 25.0 | 0.39 | >100 | >100 | >100 | >100 | >100 | >100 | >100 | >100 | 12.5 | >100 |
| C. parapsitosis A. 7330 | 12.5 | 0.78 | >100 | >100 | >100 | >100 | >100 | >100 | >100 | >100 | 12.5 | >100 |
| T. glabrata B. 16205 | 100 | 50.0 | >100 | >100 | >100 | >100 | >100 | >100 | >100 | >100 | 50.0 | 100 |
| Cry. neoformans B. 42419 | 25.0 | 0.39 | 1.56 | 3.13 | >100 | 1.56 | 1.56 | 1.56 | 1.56 | 1.56 | 1.56 | 6.25 |
| Cry. neoformans IFM. 40092 | 3.13 | ≦0.10 | 0.39 | 0.39 | 1.56 | 0.78 | 0.39 | 0.78 | 0.78 | 0.78 | 0.78 | 0.78 |
| Cry. neoformans A. 34144 | 12.5 | 0.39 | 0.78 | 3.13 | >100 | 1.56 | 1.56 | 1.56 | 1.56 | 1.56 | 3.13 | 12.5 |
| A furnigatus B. 19119 | >100 | ≦0.10 | >100 | >100 | >100 | >100 | >100 | >100 | >100 | >100 | 100 | >100 |
| A. niger A. 16404 | >100 | 1.56 | >100 | >100 | >100 | >100 | >100 | >100 | >100 | >100 | >100 | >100 |
| T. mentagrophytes A. 9129 | 50.0 | ≦0.10 | 100 | >100 | >100 | >100 | >100 | >100 | >100 | 100 | 6.25 | 50.0 |
| T. mentagrophytes B. 32663 | 12.5 | ≦0.10 | 100 | >100 | >100 | >100 | >100 | >100 | >100 | 100 | 6.25 | 50.0 |

| Strain | FCZ | ICZ | Ex. 91 | Ex. 92 | Ex. 93 | Ex. 94 | Ex. 95 | Ex. 96 | Ex. 97 | Ex. 98 | Ex. 99 | Ex. 100 |
|---|---|---|---|---|---|---|---|---|---|---|---|---|
| C. albicans B. 02630 | >100 | >100 | 100 | 25.0 | 100 | 25.0 | >100 | 100 | >100 | 50.0 | 100 | 50.0 |
| C. albicans A. 10231 | >100 | >100 | 100 | 25.0 | 100 | 25.0 | >100 | 100 | >100 | 50.0 | 100 | 50.0 |
| C. albicans C1-2 | >100 | >100 | 100 | 50.0 | >100 | 50.0 | >100 | 100 | >100 | 100 | >100 | 100 |
| C. albicans IFO. 1385 | 12.5 | 1.56 | 6.25 | 3.13 | 6.25 | 3.13 | 6.25 | 3.13 | 3.13 | 3.13 | 3.13 | 6.25 |
| C. tropicalis A. 13803 | >100 | >100 | >100 | >100 | >100 | >100 | >100 | >100 | >100 | >100 | >100 | >100 |
| C. pseudotropicalis K. 11658 | 12.5 | 0.39 | >100 | >100 | >100 | >100 | >100 | >100 | >100 | >100 | >100 | >100 |
| C. krusei K. 11655 | 25.0 | 0.39 | >100 | >100 | >100 | >100 | >100 | >100 | >100 | >100 | >100 | >100 |
| C. parapsitosis A. 7330 | 12.5 | 0.78 | >100 | >100 | >100 | >100 | >100 | >100 | >100 | >100 | >100 | >100 |
| T. glabrata B. 16205 | 100 | 50.0 | >100 | 50.0 | >100 | 50.0 | >100 | 100 | >100 | 50 | 100 | >100 |
| Cry. neoformans B. 42419 | 25.0 | 0.39 | 1.56 | 3.13 | >100 | 3.13 | 6.25 | 3.13 | 3.13 | 6.25 | 3.13 | 12.5 |
| Cry. neoformans IFM. 40092 | 3.13 | ≦0.10 | 0.78 | 0.78 | 1.56 | 0.78 | 1.5& | 0.39 | 0.78 | 0.78 | 0.78 | 1.56 |
| Cry. neoformans A. 34144 | 12.5 | 0.39 | 1.56 | 3.13 | 12.5 | 3.13 | 3.13 | 3.13 | 3.13 | 3.13 | 3.13 | 6.25 |
| A furnigatus B. 19119 | >100 | ≦0.10 | 100 | >100 | >100 | >100 | >100 | 100 | >100 | >100 | >100 | >100 |
| A. niger A. 16404 | >100 | 1.56 | >100 | >100 | >100 | >100 | >100 | >100 | >100 | >100 | >100 | >100 |
| T. mentagrophytes A. 9129 | 50.0 | ≦0.10 | 100 | 25.0 | 25.0 | 25.0 | 50.0 | 12.5 | 25.0 | 25.0 | 50.0 | 100 |
| T. mentagrophytes B. 32663 | 12.5 | ≦0.10 | >100 | 12.5 | 25.0 | 12.5 | 50.0 | 6.25 | 12.5 | 6.25 | 25.0 | 100 |

| Strain | FCZ | ICZ | Ex. 101 | Ex. 102 | Ex. 103 | Ex. 104 | Ex. 105 | Ex. 106 | Ex. 107 | Ex. 108 | Ex. 109 | Ex. 110 |
|---|---|---|---|---|---|---|---|---|---|---|---|---|
| C. albicans B. 02630 | >100 | >100 | 25.0 | 100 | 50.0 | >100 | 50.0 | 50.0 | 50.0 | >100 | 100 | 100 |
| C. albicans A. 10231 | >100 | >100 | 25.0 | 100 | 50.0 | 100 | 50.0 | 100 | 100 | >100 | 100 | 100 |
| C. albicans C1-2 | >100 | >100 | 50.0 | 100 | 50.0 | >100 | 100 | 50.0 | 50.0 | 100 | 50.0 | 50.0 |
| C. albicans IFO. 1385 | 12.5 | 1.56 | 3.13 | 6.25 | 3.13 | 3.13 | 6.25 | 1.56 | 3.13 | 6.25 | 3.13 | 3.13 |

TABLE IX-continued

| Strain | FCZ | ICZ | | | | | | | | | | |
|---|---|---|---|---|---|---|---|---|---|---|---|---|
| C. tropicalis A. 13803 | >100 | >100 | >100 | >100 | >100 | >100 | >100 | >100 | >100 | >100 | >100 | >100 |
| C. pseudotropicalis K. 11658 | 12.5 | 0.39 | >100 | >100 | >100 | >100 | >100 | 3.13 | 100 | >100 | >100 | >100 |
| C. krusei K. 11655 | 25.0 | 0.39 | >100 | >100 | >100 | >100 | >100 | 3.13 | >100 | >100 | >100 | >100 |
| C. parapsitosis A. 7330 | 12.5 | 0.78 | >100 | >100 | >100 | >100 | >100 | 3.13 | >100 | >100 | >100 | >100 |
| T. glabrata B. 16205 | 100 | 50.0 | 25.0 | 100 | 50.0 | 100 | >100 | 50.0 | 100 | >100 | 100 | 100 |
| Cry. neoformans B. 42419 | 25.0 | 0.39 | 3.13 | >100 | 3.13 | 3.13 | 12.5 | 1.56 | 3.13 | 3.13 | 3.13 | 3.13 |
| Cry. neoformans IFM. 40092 | 3.13 | ≦0.10 | 0.78 | 3.13 | 0.78 | 0.78 | 1.56 | 0.39 | 0.39 | 0.78 | 0.39 | 0.39 |
| Cry. neoformans A. 34144 | 12.5 | 0.39 | 3.13 | 12.5 | 3.13 | 3.13 | 6.25 | 1.56 | 1.56 | 3.13 | 1.56 | 1.56 |
| A furnigatus B. 19119 | >100 | ≦0.10 | 50.0 | 100 | 100 | >100 | >100 | >100 | >100 | >100 | >100 | >100 |
| A. niger A. 16404 | >100 | 1.56 | >100 | >100 | >100 | >100 | >100 | >100 | >100 | >100 | >100 | >100 |
| T. mentagrophytes A. 9129 | 50.0 | ≦0.10 | 25.0 | 25.0 | 12.5 | 50.0 | 100 | 3.13 | 12.5 | 50.0 | 6.25 | 6.25 |
| T. mentagrophytes B. 32663 | 12.5 | ≦0.10 | 12.5 | 12.5 | 6.25 | 25.0 | 100 | 1.56 | 3.13 | 12.5 | 3.13 | 3.13 |

| Strain | FCZ | ICZ | Ex. 111 | Ex. 112 | Ex. 113 | Ex. 114 | Ex. 115 | Ex. 116 | Ex. 117 | Ex. 118 | Ex. 119 | Ex. 120 |
|---|---|---|---|---|---|---|---|---|---|---|---|---|
| C. albicans B. 02630 | >100 | >100 | 100 | 25.0 | >100 | 25.0 | 25.0 | 100 | 12.5 | 25.0 | 25.0 | 25.0 |
| C. albicans A. 10231 | >100 | >100 | 100 | 25.0 | >100 | 50.0 | 25.0 | 100 | 12.5 | 25.0 | 50.0 | 25.0 |
| C. albicans C1-2 | >100 | >100 | 50.0 | 12.5 | >100 | 25.0 | 25.0 | 100 | 6.25 | 12.5 | 25.0 | 25.0 |
| C. albicans IFO. 1385 | 12.5 | 1.56 | 3.13 | 1.56 | 3.13 | 1.56 | 1.56 | 3.13 | 0.78 | 1.56 | 1.56 | 1.56 |
| C. tropicalis A. 13803 | >100 | >100 | >100 | 100 | >100 | >100 | 100 | >100 | 25.0 | 100 | >100 | 100 |
| C. pseudotropicalis K. 11658 | 12.5 | 0.39 | 100 | 25.0 | 100 | >100 | >100 | 25.0 | 6.25 | 25.0 | >100 | >100 |
| C. krusei K. 11655 | 25.0 | 0.39 | >100 | >100 | >100 | >100 | >100 | 100 | 12.5 | >100 | >100 | >100 |
| C. parapsitosis A. 7330 | 12.5 | 0.78 | 100 | >100 | >100 | >100 | >100 | 100 | 6.25 | >100 | >100 | >100 |
| T. glabrata B. 16205 | 100 | 50.0 | 100 | 50.0 | >100 | 50.0 | 50.0 | 50.0 | 12.5 | 50.0 | 50.0 | 50.0 |
| Cry. neoformans B. 42419 | 25.0 | 0.39 | 3.13 | 1.56 | 3.13 | 1.56 | 3.13 | 1.56 | 1.56 | 1.56 | 1.56 | 3.13 |
| Cry. neoformans IFM. 40092 | 3.13 | ≦0.10 | 0.39 | 0.39 | 0.39 | 0.39 | 0.39 | 0.20 | 0.20 | 0.39 | 0.39 | 0.39 |
| Cry. neoformans A. 34144 | 12.5 | 0.39 | 1.56 | 1.56 | 1.56 | 1.56 | 1.56 | 1.56 | 0.78 | 1.56 | 1.56 | 1.56 |
| A furnigatus B. 19119 | >100 | ≦0.10 | >100 | >100 | >100 | >100 | >100 | >100 | 12.5 | >100 | >100 | >100 |
| A. niger A. 16404 | >100 | 1.56 | >100 | >100 | >100 | >100 | >100 | >100 | 100 | >100 | >100 | >100 |
| T. mentagrophytes A. 9129 | 50.0 | ≦0.10 | 6.25 | 6.25 | 25.0 | 6.25 | 6.25 | 6.25 | 6.25 | 6.25 | 6.25 | 6.25 |
| T. mentagrophytes B. 32663 | 12.5 | ≦0.10 | 3.13 | 3.13 | 12.5 | 3.13 | 3.13 | 3.13 | 3.13 | 3.13 | 3.13 | 3.13 |

| Strain | FCZ | ICZ | Ex. 121 | Ex. 122 | Ex. 123 | Ex. 124 | Ex. 125 | Ex. 126 | Ex. 127 | Ex. 128 | Ex. 129 | Ex. 130 |
|---|---|---|---|---|---|---|---|---|---|---|---|---|
| C. albicans B. 02630 | >100 | >100 | 100 | 12.5 | 25.0 | 25.0 | 25.0 | >100 | >100 | >100 | >100 | >100 |
| C. albicans A. 10231 | >100 | >100 | 100 | 12.5 | 25.0 | 50.0 | 25.0 | >100 | >100 | >100 | >100 | >100 |
| C. albicans C1-2 | >100 | >100 | 100 | 6.25 | 12.5 | 25.0 | 25.0 | >100 | >100 | >100 | >100 | >100 |
| C. albicans IFO. 1385 | 12.5 | 1.56 | 3.13 | 0.78 | 1.56 | 1.56 | 1.56 | 1.56 | 3.13 | 1.56 | 3.13 | 3.13 |
| C. tropicalis A. 13803 | >100 | >100 | >100 | 25.0 | 100 | >100 | 100 | >100 | >100 | >100 | >100 | >100 |
| C. pseudotropicalis K. 11658 | 12.5 | 0.39 | 25.0 | 6.25 | 25.0 | >100 | >100 | 1.56 | 1.56 | 1.56 | 1.56 | 1.56 |
| C. krusei K. 11655 | 25.0 | 0.39 | 100 | 12.5 | >100 | >100 | >100 | 3.13 | 3.13 | 3.13 | 3.13 | 1.56 |
| C. parapsitosis A. 7330 | 12.5 | 0.78 | 100 | 6.25 | >100 | >100 | >100 | 3.13 | 3.13 | 3.13 | 3.13 | 1.56 |
| T. glabrata B. 16205 | 100 | 50.0 | 50.0 | 12.5 | 50.0 | 50.0 | 50.0 | >100 | >100 | >100 | >100 | >100 |
| Cry. neoformans B. 42419 | 25.0 | 0.39 | 1.56 | 1.56 | 1.56 | 1.56 | 3.13 | 0.78 | 0.78 | 0.78 | 0.78 | 0.78 |
| Cry. neoformans IFM. 40092 | 3.13 | ≦0.10 | 0.20 | 0.20 | 0.39 | 0.39 | 0.39 | ≦0.10 | 0.39 | ≦0.10 | 0.39 | 0.20 |
| Cry. neoformans A. 34144 | 12.5 | 0.39 | 1.56 | 0.78 | 1.56 | 1.56 | 1.56 | 0.78 | 0.78 | 0.78 | 0.78 | 0.78 |
| A furnigatus B. 19119 | >100 | ≦0.10 | >100 | 12.5 | >100 | >100 | >100 | >100 | >100 | >100 | >100 | >100 |
| A. niger A. 16404 | >100 | 1.56 | >100 | 100 | >100 | >100 | >100 | >100 | >100 | >100 | >100 | >100 |
| T. mentagrophytes A. 9129 | 50.0 | ≦0.10 | 6.25 | 6.25 | 6.25 | 6.25 | 6.25 | 12.5 | 12.5 | 12.5 | 12.5 | 25.0 |
| T. mentagrophytes B. 32663 | 12.5 | ≦0.10 | 3.13 | 3.13 | 3.13 | 3.13 | 3.13 | 6.25 | 3.13 | 6.25 | 3.13 | 12.5 |

| Strain | FCZ | ICZ | Ex. 131 | Ex. 132 | Ex. 133 | Ex. 134 | Ex. 135 | Ex. 136 | Ex. 137 | Ex. 138 | Ex. 139 | Ex. 140 |
|---|---|---|---|---|---|---|---|---|---|---|---|---|
| C. albicans B. 02630 | >100 | >100 | >100 | >100 | >100 | >100 | >100 | >100 | >100 | >100 | >100 | >100 |
| C. albicans A. 10231 | >100 | >100 | >100 | >100 | >100 | >100 | >100 | >100 | >100 | >100 | >100 | >100 |
| C. albicans C1-2 | >100 | >100 | >100 | >100 | >100 | >100 | >100 | >100 | >100 | >100 | >100 | >100 |
| C. albicans IFO. 1385 | 12.5 | 1.56 | 1.56 | 1.56 | 3.13 | 1.56 | 1.56 | >100 | >100 | 0.78 | 0.78 | 1.56 |
| C. tropicalis A. 13803 | >100 | >100 | >100 | >100 | >100 | >100 | >100 | >100 | >100 | >100 | >100 | >100 |
| C. pseudotropicalis K. 11658 | 12.5 | 0.39 | 1.56 | 1.56 | 1.56 | 1.56 | 1.56 | >100 | >100 | 1.56 | 1.56 | 1.56 |
| C. krusei K. 11655 | 25.0 | 0.39 | 1.56 | 1.56 | 1.56 | 1.56 | 1.56 | >100 | >100 | 1.56 | 1.56 | 3.13 |
| C. parapsitosis A. 7330 | 12.5 | 0.78 | 3.13 | 1.56 | 3.13 | 3.13 | 1.56 | >100 | >100 | 0.78 | 0.78 | 1.56 |
| T. glabrata B. 16205 | 100 | 50.0 | >100 | >100 | >100 | >100 | >100 | >100 | >100 | 100 | 100 | 100 |
| Cry. neoformans B. 42419 | 25.0 | 0.39 | 0.78 | 0.78 | 0.39 | 0.78 | 0.78 | >100 | >100 | 0.78 | 0.78 | 1.56 |
| Cry. neoformans IFM. 40092 | 3.13 | ≦0.10 | 0.20 | 0.20 | 0.20 | 0.20 | 0.20 | 1.56 | 3.13 | ≦0.10 | ≦0.10 | 0.39 |
| Cry. neoformans A. 34144 | 12.5 | 0.39 | 0.39 | 0.78 | 0.78 | 0.39 | 0.39 | >100 | >100 | 0.78 | 0.78 | 1.56 |
| A furnigatus B. 19119 | >100 | ≦0.10 | >100 | >100 | >100 | >100 | >100 | >100 | >100 | 12.5 | 25.0 | 50.0 |
| A. niger A. 16404 | >100 | 1.56 | >100 | >100 | >100 | >100 | >100 | >100 | >100 | 100 | 100 | >100 |
| T. mentagrophytes A. 9129 | 50.0 | ≦0.10 | 6.25 | 6.25 | 6.25 | 6.25 | 3.13 | >100 | >100 | 3.13 | 6.25 | 12.5 |
| T. mentagrophytes B. 32663 | 12.5 | ≦0.10 | 1.56 | 1.56 | 1.56 | 1.56 | 1.56 | >100 | 100 | ≦0.10 | 0.39 | 0.39 |

| Strain | FCZ | ICZ | Ex. 141 | Ex. 142 | Ex. 143 | Ex. 144 | Ex. 145 | Ex. 146 | Ex. 147 | Ex. 148 | Ex. 149 | Ex. 150 |
|---|---|---|---|---|---|---|---|---|---|---|---|---|
| C. albicans B. 02630 | >100 | >100 | >100 | >100 | >100 | >100 | >100 | >100 | >100 | >100 | >100 | >100 |
| C. albicans A. 10231 | >100 | >100 | >100 | >100 | >100 | >100 | >100 | >100 | >100 | >100 | >100 | >100 |
| C. albicans C1-2 | >100 | >100 | >100 | >100 | >100 | >100 | >100 | >100 | >100 | >100 | >100 | >100 |
| C. albicans IFO. 1385 | 12.5 | 1.56 | 0.78 | 3.13 | 0.39 | 0.39 | 0.78 | 0.78 | 0.78 | 0.39 | 0.39 | 0.39 |
| C. tropicalis A. 13803 | >100 | >100 | >100 | >100 | >100 | >100 | >100 | >100 | >100 | >100 | >100 | >100 |
| C. pseudotropicalis K. 11658 | 12.5 | 0.39 | 3.13 | 6.25 | 6.25 | 1.56 | 3.13 | 0.39 | 0.39 | 0.78 | 0.39 | 0.78 |
| C. krusei K. 11655 | 25.0 | 0.39 | 1.56 | 6.25 | 1.56 | 6.25 | 1.56 | 0.78 | 0.39 | 0.39 | 0.39 | 0.78 |

TABLE IX-continued

| | | | | | | | | | | | | |
|---|---|---|---|---|---|---|---|---|---|---|---|---|
| C. parapsitosis A. 7330 | 12.5 | 0.78 | 1.56 | 3.13 | 3.13 | 3.13 | 3.13 | 1.56 | 0.78 | 0.78 | 0.78 | 1.56 |
| T. glabrata B. 16205 | 100 | 50.0 | 100 | 100 | 100 | >100 | 100 | 100 | 50.0 | 50.0 | 50.0 | 50.0 |
| Cry. neoformans B. 42419 | 25.0 | 0.39 | 0.78 | 3.13 | 0.39 | 0.39 | 0.78 | 0.78 | 0.78 | 0.78 | 0.39 | 0.39 |
| Cry. neoformans IFM. 40092 | 3.13 | ≦0.10 | 0.78 | 0.39 | 0.78 | 0.39 | 0.78 | 0.78 | ≦0.10 | ≦0.10 | ≦0.10 | ≦0.10 |
| Cry. neoformans A. 34144 | 12.5 | 0.39 | 1.56 | 3.13 | 3.13 | 3.13 | 3.13 | 1.56 | 0.78 | 0.78 | 0.78 | 1.56 |
| A. furnigatus B. 19119 | >100 | ≦0.10 | 50.0 | 50.0 | 100 | 100 | 100 | 100 | 12.5 | 6.25 | 6.25 | 12.5 |
| A. niger A. 16404 | >100 | 1.56 | >100 | 100 | >100 | >100 | 100 | 100 | 100 | 100 | 100 | 100 |
| T. mentagrophytes A. 9129 | 50.0 | ≦0.10 | 6.25 | 12.5 | 6.25 | 12.5 | 6.25 | 12.5 | 3.13 | 3.13 | 3.13 | 3.13 |
| T. mentagrophytes B. 32663 | 12.5 | ≦0.10 | 0.78 | 1.56 | 0.78 | 1.56 | 1.56 | 1.56 | ≦0.10 | ≦0.10 | ≦0.10 | ≦0.10 |

TEST EXAMPLE 2

Toxicity of Oral Administration 30 four-week-old, specific pathogen-free ICR mice, 15 female mice each weighing about 15.8 to 22.3 g and 15 male mice each weighing about 18.7 to 25.6 g, were provided by the Animal Center of Korean Research Institute of Chemical and Technology.

When the mice became five-week-old, 15 female mice each weighing about 17.0 to 22.3 g and 15 male mice each weighing about 22.0 to 27.7 g were bred for 6 days before the experiment under an environment of 23±30° C., 50±10% relative humidity, 12L/12D photoperiod, 10–20 ventilation and 150–300 Lux illumination, with free access to food (Cheil Fodder Co.) which had been sterilized by using 2.0 Mrad radiation and water sterilized by U.V. sterilizer.

The compound of Example 26 of the present invention was dissolved in corn oil containing 30% DMSO and the solution was orally administered in doses of 10, 50, 100, 500, 1,000 and 2,000 mg of the compound/kg of the body weight(10 ml of the sample volume/kg of the body weight). The solution was administered once and the mice were observed for 7 days for signs of adverse effects or death according to the following schedule: 1, 2, 4 and 12 hours after the administration and, every 12 hours thereafter. The weight changes of the mice were recorded every day to examine the effect of the test compound. Further, on the 7th day, the mice were sacrificed and the internal organs were visually examined. The autopsy revealed that the mice did not develop any pathological abnormality, and no weight loss was observed during the 7 day test period.

All the mice were alive at day 7 at a dose of 1,000 mg/kg or below. The $LD_{50}$ of the compound 26 was determined to be higher than 2,000 mg/kg (male) and approximately 2,000 mg/kg (female). In contrast, the conventional antifungal agents exhibit higher $LD_{50}$ values, i.e., ketoconazole(mouse, oral, 702 mg/kg), itraconazole(mouse, oral, 320 mg/kg), fluconazole and amphotericin B from a natural source (mouse, intravenous, 4 mg/kg).

While the invention has been described with respect to the specific embodiments, it should be recognized that various modifications and changes may be made by those skilled in the art to the invention which also fall within the scope of the invention as defined by the appended claims.

What is claimed is:

1. An azole derivative of formula (I) or a pharmaceutically acceptable salt thereof:

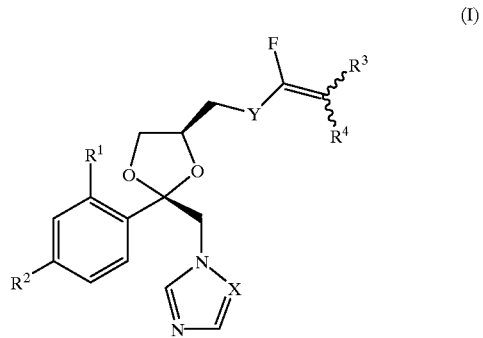

(I)

wherein:
X is CH or N;

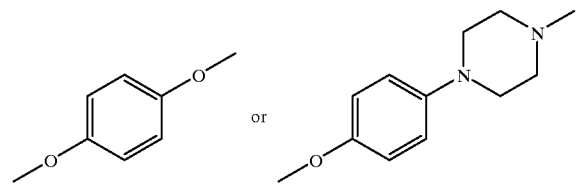

or

Y is O,
$R^1$ and $R^2$ are each independently F or Cl;
$R^3$ is a thiophenyl, naphthyl, or phenyl group, the phenyl group being optionally substituted with one or more substituents selected from the group consisting of $C_{1-4}$ alkyl, $C_{1-4}$ haloalkyl, $C_{1-4}$ alkoxy, methylenedioxy and halogen; and
$R^4$ is H or trifluoromethyl.

2. The compound of claim 1 wherein Y is O; and $R^3$ is a phenyl group optionally substituted with one or more substituents selected from the group consisting of Cl, F and Br.

3. The compound of claim 1 wherein C is CH; Y is O; $R^3$ is methylphenyl; and $R^4$ is H.

4. A process for the preparation of the compound of claim 1 which comprises reacting a compound of formula (II) with a fluorinated vinyl compound of formula (III) in the presence of a base:

(II)
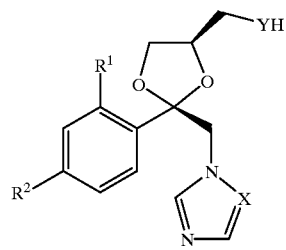
(III)
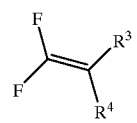
(I)
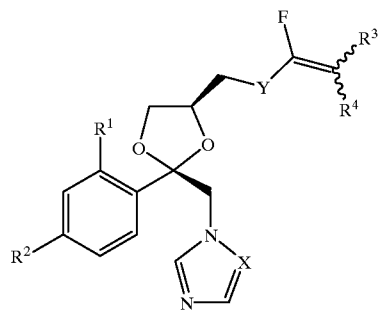
wherein, X, Y, $R^1$, $R^2$, $R^3$ and $R^4$ have the same meanings as defined in claim 1.
5. An antifungal composition comprising an effective amount of the compound of claim 1 as an active ingredient and a pharmaceutically acceptable carrier.
* * * * *